US009051345B2

(12) United States Patent
Barton et al.

(10) Patent No.: US 9,051,345 B2
(45) Date of Patent: Jun. 9, 2015

(54) METALLOINSERTOR COMPLEXES TARGETED TO DNA MISMATCHES

(71) Applicant: CALIFORNIA INSTITUTE OF TECHNOLOGY, Pasadena, CA (US)

(72) Inventors: Jacqueline K. Barton, San Marino, CA (US); Alexis Komor, Pasadena, CA (US); Curtis J. Schneider, Pasadena, CA (US); Alyson Weidmann, Pasadena, CA (US); Russell Ernst, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/917,447

(22) Filed: Jun. 13, 2013

(65) Prior Publication Data
US 2013/0345189 A1    Dec. 26, 2013

Related U.S. Application Data

(63) Continuation-in-part of application No. 13/511,642, filed as application No. PCT/US2012/037403 on May 10, 2012.

(60) Provisional application No. 61/484,514, filed on May 10, 2011, provisional application No. 61/613,292, filed on Mar. 20, 2012.

(51) Int. Cl.
C07F 15/00    (2006.01)
C07D 241/36    (2006.01)

(52) U.S. Cl.
CPC ........... *C07F 15/008* (2013.01); *C07F 15/0053* (2013.01); *C07D 241/36* (2013.01)

(58) Field of Classification Search
USPC ................. 514/185, 188; 544/225; 546/10, 12
See application file for complete search history.

(56) References Cited

U.S. PATENT DOCUMENTS

| | | | | |
|---|---|---|---|---|
| 6,031,098 | A * | 2/2000 | Barton et al. ...................... | 546/2 |
| 7,345,172 | B2 * | 3/2008 | Barton et al. ................. | 544/342 |
| 2002/0197638 | A1 | 12/2002 | Gjerde et al. | |
| 2003/0018020 | A1 | 1/2003 | Barton et al. | |
| 2013/0090319 | A1 | 4/2013 | Barton et al. | |

OTHER PUBLICATIONS

Barton et al. CAS:137:120645, 2002.*
Russell et al. CAS: 150: 277013, 2009.*
Brunner et al. CAS: 145: 98595, 2006.*
Banasik, Marek, et al.; Specific Inhibitors of Poly(ADP-Ribose) Synthetase and Mono(ADP-Ribosyl)transferase*; The Journal of Biological Chemistry; vol. 267; No. 3; Jan. 25, 1992; pp. 1569-1575.
Basu, Amitabha, et al.; "Copper Complexes of 1,1-Di-2-pyridylethanol: X-Ray Structures and Reaction with Oxygen"; Journal of the Chem. Soc, Chemical Comm., Jan. 1, 1987; pp. 1724-1725.
Brunner, Jens, et al.; "Targeting DNA Mismatches with Rhodium Intercalators Functionalized with a Cell-Penetrating Peptide"; Biochemistry; 2006, 45, pp. 12295-12302.
Copeland, Kimberly D., et al.; "DNA Cross-Linking with Metallointercalator-Peptide Conjugates"; Biochemistry, 2002; 41, pp. 12785-12797.
Costantino, Gabriele, et al.; "Modeling of Poly(ADP-ribose)polymerase (PARP) Inhibitors. Docking of Ligands and Quantitative Structure-Activity Relationship Analysis"; J. Med. Chem., 2001; 44, pp. 3786-3794.
Donawho, Cherrie K., et al.; "ABT-888, an Orally Active Poly(ADP-Ribose) Polymerase Inhibitor that Potentiates DNA-Damaging Agents in Preclinical Tumor Models"; Clin. Cancer Res.; 2007; 13; pp. 2728-2737.
Ernst, Russell J., et al.; "Selective Cytotoxicity of Rhodium Metalloinsertors in Mismatch Repair-Deficient Cells"; Biochemistry; 2011; 50; pp. 10919-10928.
Gratzner, Howard G.; "Monoclonal Antibody to 5-Bromo- and 5-Iododeoxyuridine: A New Reagent for Detection of DNA Replication"; Science; vol. 218; No. 4571; Oct. 29, 1982; pp. 474-475.
Greenwald, Richard B., et al.; "Effective drug delivery by PEGylated drug conjugates"; Advanced Drug Delivery Reviews; 55; 2003; pp. 217-250.
Greenwald, R. B.; "PEG drugs: an overview"; Journal of Controlled Release; 74; 2001; pp. 159-171.
Idziorek, Thieny, et al.; "YOPRO-1 permits cytofluorometric analysis of programmed cell death (apoptosis) without interfering with cell viability"; Journal of Immunological Methods; 185; 1995; pp. 249-258.
International Search Report and Written Opinion for corresponding PCT Application No. PCT/US2012/037403, mailed Dec. 14, 2012, 9pp.
Jackson, Brian A., et al.; "Recognition of Base Mismatches in DNA by 5,6-Chrysenequinone Diimine Complexes of Rhodium(III): A Proposed Mechanism for Preferential Binding in Destabilized Regions of the Double Helix"; Biochemistry 2000; vol. 39; pp. 6176-6182.
Junicke, Henrik, et al.; "A rhodium(III) complex for high-affinity DNA base-pair mismatch recognition"; PNAS; Apr. 1, 2003; vol. 100; No. 7; pp. 3737-3742.
Kirin, Srecko I., et al.: "Synthesis and Characterization of $Cu^{II}$ Complexes with Amino Acid Substituted Di(2-pyridyl)amine Ligands"; Eur. J. Inorg. Chem.; 2007; pp. 3686-3694.
Langer, R. S., et al.; "Present and future applications of biomaterials in controlled drug delivery systems"; Biomaterials; 1981; vol. 2; pp. 201-214.
Molineux, Graham; "Pegylation: Engineering Improved Biopharmaceuticals for Oncology"; Pharmacotherapy; 2003; 23; (8 Pt 2); 3S-8S; 6pp.
Mosmann, Tim; "Rapid Colorimetric Assay for Cellular Growth and Survival: Application to Proliferation and Cytotoxicity Assays"; Journal of Immunological Methods; 65; 1983; pp. 55-63.
Muerner, Hansruedi, et al.; "A Versatile Synthetic Approach to Rhodium(III) Diimine Metallointercalators: Condensation of o-Quinones with Coordinated cis-Ammines"; Inorg. Chem.; 1998; 37; pp. 3007-3012.
Purnell, Michael R., et al.; "Novel Inhibitors of Poly(ADP-Ribose) Synthetase"; Biochem. J.; 1980; 185; pp. 775-777.

(Continued)

*Primary Examiner* — Rei-Tsang Shiao
(74) *Attorney, Agent, or Firm* — Christie, Parker & Hale, LLP

(57) ABSTRACT

A composition including a Rh or Ru metalloinsertor complex specifically targets mismatch repair (MMR)-deficient cells. Selective cytotoxicity is induced in MMR-deficient cells upon uptake of the inventive metalloinsertor complexes.

14 Claims, 49 Drawing Sheets

(56) References Cited

OTHER PUBLICATIONS

Reitmair, Armin H., et al.; "Mutator Phenotype in Msh2-deficient Murine Embryonic Fibroblasts"; Cancer Res.; 1997; 57; pp. 3765-3771.

Roberts, M. J. et al.; "Chemistry for peptide and protein PEGylation"; Advanced Drug Delivery Reviews; 2002; 54; pp. 459-476.

Zalipsky, Samuel; "Chemistry of polyethylene glycol conjugates with biologically active molecules"; Advanced Drug Delivery Reviews 16; 1995; pp. 157-182.

Zeglis, Brian M, et al.; "DNA base mismatch detection with bulky rhodium intercalators: synthesis and applications"; Nature Protocols; vol. 2; No. 2; 2007; pp. 357-371.

International Search Report and Written Opinion for corresponding PCT Application No. PCT/US2013/045705, mailed Feb. 19, 2014; 11pp.

Ernst, Russell J, et al.; "DNA Mismatch Binding and Antiproliferative Activity of Rhodium Metalloinsertors"; J. Am. Chem. Soc.; 131; Jan. 28, 2009; pp. 2359-2366 (9pp.).

Lim, Mi Hee, et al.; "DNA Strand Cleavage near a CC Mismatch Directed by a Metalloinsertor"; Inorg. Chem.; 2007; 46; pp. 9528-9530 (4pp.).

\* cited by examiner

[Rh(DPK)(NH$_3$)$_2$chrysi]$^{3+}$

[Rh(DPE)(NH$_3$)$_2$chrysi]$^{2+}$

[Rh(NH$_3$)$_4$phzi]$^{3+}$

[Rh(HDPA)$_2$phzi]$^{3+}$

[Rh(MeDPA)₂phzi]³⁺

[Rh(MeDPA)₂chrysi]³⁺

[Rh(MeDPA)(phen)chrysi]$^{3+}$

[Rh(EtDPA)(phen)chrysi]$^{3+}$

[Rh(PrDPA)(phen)chrysi]³⁺

[Rh(HexDPA)(phen)chrysi]³⁺

[Rh(PrDPA)₂chrysi]³⁺

[Rh(DPAE)₂chrysi]³⁺

[Rh(HDPA)(phen)chrysi]³⁺

[Rh(DPE)(phen)chrysi]²⁺

[Rh(chrysi)(phen)(PyPrO)]²⁺

[Rh(chrysi)(phen)(PPE)]²⁺

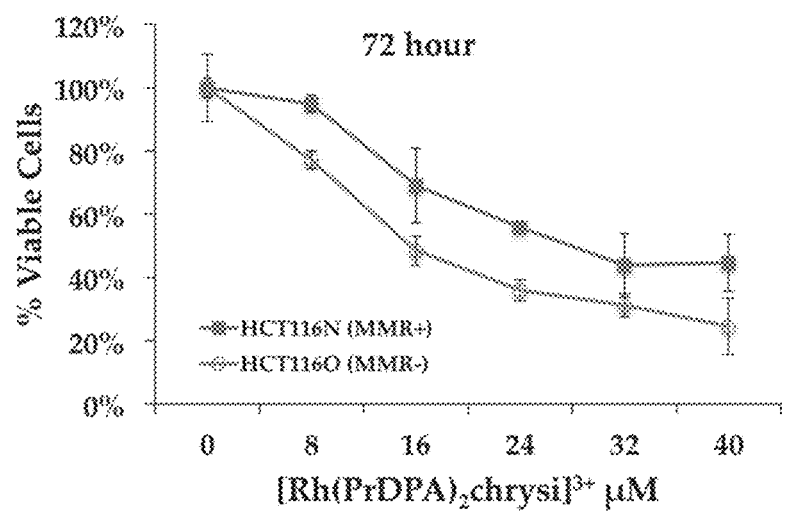

20 μM [Rh(HDPA)$_2$chrysi]$^{3+}$

No Rh

20 μM [Rh(HDPA)chrysi]$^{3+}$
72 hours

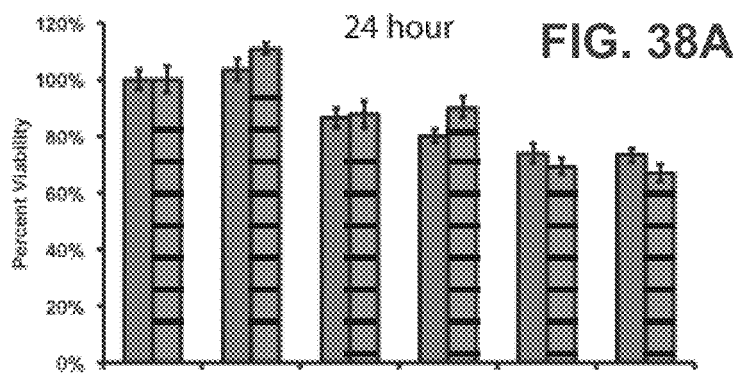
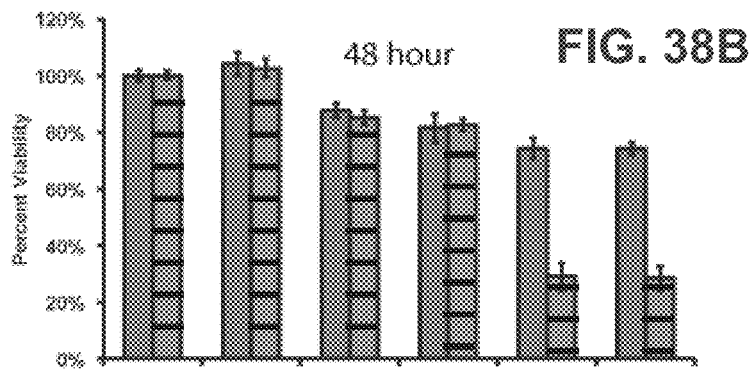
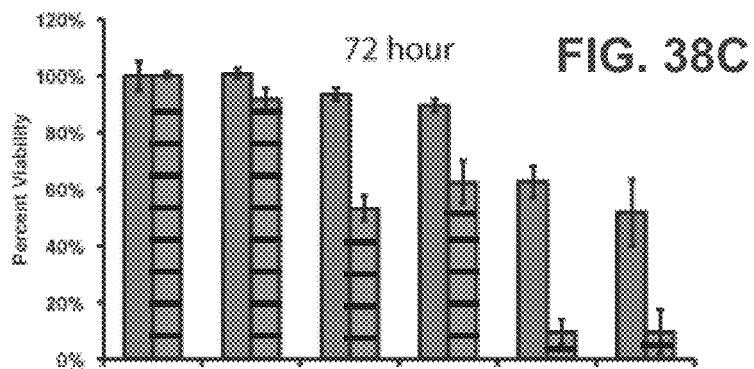
FIG. 38A
FIG. 38B
FIG. 38C

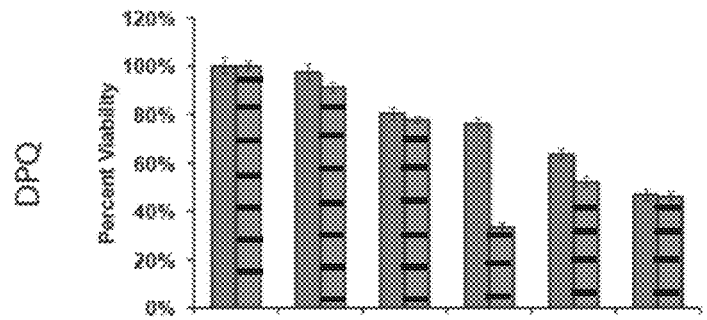
FIG. 39A
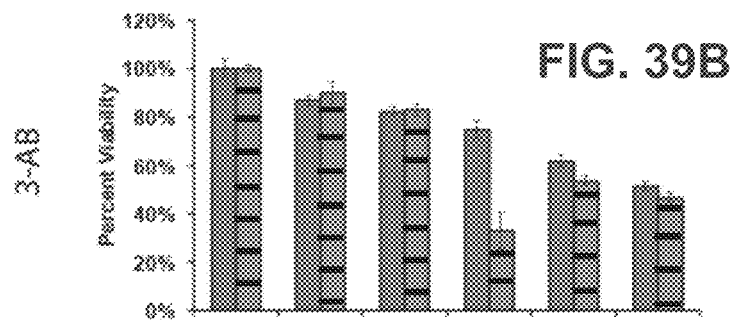
FIG. 39B
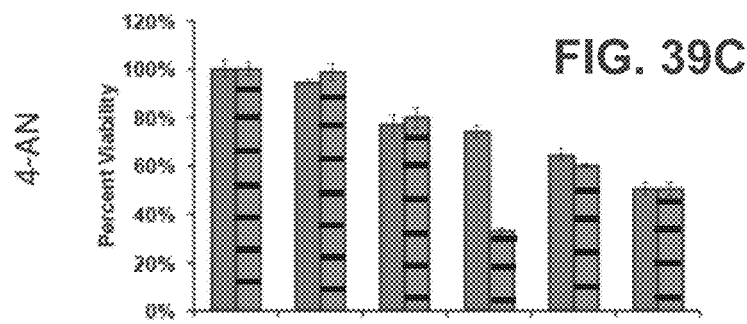
FIG. 39C
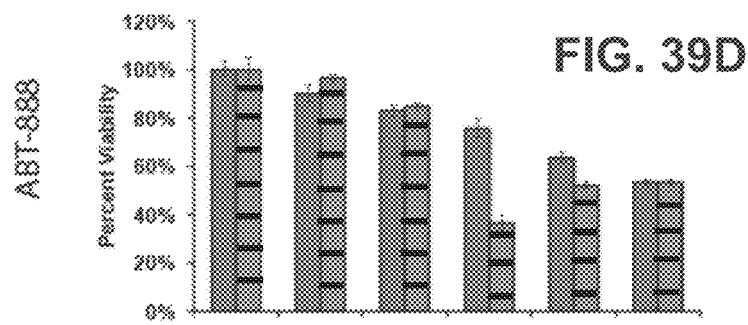
FIG. 39D
 HCT116N (MMR+)　　 HCT116O (MMR−)

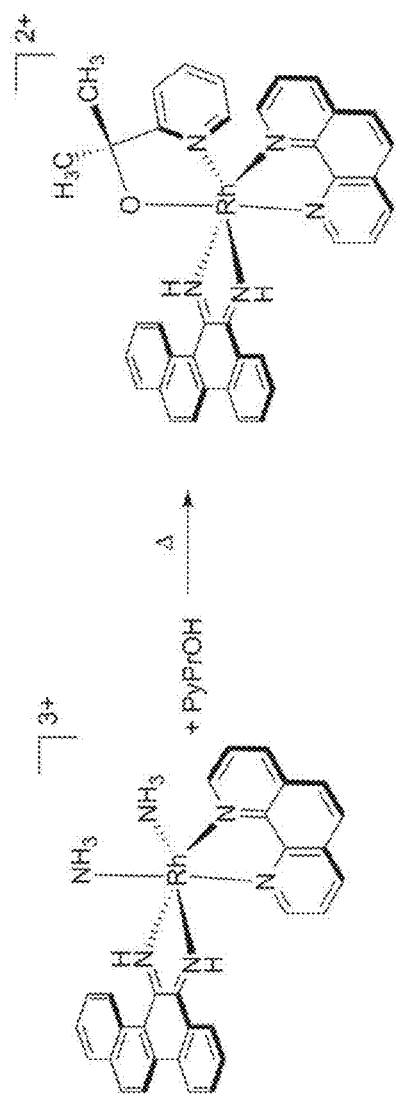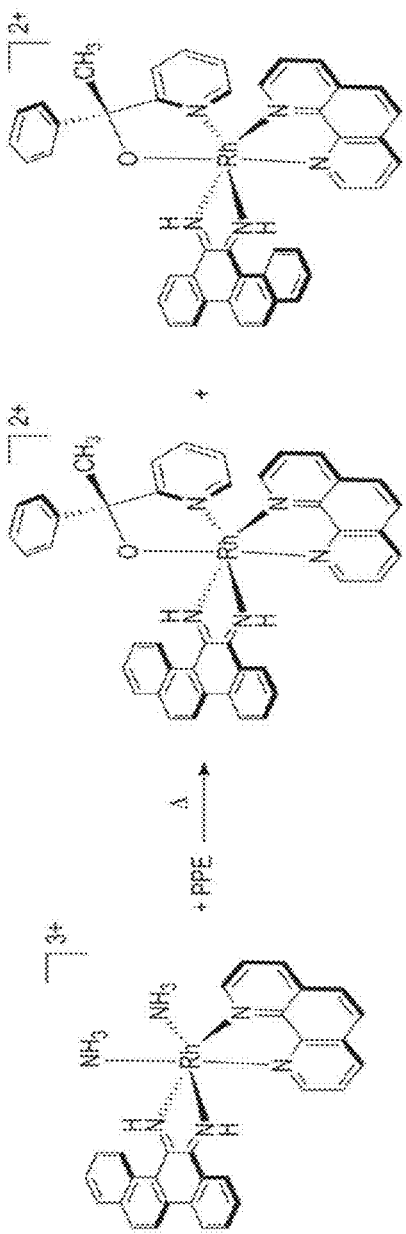
FIG. 43A
FIG. 43B

METALLOINSERTOR COMPLEXES TARGETED TO DNA MISMATCHES

CROSS-REFERENCE TO RELATED APPLICATION(S)

The present application is a continuation-in-part of U.S. patent application Ser. No. 13/511,642 filed May 23, 2012, which is a National Phase Patent Application and claims priority to and benefit of International Application Number PCT/US12/37403, filed on May 10, 2012, which claims priority to and benefit of U.S. Provisional Application Ser. No. 61/484,514 filed May 10, 2011 and U.S. Provisional Application Ser. No. 61/613,292 filed Mar. 20, 2012, the entire contents of all of which are incorporated herein by reference.

STATEMENT REGARDING FEDERALLY SPONSORED RESEARCH OR DEVELOPMENT

This invention was made with government support under GM033309 awarded by the National Institutes of Health. The government has certain rights in the invention.

FIELD

This disclosure is directed to metalloinsertor complexes and the use of these complexes to selectively target specific deficient cells.

BACKGROUND

Mismatches in DNA arise naturally as a result of replication errors, endogenous DNA damaging agents, and spontaneous processes such as cytosine deamination. The mismatch repair (MMR) pathway acts to correct mismatches before subsequent rounds of replication, reducing the number of DNA mismatches in the human genome from ~1000 to ~1. The loss of MMR carries dire consequences, including increased mutation rates, carcinogenesis, and resistance to a variety of clinical anti-cancer agents, such as anti-metabolites, DNA alkylators, and cisplatin. Indeed, deficiencies in MMR have been linked to a variety of cancers, in particular, nonhereditary colorectal carcinoma, and are also associated with resistance or tolerance to many common therapeutics. Furthermore, this resistance to commonly used agents leads to enrichment of MMR-deficient cells; roughly half of secondary leukemias show MMR-deficiency. These issues point to the need for a therapeutic agent that specifically targets MMR-deficient cells. Of course, any potential agent must first reach its target before it may bind.

To that end, metalloinsertors have been developed to target DNA mismatches in vitro. DNA mismatches, owing to their loss of hydrogen bonding and poor stacking, are destabilized relative to well matched DNA. It is this thermodynamic destabilization that allows for a means of targeting mismatches, since mismatches do not significantly perturb the structure of the B-form DNA duplex. However, while existing metalloinsertors have been used to detect the existence of DNA mismatches, to date, the existing metalloinsertors have not been shown to cause cell death.

SUMMARY

Embodiments of the present invention are directed to a metalloinsertor complex capable of specifically targeting MMR-deficient cells.

In some embodiments of the present invention, a composition includes a complex represented by Formula I, depicted below.

$$M^{m+}(L_1)(L_2)(L_3)(L_4)(L_5) \quad \text{Formula I}$$

In Formula I, M is rhodium or ruthenium, and m is 2 or 3. $L_1$ is benzo[a]phenazine-5,6-diimine (phzi) or chrysene-5,6-diimine (chrysi), as depicted below.

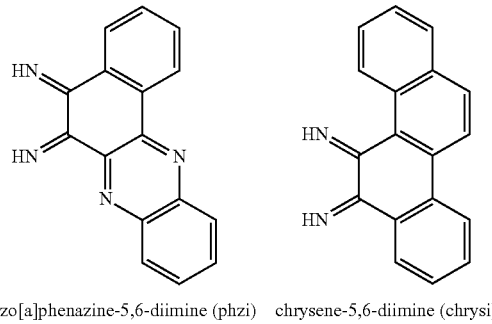

benzo[a]phenazine-5,6-diimine (phzi)   chrysene-5,6-diimine (chrysi)

In Formula I, each of $L_2$ through $L_5$ is either $NH_3$ or combines with an adjacent one of $L_2$ through $L_5$ to form a single ligand with two coordination sites to M, where the single ligand with two coordination sites to M is selected from:

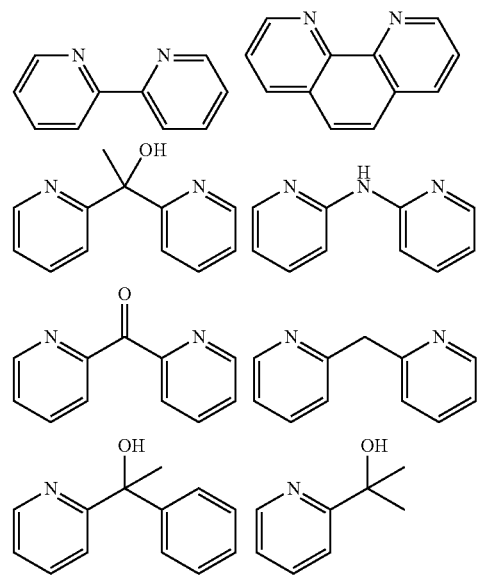

Formula II

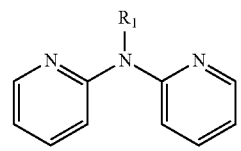

Formula III

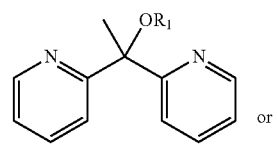

or

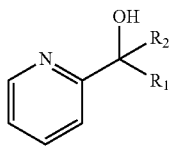

Formula IV

In Formula II, Formula III, and Formula IV, $R_1$ and $R_2$ are each independently selected from alkyl groups terminating in one selected from $CH_3$, OH, SH, $NH_2$, COOH, $N_3$, or alkynyl-linked peptide moieties, and PEGylated groups terminating in one selected from $CH_3$, OH, SH, $NH_2$, COOH, $N_3$, or alkynyl-linked peptide moieties.

In some embodiments of the present invention, a method for selectively inducing cytotoxicity in mismatch repair (MMR)-deficient cells includes providing a metalloinsertor complex of Formula I to the MMR-deficient cells. Here, a decrease in cell viability in the MMR-deficient cells that does not, or would not, comparably decrease cell viability in MMR-proficient cells, indicates selective cytotoxicity in MMR-deficient cells.

In some embodiments, a method of decreasing MMR-deficient cell proliferation includes providing a metalloinsertor complex of Formula I to MMR-deficient cells.

BRIEF DESCRIPTION OF THE DRAWINGS

FIG. 18C is a graph of the amount (%) of viable cells as a function of [Rh(PrDPA)$_2$chrysi]$^{3+}$ concentration in the HCT116N (squares) and the HCT116O (circles) cell lines after a 72 hour incubation, according to embodiments of the present invention.

FIG. 38A is a graph comparing the percent viability of HCT116N (solid) and HCT116O (lined) cells treated with 0, 15, and 30 μm [Rh(HDPA)$_2$chrysi]$^{3+}$ with or without 20 μm of the pan-caspase inhibitor Z-VAD-FMK for a 24 hour incubation, and labeled with MTT, according to embodiments of the present invention.

FIG. 38B is a graph comparing the percent viability of HCT116N and HCT116O cells treated with 0, 15, and 30 μm [Rh(HDPA)$_2$chrysi]$^{3+}$ with or without 20 μm of the pan-caspase inhibitor Z-VAD-FMK for a 48 hour incubation, and labeled with MTT, according to embodiments of the present invention.

FIG. 38C is a graph comparing the percent viability of HCT116N and HCT116O cells treated with 0, 15, and 30 μm [Rh(HDPA)$_2$chrysi]$^{3+}$ with or without 20 μm of the pan-caspase inhibitor Z-VAD-FMK for a 72 hour incubation, and labeled with MTT, according to embodiments of the present invention.

FIG. 39A is a graph comparing the percent viability of HCT116N (solid) and HCT116O (lined) cells treated with (+=25 μM, or ++=50 μM) or without the PARP inhibitor DPQ, and with or without 20 μM [Rh(HDPA)$_2$chrysi]$^{3+}$ for a 72 hour incubation, and labeled with MTT, according to embodiments of the present invention.

FIG. 39B is a graph comparing the percent viability of HCT116N (solid) and HCT116O (lined) cells treated with (+=2 mM, or ++=3 mM) or without the PARP inhibitor 3-AB, and with or without 20 μM [Rh(HDPA)$_2$chrysi]$^{3+}$ for a 72 hour incubation, and labeled with MTT, according to embodiments of the present invention.

FIG. 39C is a graph comparing the percent viability of HCT116N (solid) and HCT116O (lined) cells treated with (+=10 μM, or ++=10 μM) or without the PARP inhibitor 4-AN, and with or without 20 μM [Rh(HDPA)$_2$chrysi]$^{3+}$ for a 72 hour incubation, and labeled with MTT, according to embodiments of the present invention.

FIG. 39D is a graph comparing the percent viability of HCT116N (solid) and HCT116O (lined) cells treated with (+=5 μM, or ++=10 μM) or without the PARP inhibitor ABT-888, and with or without 20 μM [Rh(HDPA)$_2$chrysi]$^{3+}$ for a 72 hour incubation, and labeled with MTT, according to embodiments of the present invention.

FIG. 43A is a schematic of the synthesis of [Rh(chrysi)(phen)(PyPrO)]$^{2+}$, according to embodiments of the present invention.

FIG. 43B is a schematic of the synthesis of [Rh(chrysi)(phen)(PPE)]$^{2+}$, according to embodiments of the present invention.

DETAILED DESCRIPTION

Figure 1A:
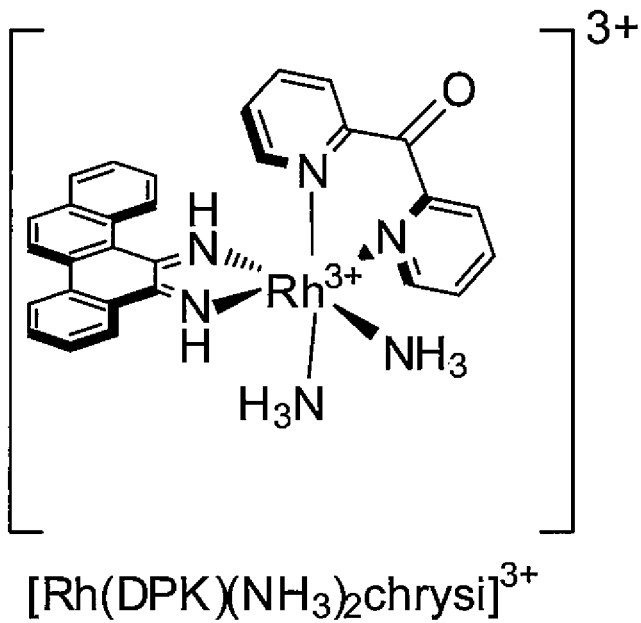
FIG. 1A is the structure of the rhodium metalloinsertor $[Rh(DPK)(NH_3)_2chrysi]^{3+}$, according to embodiments of the present invention.
Figure 1B:
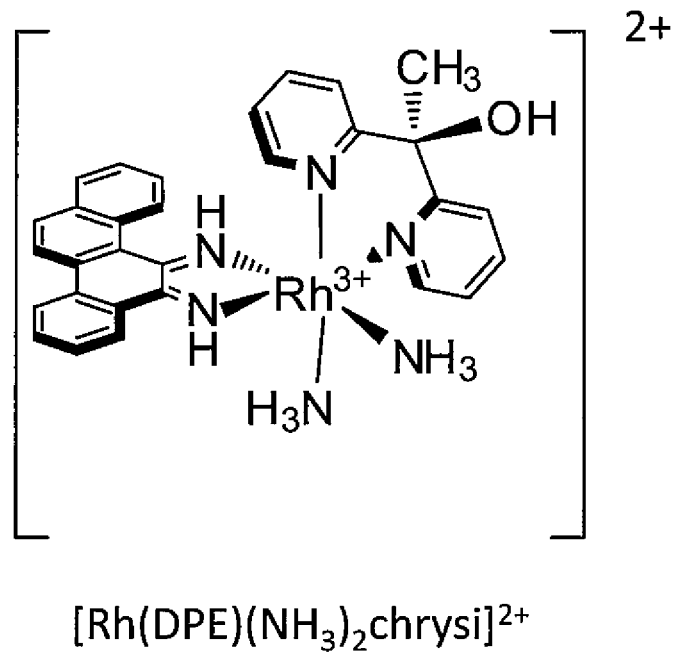
FIG. 1B is the structure of the rhodium metalloinsertor $[Rh(DPE)(NH_3)_2chrysi]^{2+}$, according to embodiments of the present invention.
Figure 1C:
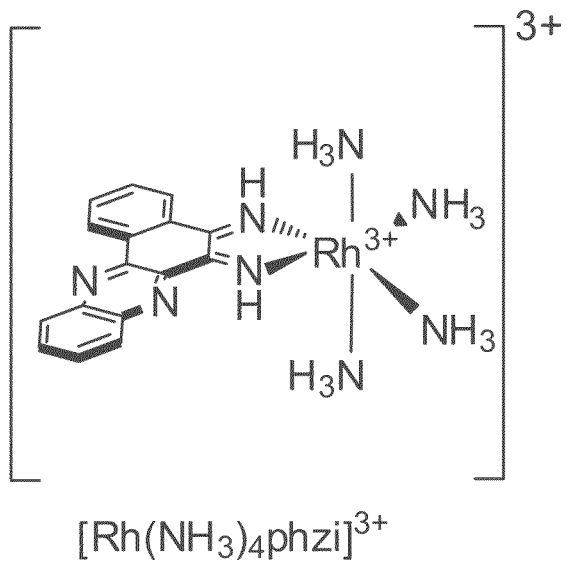
FIG. 1C is the structure of the rhodium metalloinsertor $[Rh(NH_3)_4phzi]^{3+}$, according to embodiments of the present invention.
Figure 1D:
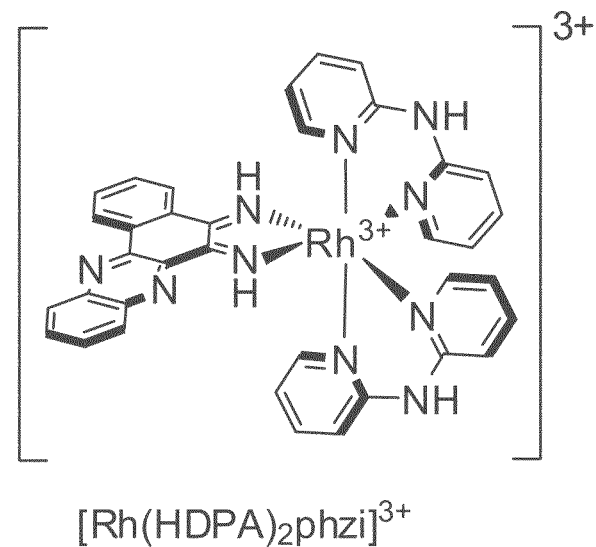
FIG. 1D is the structure of the rhodium metalloinsertor $[Rh(HDPA)_2phzi]^{3+}$, according to embodiments of the present invention.
Figure 1E:
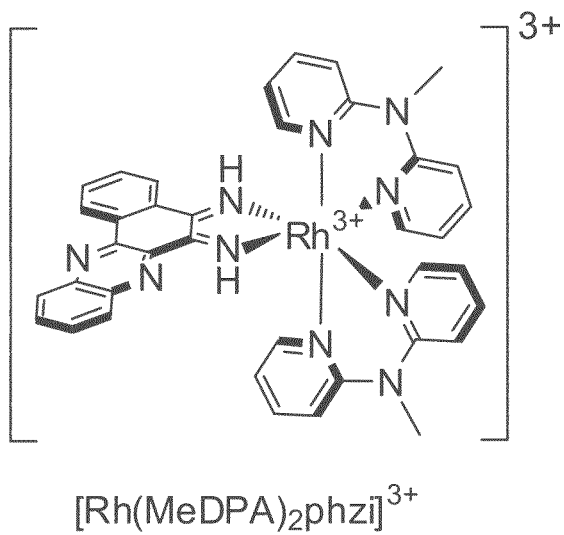
FIG. 1E is the structure of the rhodium metalloinsertor $[Rh(MeDPA)_2phzi]^{3+}$, according to embodiments of the present invention.
Figure 1F:
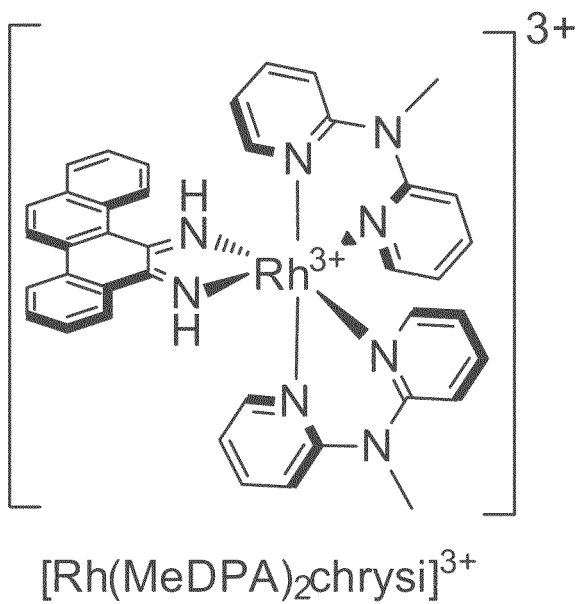
FIG. 1F is the structure of the rhodium metalloinsertor $[Rh(MeDPA)_2chrysi]^{3+}$, according to embodiments of the present invention.
Figure 1G:
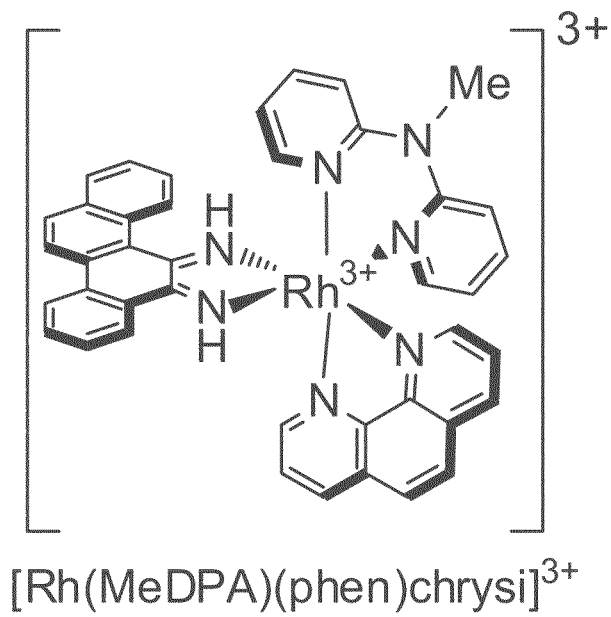
FIG. 1G is the structure of the rhodium metalloinsertor $[Rh(MDPA)_2(phen)(chrysi)]^{3+}$, according to embodiments of the present invention.
Figure 1H:
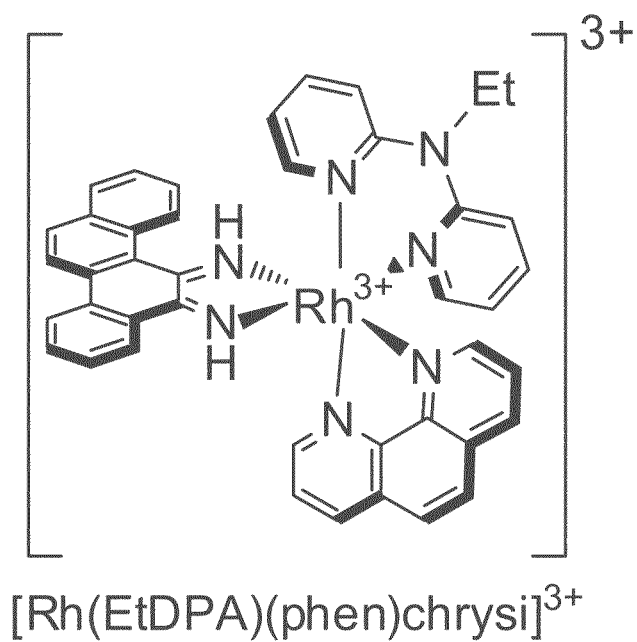
FIG. 1H is the structure of the rhodium metalloinsertor $[Rh(PrDPA)_2(phen)(chrysi)]^{3+}$, according to embodiments of the present invention.
Figure 1I:
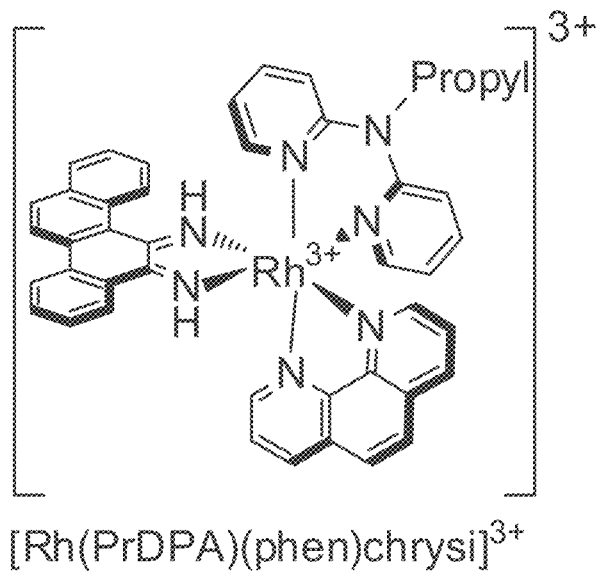
FIG. 1I is the structure of the rhodium metelloinsertor $[Rh(PrDPA)(phen)(chrysi)]^{3+}$, according to embodiments of the present invention.
Figure 1J:
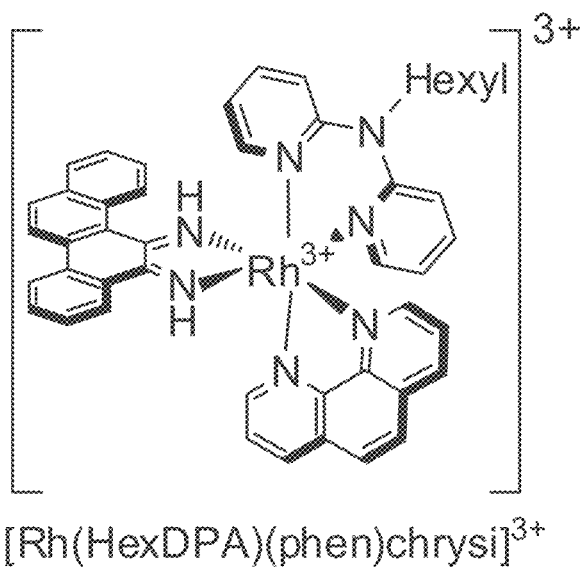
FIG. 1J is the structure of the rhodium metalloinsertor $[Rh(HexDPA)_2(phen)(chrysi)]^{3+}$, according to embodiments of the present invention.
Figure 1K:
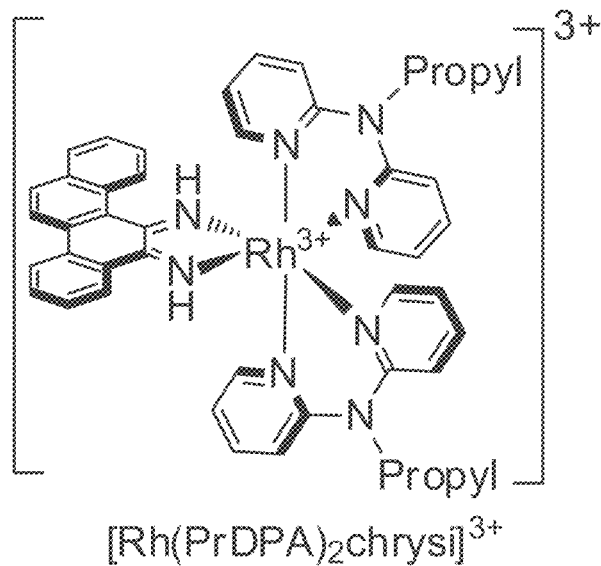
FIG. 1K is the structure of the rhodium metalloinsertor $[Rh(PrDPA)_2chrysi]^{3+}$, according to embodiments of the present invention.
Figure 1L:
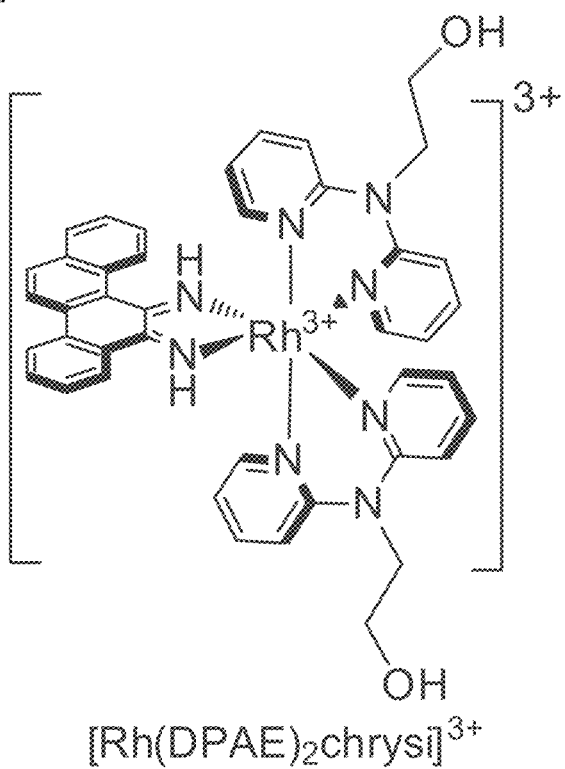
FIG. 1L is the structure of the rhodium metalloinsertor $[Rh(DPAE)_2chrysi]^{3+}$, according to embodiments of the present invention.
Figure 1M:
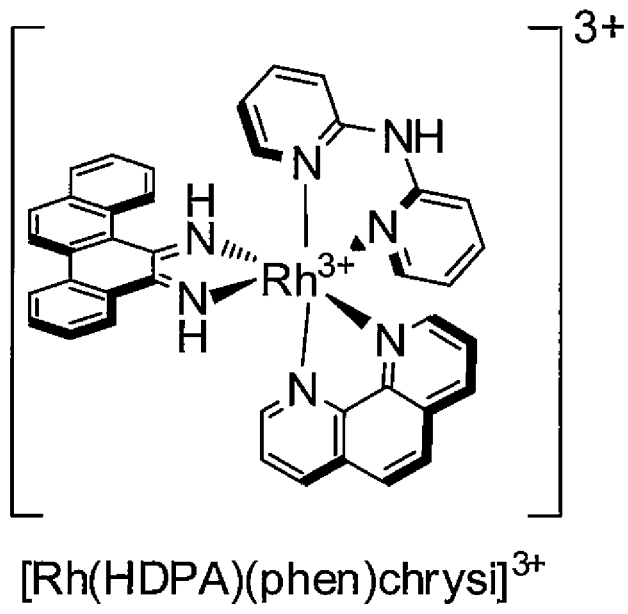
FIG. 1M is the structure of the rhodium metalloinsertor $[Rh(HDPA)(phen)(chrysi)]^{3+}$, according to embodiments of the present invention.
Figure 1N:
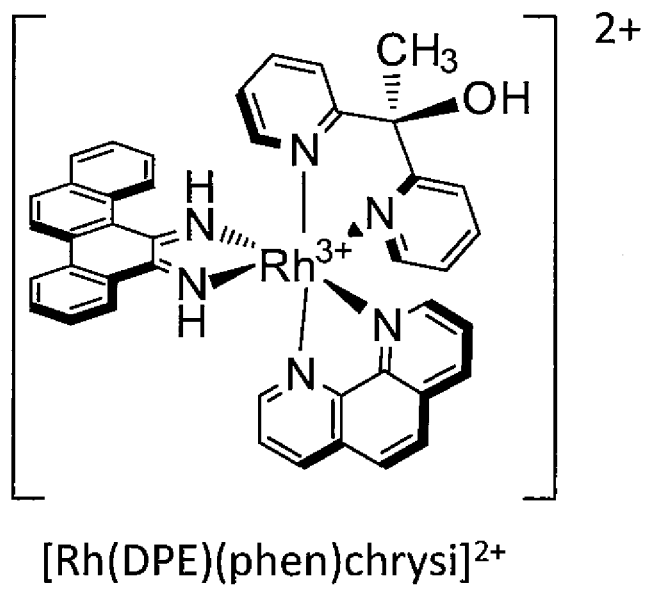
FIG. 1N is the structure of the rhodium metalloinsertor $[Rh(DPE)(phen)(chrysi)]^{2+}$, according to embodiments of the present invention.
Figure 1P:
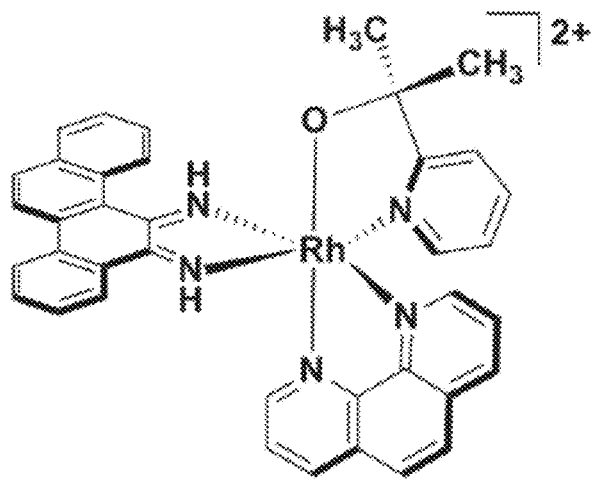
FIG. 1P is the structure of the rhodium metalloinsertor $[Rh(chrysi)(phen)(PyPrO)]^{2+}$, according to embodiments of the present invention.
Figure 1Q:
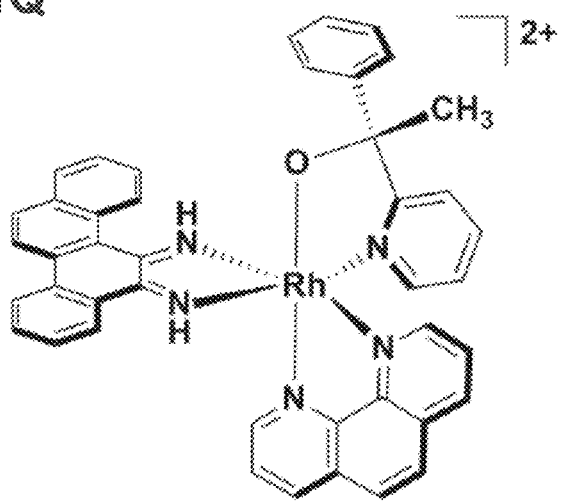
FIG. 1Q is the structure of the rhodium metalloinsertor $[Rh(chrysi)(phen)(PPE)]^{2+}$, according to embodiments of the present invention.
Figure 2:
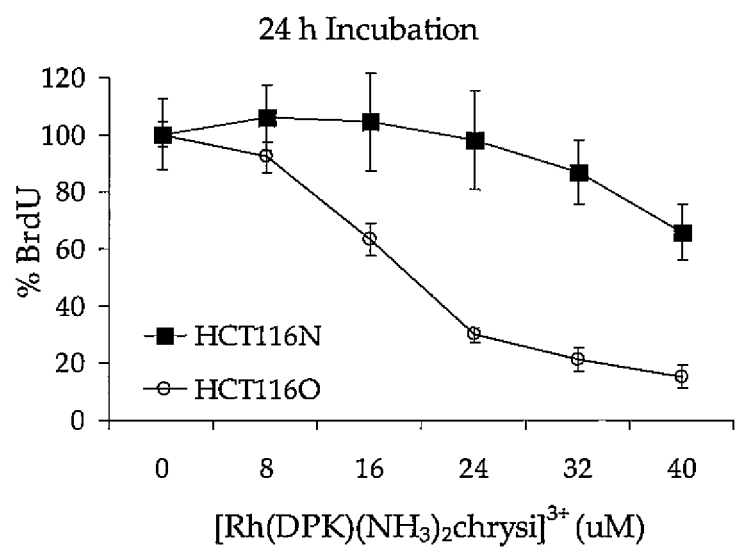
FIG. 2 is a graph of the amount (%) of BrdU incorporation as a function of $[Rh(DPK)(NH_3)_2chrysi]^{3+}$ concentration in the HCT116N (squares) and the HCT116O (circles) cell lines after a 24 hour incubation, according to embodiments of the present invention.
Figure 3:
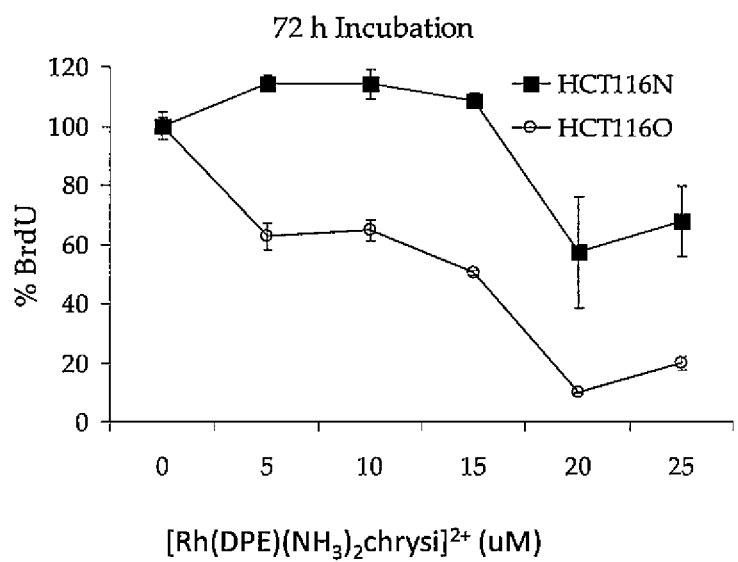
FIG. 3 is a graph of the amount (%) of BrdU incorporation as a function of $[Rh(DPE)(NH_3)_2chrysi]^{2+}$ concentration in the HCT116N (squares) and the HCT116O (circles) cell lines after a 72 hour incubation, according to embodiments of the present invention.
Figure 4:
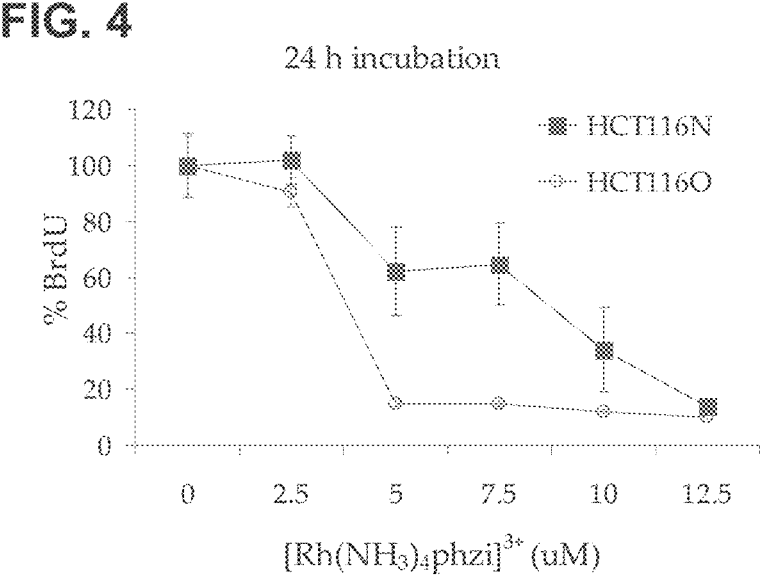
FIG. 4 is a graph of the amount (%) of BrdU incorporation as a function of $[Rh(NH_3)_4phzi]^{3+}$ concentration in the HCT116N (squares) and the HCT116O (circles) cell lines after a 24 hour incubation, according to embodiments of the present invention.
Figure 5:
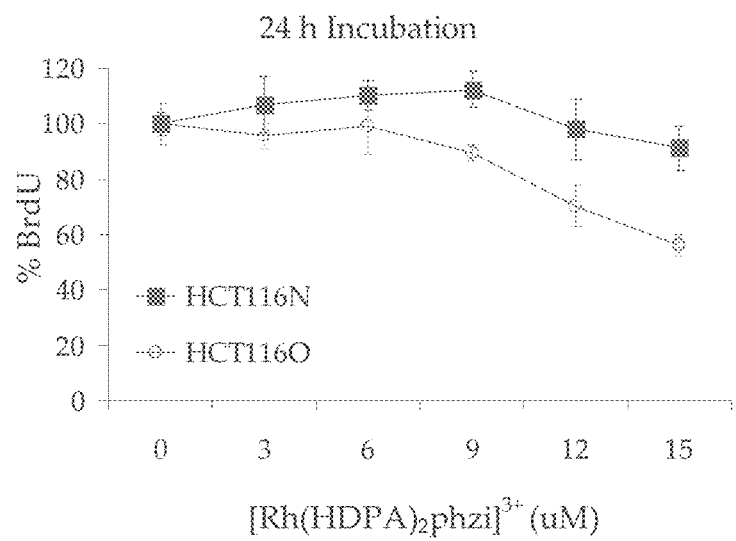
FIG. 5 is a graph of the amount (%) of BrdU incorporation as a function of $[Rh(HDPA)_2phzi]^{3+}$ concentration in the HCT116N (squares) and the HCT116O (circles) cell lines after a 24 hour incubation, according to embodiments of the present invention.
Figure 6:
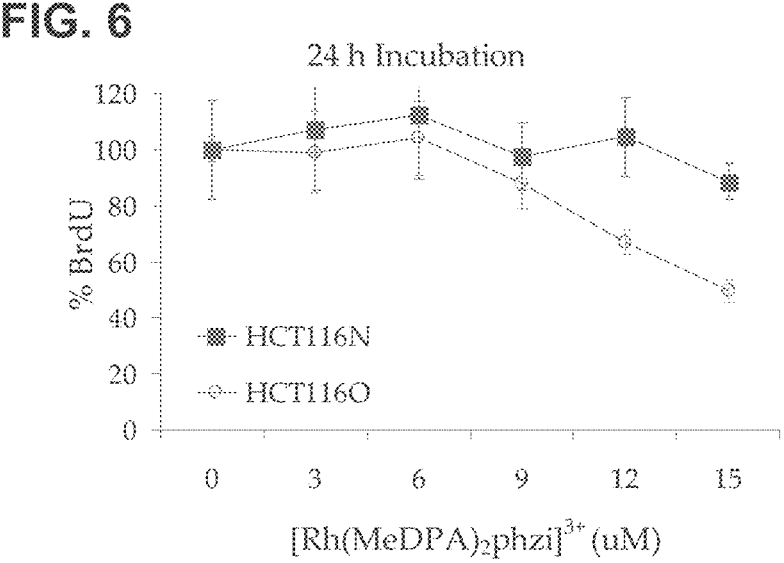
FIG. 6 is a graph of the amount (%) of BrdU incorporation as a function of $[Rh(DPE)(NH_3)_2phzi]^{3+}$ concentration in the HCT116N (squares) and the HCT116O (circles) cell lines after a 24 hour incubation, according to embodiments of the present invention.
Figure 7:
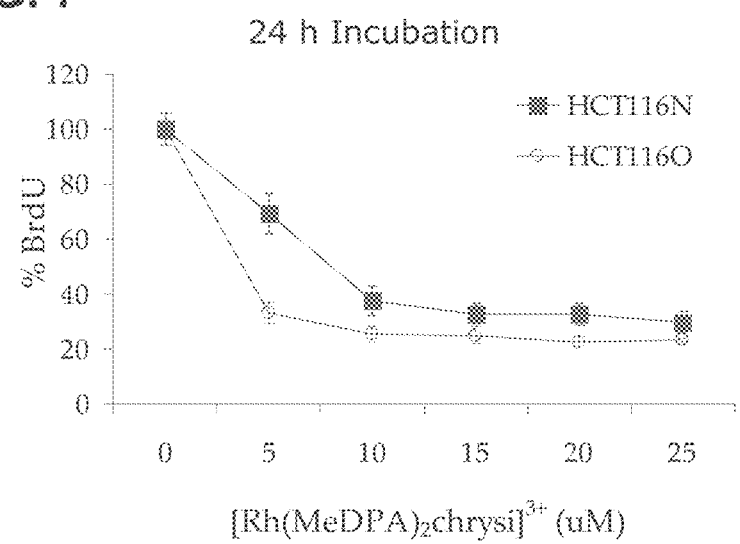
FIG. 7 is a graph of the amount (%) of BrdU incorporation as a function of $[Rh(MeDPA)_2chrysi]^{3+}$ concentration in the HCT116N (squares) and the HCT116O (circles) cell lines after a 24 hour incubation, according to embodiments of the present invention.
Figure 8:
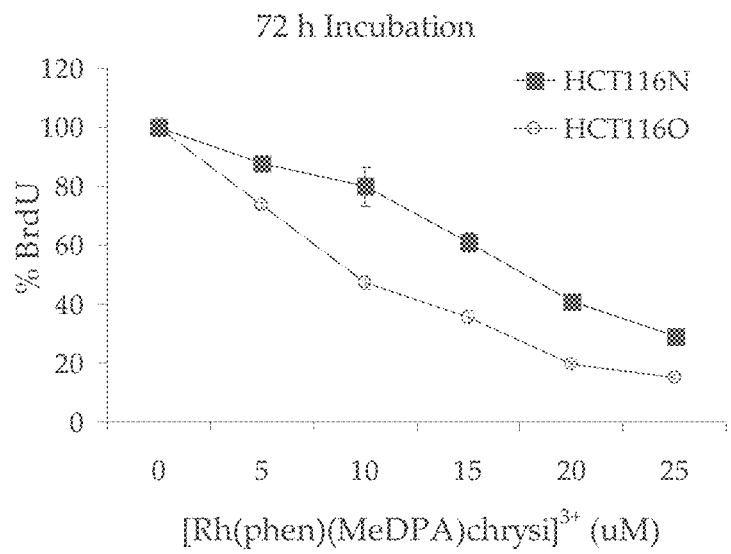
FIG. 8 is a graph of the amount (%) of BrdU incorporation as a function of $[Rh(phen)(MeDPA)chrysi]^{3+}$ concentration in the HCT116N (squares) and the HCT116O (circles) cell lines after a 72 hour incubation, according to embodiments of the present invention.
Figure 9:
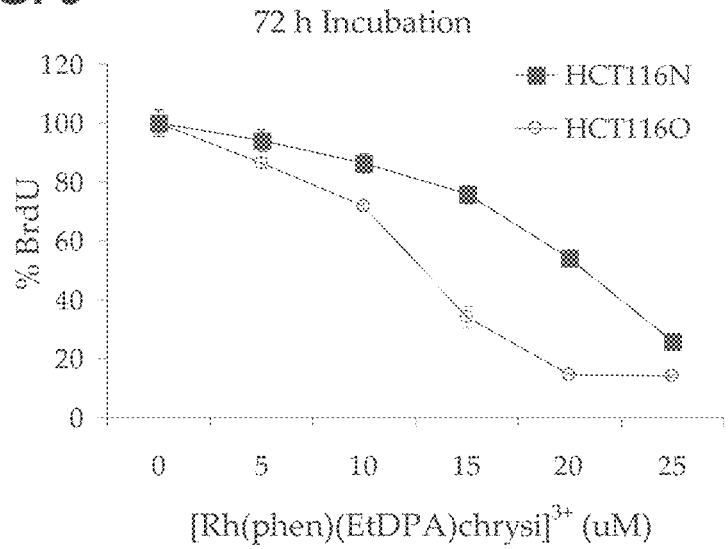
FIG. 9 is a graph of the amount (%) of BrdU incorporation as a function of $[Rh(phen)(EtDPA)chrysi]^{3+}$ concentration in the HCT116N (squares) and the HCT116O (circles) cell lines after a 72 hour incubation, according to embodiments of the present invention.
Figure 10:
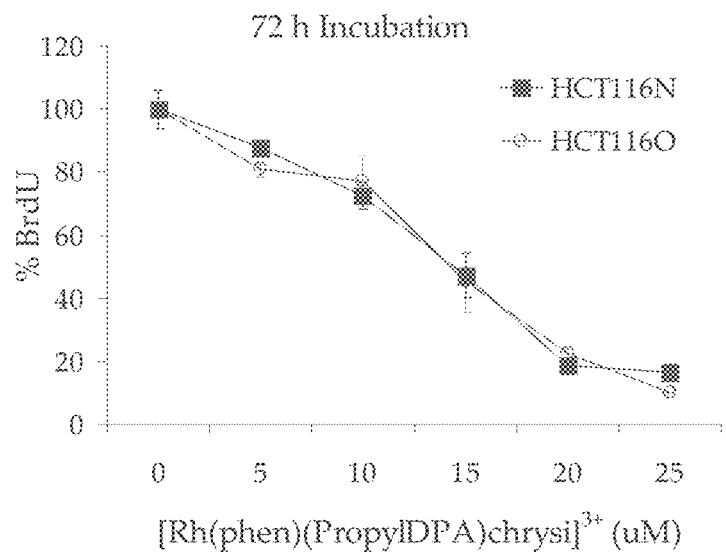
FIG. 10 is a graph of the amount (%) of BrdU incorporation as a function of $[Rh(phen)(PrDPA)_2chrysi]^{3+}$ concentration in the HCT116N (squares) and the HCT116O (circles) cell lines after a 72 hour incubation, according to embodiments of the present invention.
Figure 11:
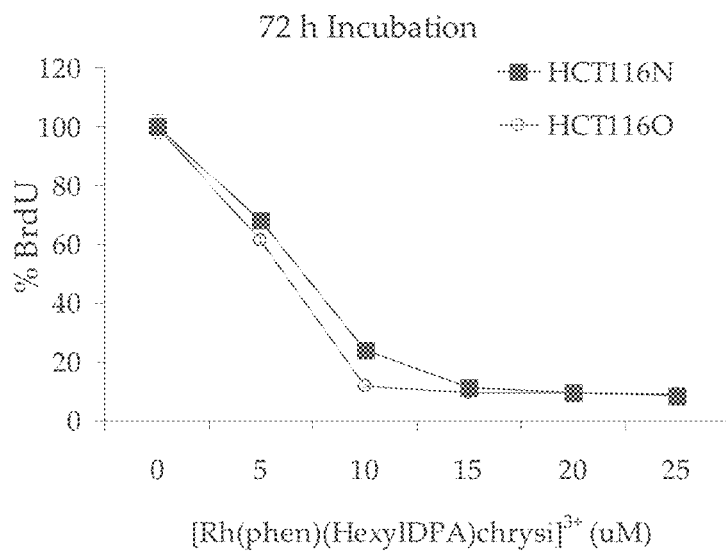
FIG. 11 is a graph of the amount (%) of BrdU incorporation as a function of $[Rh(phen)(hexylDPA)chrysi]^{3+}$ concentration in the HCT116N (squares) and the HCT116O (circles) cell lines after a 72 hour incubation, according to embodiments of the present invention.
Figure 12:
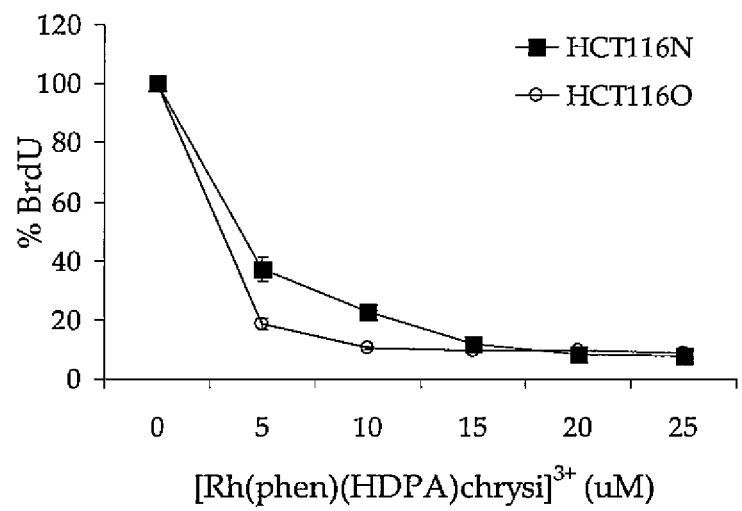
FIG. 12 is a graph of the amount (%) of BrdU incorporation as a function of $[Rh(phen)(HDPA)chrysi]^{3+}$ concentration in the HCT116N (squares) and the HCT116O (circles) cell lines after a 72 hour incubation, according to embodiments of the present invention.
Figure 13:
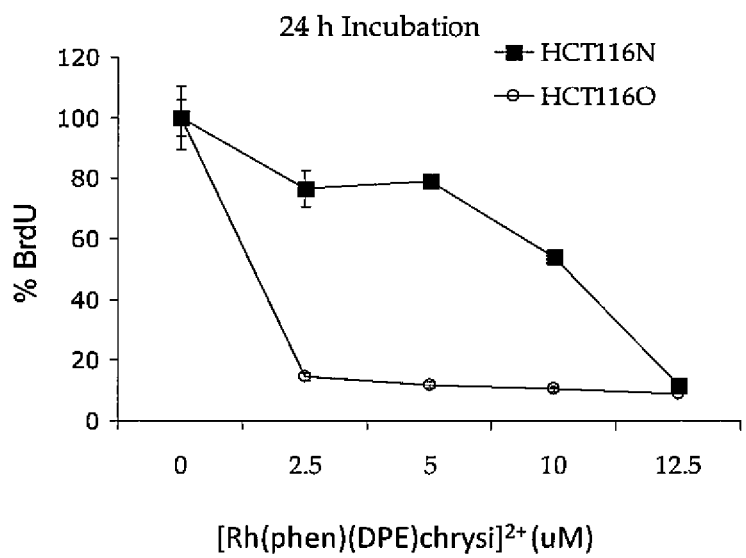
FIG. 13 is a graph of the amount (%) of BrdU incorporation as a function of [Rh(DPE)(phen)(chrysi)]$^{2+}$, concentration in the HCT116N (squares) and the HCT116O (circles) cell lines after a 24 hour incubation, according to embodiments of the present invention.
Figure 14A:
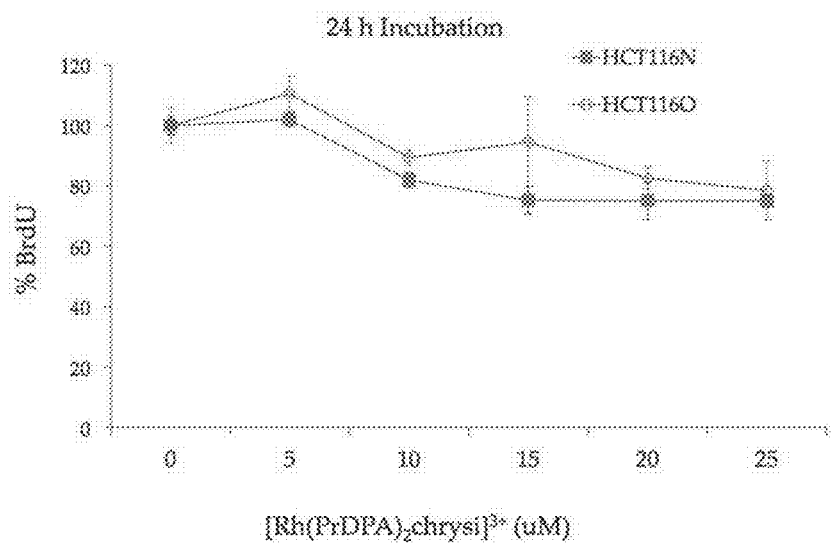
FIG. 14A is a graph of the amount (%) of BrdU incorporation as a function of [Rh(PropylDPA)$_2$chrysi]$^{3+}$ concentration in the HCT116N (squares) and the HCT116O (circles) cell lines after a 24 hour incubation, according to embodiments of the present invention.
Figure 14B:
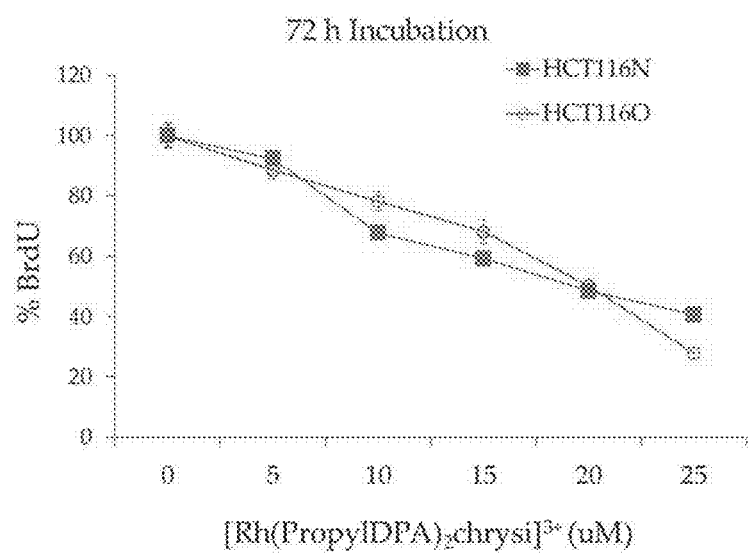
FIG. 14B is a graph of the amount (%) of BrdU incorporation as a function of [Rh(PropylDPA)$_2$chrysi]$^{3+}$ concentration in the HCT116N (squares) and the HCT116O (circles) cell lines after a 72 hour incubation, according to embodiments of the present invention.
Figure 15A:
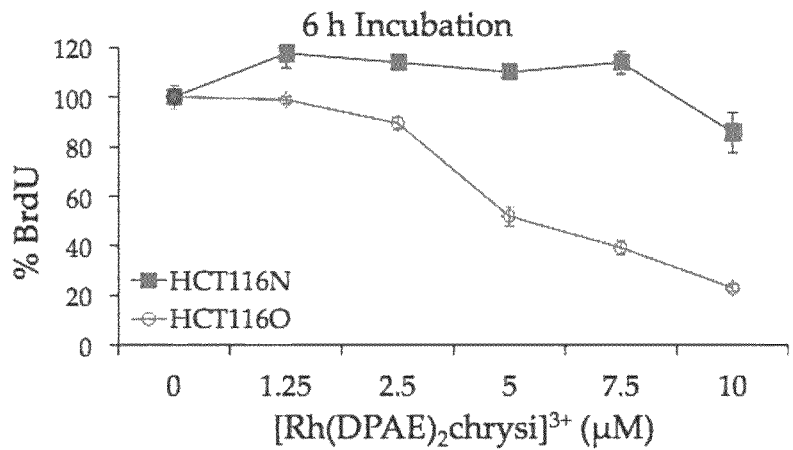
FIG. 15A is a graph of the amount (%) of BrdU incorporation as a function of [Rh(DPAE)$_2$chrysi]$^{3+}$ concentration in the HCT116N (squares) and the HCT116O (circles) cell lines after a 6 hour incubation, according to embodiments of the present invention.
Figure 15B:
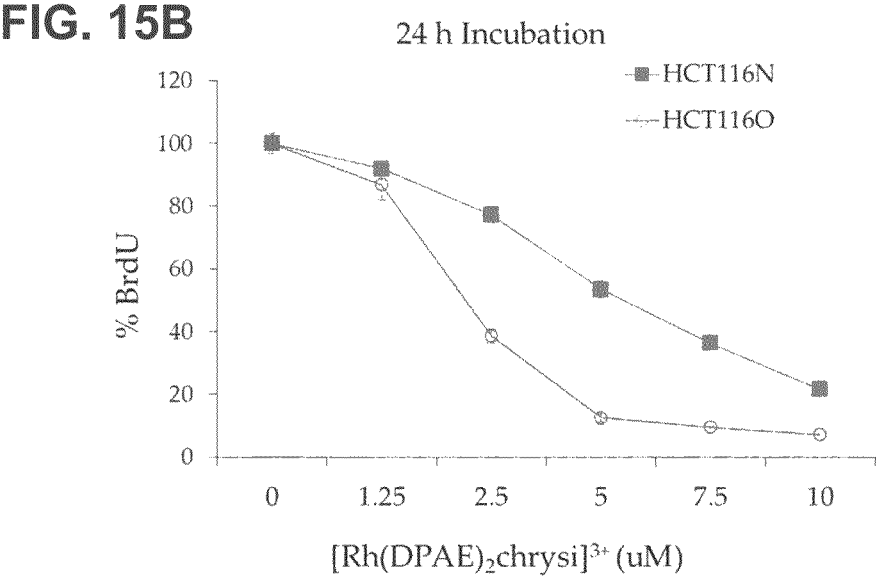
FIG. 15B is a graph of the amount (%) of BrdU incorporation as a function of [Rh(DPAE)$_2$chrysi]$^{3+}$ concentration in the HCT116N (squares) and the HCT116O (circles) cell lines after a 24 hour incubation, according to embodiments of the present invention.

Rhodium complexes bearing the sterically expansive 5,6-chrysene diimine (chrysi) ligand are known to bind selectively to mismatched sites in duplex DNA in vitro. The x-ray crystal structures of Rh(bpy)$_2$chrysi$^{3+}$ bound to mismatches show a novel insertion binding mode in which the chrysi ligand displaces the mismatched bases from the minor groove. These chrysi complexes of rhodium are capable of selectively inhibiting the cellular proliferation of cells deficient in their mismatch repair (MMR) machinery. Improvements to the design of mismatch specific rhodium complexes include reducing potential steric interactions using smaller ancillary ligands, improving the mismatch binding affinity through modification of the inserting ligand, and optimizing the scaffold for cellular uptake and conjugate development.

It is to be understood that unless otherwise indicated this invention is not limited to specific reactants, reaction conditions, ligands, metal complexes, or the like, as such may vary. It is also to be understood that the terminology used herein is for the purpose of describing particular embodiments only and is not intended to be limiting. For example, the present invention is directed to both rhodium and ruthenium complexes. However, a person having ordinary skill in the art would recognize that the Rh metal in the exemplified complexes may be substituted with Ru, and would be capable of making that substitution based on the methodology disclosed here.

In this specification and in the claims that follow, reference will be made to a number of terms, which shall be defined to have the following meanings:

The terms "compounds of Formula I" and "compounds of the invention" and "metalloinsertor complexes of the present invention" are used interchangeably and all of these terms refer to a complex represented by Formula I as described above and throughout.

Also, as used herein, unless otherwise indicated, the term "rhodium complex" refers to a complex of Formula I, and is not limited to complexes of Formula I in which M is Rh, but rather also includes complexes of Formula I in which M is Ru.

The term "chrysi" refers to bidentate ligand 5,6-chrysene quinone diimine.

The term "phzi" refers to benzo[a]phenazine-5,6-quinonediimine. The term "phzi complex" or "phzi" to denote a complex, refers to a rhodium (or ruthenium) complex having a phzi ligand.

The term "DPAE" refers to 2-(di(pyridin-2-yl)amino)ethanol. The term "DPAE complex" or "DPAE" to denote a complex, refers to a rhodium (or ruthenium) complex having a DPAE ligand.

The term "HDPA" refers to 2,2'dipyridylamine. The term "HDPA complex" or "HDPA" to denote a complex, refers to a rhodium (or ruthenium) complex having a HDPA ligand.

The term "MeDPA" refers to N-methyl-N-(pyridin-2-yl)pyridin-2-amine. The term "MeDPA complex" or "MeDPA" to denote a complex, refers to a rhodium (or ruthenium) complex having a MeDPA ligand.

The term "EtDPA" refers to N-ethyl-N-(pyridin-2-yl)pyridin-2-amine. The term "EtDPA complex" or "EtDPA" to denote a complex, refers to a rhodium (or ruthenium) complex having a EtDPA ligand.

The terms "PropylDPA" and "PrDPA" refer to N-propyl-N-(pyridin-2-yl)pyridin-2-amine. The terms "PrDPA complex" or "PrDPA" to denote a complex, refers to a rhodium (or ruthenium) complex having a PrDPA ligand.

The term "HexylDPA" refers to N-hexyl-N-(pyridin-2-yl)pyridin-2-amine. The term "HexylDPA complex" or "HexylDPA" to denote a complex, refers to a rhodium (or ruthenium) complex having a HexylDPA ligand.

The term "DPK" refers to di(2-pyridyl)ketone. The term "DPK complex" or "DPK" to denote a complex, refers to a rhodium (or ruthenium) complex having a DPK ligand.

The term "DPE" refers to 1,1-di(pyridin-2-yl)ethanol. The term "DPE complex" or "DPE" to denote a complex, refers to a rhodium (or ruthenium) complex having a DPE ligand.

The term "bpy" refers to 2,2'-bipyridine. The term "bpy complex" or "bpy" to denote a complex, refers to a rhodium (or ruthenium) complex having a bpy ligand.

The term "phen" refers to 1,10-phenanthroline. The term "phen complex" or "phen" to denote a complex, refers to a rhodium (or ruthenium) complex having a phen ligand.

The term "DIP" refers to 4,7-diphenyl-1,10-phenanthroline. The term "DIP complex" or "DIP" to denote a complex, refers to a rhodium (or ruthenium) complex having a DIP ligand.

The term "PyPrOH" refers to 2-(pyridin-2-yl)propano-2-ol. The term "PyPrOH complex," "PyPrO complex", "PyPrOH" or "PyPrO" to denote a complex, refers to a rhodium (or ruthenium) complex having a PyPrO ligand. Those having ordinary skill in the art understand that PyPrO represents the unprotonated ligand as it is when it is bound to Rh or Ru of the Rh or Ru complex, and PyPrOH represents the protonated ligand as it is when it is not bound to Rh or Ru of the Rh or Ru complex.

The term "PPE" refers to 1-phenyl-1-(pyridin-2-yl)ethanol. The term "PPE complex" or "PPE" to denote a complex, refers to a rhodium (or ruthenium) complex having a PPE ligand.

The term "rac" refers to racemic mixtures of delta and lambda enantiomers.

Embodiments of the present invention are directed to rhodium (Rh) and ruthenium (Ru) metalloinsertor complexes that target DNA mismatch and selectively induce cytotoxicity. In some embodiments of the present invention, methods for identifying DNA mismatch include the use of a metalloinsertor complex as described herein. Other methods of the present invention include using a metalloinsertor complex as described herein for selectively inducing cytotoxicity. Still other methods of the present invention include using a metalloinsertor complex as described herein for selectively decreasing cell proliferation.

In some embodiments of the present invention, a metalloinsertor complex that targets DNA mismatch is represented by Formula I.

$$M^{m+}(L_1)(L_2)(L_3)(L_4)(L_5) \quad \text{Formula I}$$

In Formula I, M is rhodium or ruthenium, and m is 2 or 3. $L_1$ is benzo[a]phenazine-5,6-diimine (phzi) or chrysene-5,6-diimine (chrysi), as depicted below.

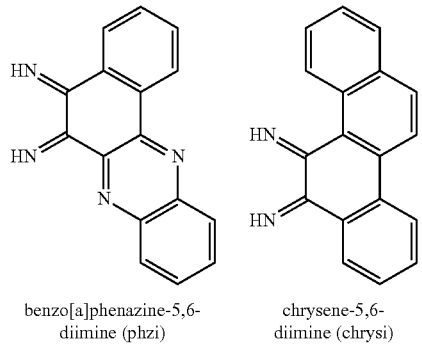

benzo[a]phenazine-5,6-diimine (phzi)     chrysene-5,6-diimine (chrysi)

In Formula I, each of $L_2$ through $L_5$ is either $NH_3$ or combines with an adjacent one of $L_2$ through $L_5$ to form a single ligand with two coordination sites to M, where the single ligand with two coordination sites to M is selected from:

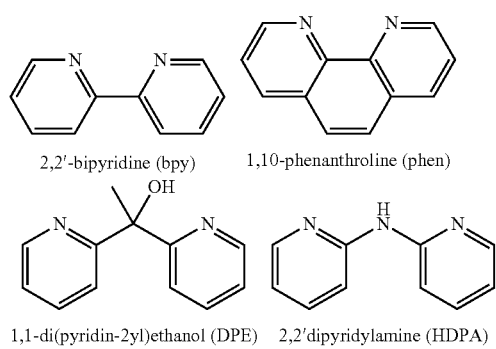

2,2'-bipyridine (bpy)     1,10-phenanthroline (phen)

1,1-di(pyridin-2yl)ethanol (DPE)     2,2'dipyridylamine (HDPA)

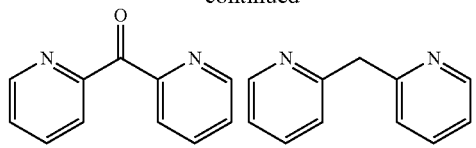

di(2-pyridyl)ketone (DPK)

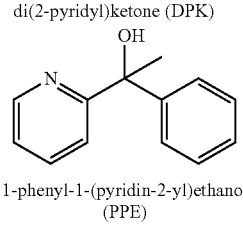 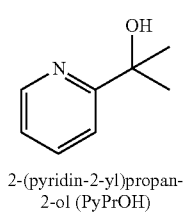

1-phenyl-1-(pyridin-2-yl)ethanol (PPE)     2-(pyridin-2-yl)propan-2-ol (PyPrOH)

Formula II

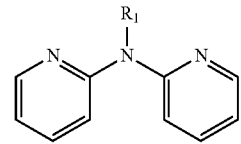

(e.g., MeDPA, EtDPA, PrDPA, HexDPA, DPAE)

Formula III

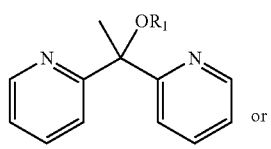 or

Formula IV

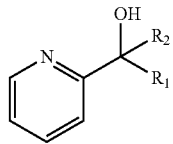

In Formula II, Formula III, and Formula IV, $R_1$ and $R_2$ are each independently selected from alkyl groups terminating in one selected from $CH_3$, OH, SH, $NH_2$, COOH, $N_3$, or alkynyl-linked peptide moieties, or PEGylated groups terminating in one selected from $CH_3$, OH, SH, $NH_2$, COOH, $N_3$, or alkynyl-linked peptide moieties.

Non-limiting examples of specific alkyl derivatives of Formula II, include ligands represented by the following Formula II(a).

Formula II(a)

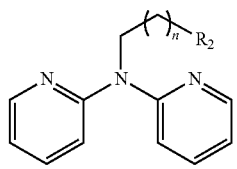

In Formula II(a), as shown, II(a)-$R_2$ is $CH_3$, OH, SH, $NH_2$, COOH, $N_3$, or an alkynyl-linked peptide; and n is any number from 1 to 10. Non-limiting examples of ligands satisfying Formula II(a) include MeDPA, EtDPA, PrDPA, HexDPA, and DPAE.

Non-limiting examples of PEGylated derivatives of Formula II, include ligands represented by the following Formula II(b).

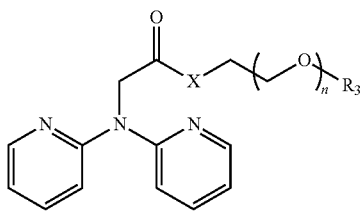

Formula II(b)

In Formula II(b), as shown, X is O or NH; II(b)-$R_3$ is $CH_3$, OH, SH, $NH_2$, COOH, $N_3$, or an alkynyl-linked peptide moiety; and n is any number from 1 to 10.

In some embodiments of the present invention, a complex of Formula I in which any of $L_2$ through $L_5$ is a ligand represented by Formula II(a), Formula II(b), Formula III or Formula IV allows for conjugation of antibodies, carbohydrates or peptides to thereby increase cellular accumulation, specificity and/or biological activity. Indeed, in Formula II (and II(a) and II(b)), Formula III or Formula IV, any of the corresponding $R_1$, $R_2$, and/or $R_3$ moieties can each independently be an alkyl or PEGylated group terminating in an alkynyl-linked peptide moiety. The alkynyl-linked peptide can be any suitable such moiety, e.g. an antibody or carbohydrate.

In some embodiments of the present invention, at least two of $L_2$ through $L_5$ are $NH_3$. In these embodiments, the central M atom is coordinated to at least four ligands. Indeed, when two of $L_2$ through $L_5$ are $NH_3$, the remaining two of $L_2$ through $L_5$ may combine to form a single ligand having two coordination sites to the central M atom. Non-limiting examples of suitable ligands for the single ligand having two coordination sites include those described above, e.g. bpy, phen, DPE, HDPA, DPK, and ligands represented by Formula II.

In other embodiments, all four of $L_2$ through $L_5$ are $NH_3$. In these embodiments, the central M atom is coordinated to five ligands, i.e., the four $NH_3$ ligands and the phzi or chrysi ligand of $L_1$.

In still other embodiments, none of $L_2$ through $L_5$ are $NH_3$, and $L_2$ and $L_3$ combine to form a first single ligand having two coordination sites to the M atom, and $L_4$ and $L_5$ combine to form a second single ligand having two coordination sites to the M atom. In these embodiments, the central M atom is coordinated to three ligands, and each ligand has two coordination sites to the M atom. Also, in these embodiments, the first and second single ligands having two coordination sites to the M atoms may be the same or may be different from each other. Non-limiting examples of suitable ligands for the first and second single ligands, having two coordination sites to the M atom, include those described above with respect to Formulae I and II, e.g., bpy, phen, DPE, HDPA, DPK, PPE, PyPrOH, and ligands represented by Formula II. In some embodiments, for example, both the first and second single ligands can be the same, and can be either HDPA, MeDPA, PrDPA, DPAE, PPE, or PyPrOH. In some alternative examples, however, the first and second single ligands can be different from each other, and each of the first and second ligands can be independently one of DPK, DPE, HDPA, MeDPA, EtDPA, PrDPA, phen, HexDPA, DPAE, PPE, or PyPrOH.

Non-limiting examples of suitable metalloinsertor complexes include $M^{m+}(L_1)(DPE)(NH_3)_2$, $M^{m+}(L_1)(NH_3)_4$, $M^{m+}(L_1)(HDPA)_2$, $M^{m+}(L_1)(MeDPA)_2$, $M^{m+}(L_1)(MDPA)_2$(phen), $M^{m+}(L_1)(PrDPA)_2$(phen), $M^{m+}(L_1)(HexDPA)_2$(phen), $M^{m+}(L_1)(PrDPA)_2$, $M^{m+}(L_1)(DPAE)_2$, $M^{m+}(L_1)$(HDPA)(phen), $M^{m+}(L_1)(DPE)(phen)$, $M^{m+}(L_1)(phen)$(PPE), or $M^{m+}(L_1)(phen)(PyPrOH)$. In these examples, M and m are as described above, i.e., M is either Rh or Ru, and m is 2 or 3. Also, $L_1$ is as described above, i.e., $L_1$ is either chrysi or phzi. Non-limiting examples of suitable metalloinsertor complexes satisfying these formulae include $M^{m+}$(DPK)$(NH_3)_2$(chrysi), $M^{m+}$(DPE)$(NH_3)_2$(chrysi), $M^{m+}$$(NH_3)_4$(phzi), $M^{m+}(HDPA)_2$(phzi), $M^{m+}(HDPA)_2$(chrysi), $M^{m+}(MeDPA)_2$(phzi), $M^{m+}(MeDPA)_2$(chrysi), $M^{m+}$(MeDPA)(phen)(chrysi), $M^{m+}$(EtDPA)(phen)(chrysi), $M^{m+}$(PrDPA)(phen)(chrysi), $M^{m+}$(HexDPA)(phen)(chrysi), $M^{m+}$$(PrDPA)_2$(chrysi), $M^{m+}(DPAE)_2$(chrysi), $M^{m+}$(HDPA)(phen)chrysi), $M^{m+}$(DPE)(phen)(chrysi), $M^{m+}$(chrysi)(phen)(PPE), or $M^{m+}$(chrysi)(phen)(PyPrOH). In these examples, M is Rh or Ru, and m is 2 or 3.

Figure 28:
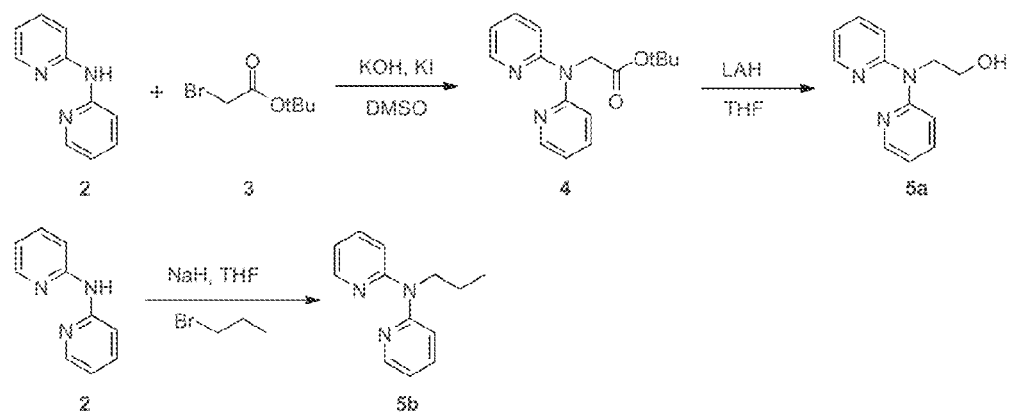
FIG. 28 is a schematic of the synthesis of DPAE (5a) and PrDPA (5b) from dipyridylamine (2), according to embodiments of the present invention.
Figure 29:
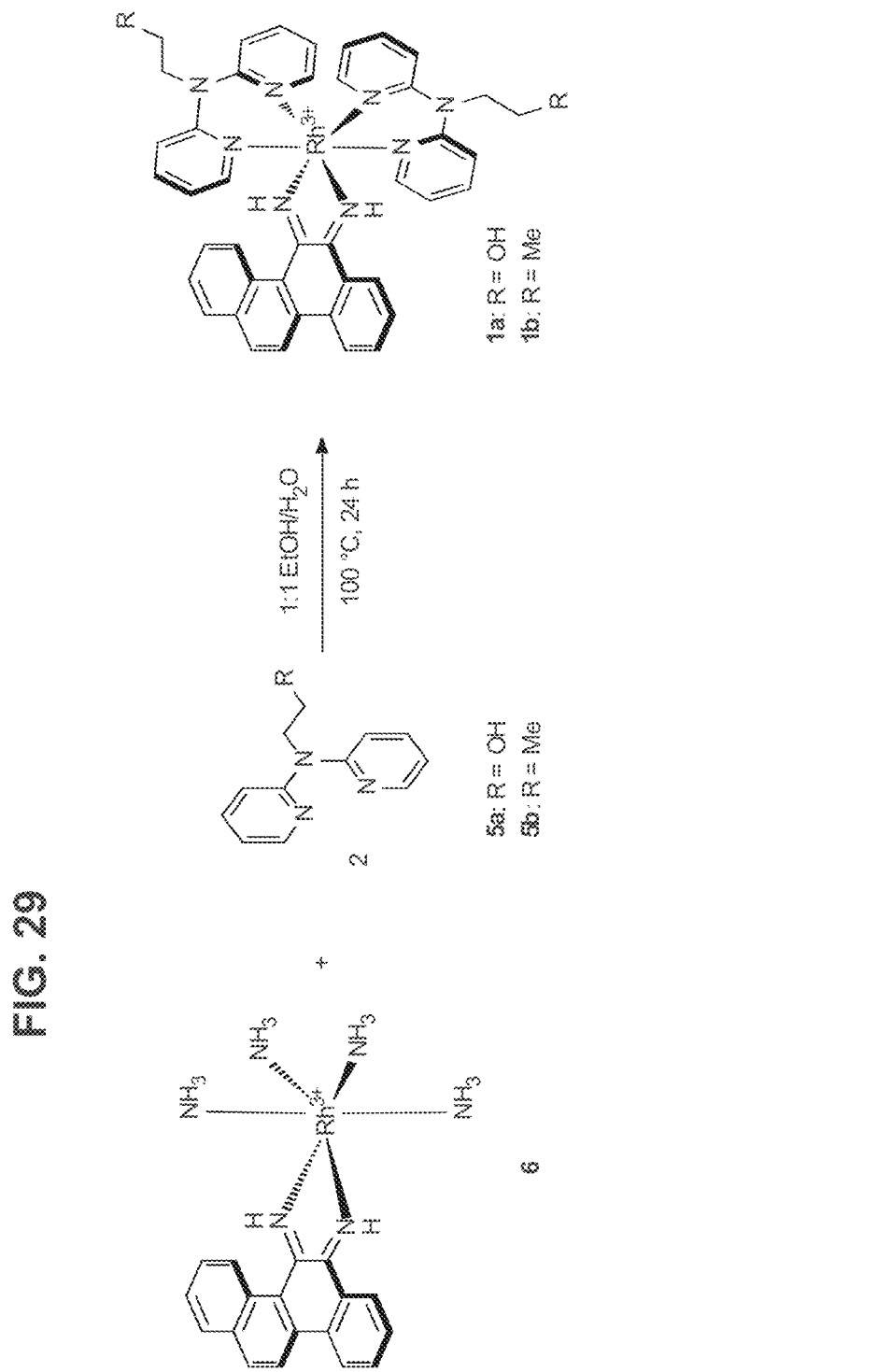
FIG. 29 is a schematic of the synthesis of rac-[Rh(DPAE)$_2$(chrysi)]$^{3+}$ (1a) and rac-[Rh(PrDPA)$_2$(chrysi)]$^{3+}$(1b), according to embodiments of the present invention.

Non-limiting examples of suitable rhodium metalloinsertor complexes are shown in FIGS. 1A through 1N, 1P and 1Q. Some non-limiting examples of metalloinsertor complexes include $[Rh(DPK)(NH_3)_2chrysi]^{3+}$, $[Rh(DPE)(NH_3)_2chrysi]^{2+}$, $[Rh(NH_3)_4phzi]^{3+}$, $[Rh(HDPA)_2phzi]^{3+}$, $[Rh(HDPA)_2chrysi]^{3+}$, $[Rh(MeDPA)_2phzi]^{3+}$, $[Rh(MeDPA)_2chrysi]^{3+}$, $[Rh(chrysi)(phen)(MeDPA)]^{3+}$, $[Rh(chrysi)(phen)(EtDPA)]^{3+}$, $[Rh(chrysi)(phen)(PrDPA)]^{3+}$, $[Rh(phen)(hexylDPA)chrysi]^{3+}$, $[Rh(PrDPA)_2(chrysi)]^{3+}$, $[Rh(DPAE)_2(chrysi)]^{3+}$, $[Rh(chrysi)(phen)(HDPA)]^{3+}$, $[Rh(chrysi)(phen)(DPE)]^{2+}$, $[Rh(chrysi)(phen)(PPE)]^{2+}$, or $[Rh(chrysi)(phen)(PyPrOH)]^{2+}$. Synthesis of each complex is described below. General syntheses for $[Rh(DPAE)_2chrysi]^{3+}$ and $[Rh(PrDPA)_2chrysi]^{3+}$ are shown in FIGS. 28 and 29. General syntheses for $[Rh(chrysi)(phen)(PyPrOH)]^{2+}$ and $[Rh(chrysi)(phen)(PPE)]^{2+}$ are shown in FIGS. 43A and 43B, respectively.

The metalloinsertor complexes of Formula I as described herein, accelerate cellular uptake compared to other metalloinsertor complexes, and therefore trigger a selective cytotoxic effect as a function of mismatch repair (MMR) status. Accordingly, the metalloinsertor complexes are not only useful for indicating the presence of polynucleotide damage or error, and diagnosing conditions characterized by polynucleotide damage or error, but are also useful for inducing selective cytotoxicity in cells characterized by polynucleotide damage or error such as cancer cells.

Figure 40:
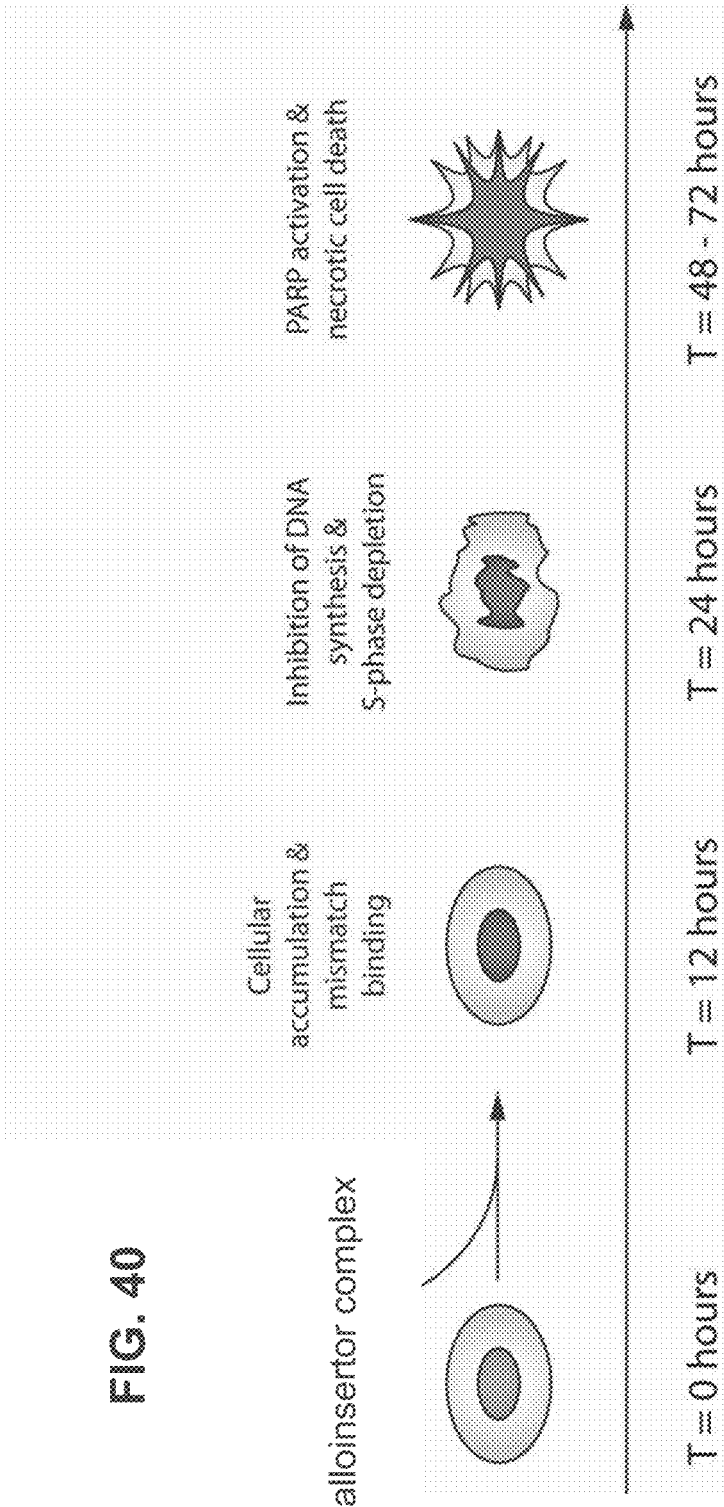
FIG. 40 is a schematic showing a cellular response to metalloinsertor complexes, according to embodiments of the present invention.
Figure 41:
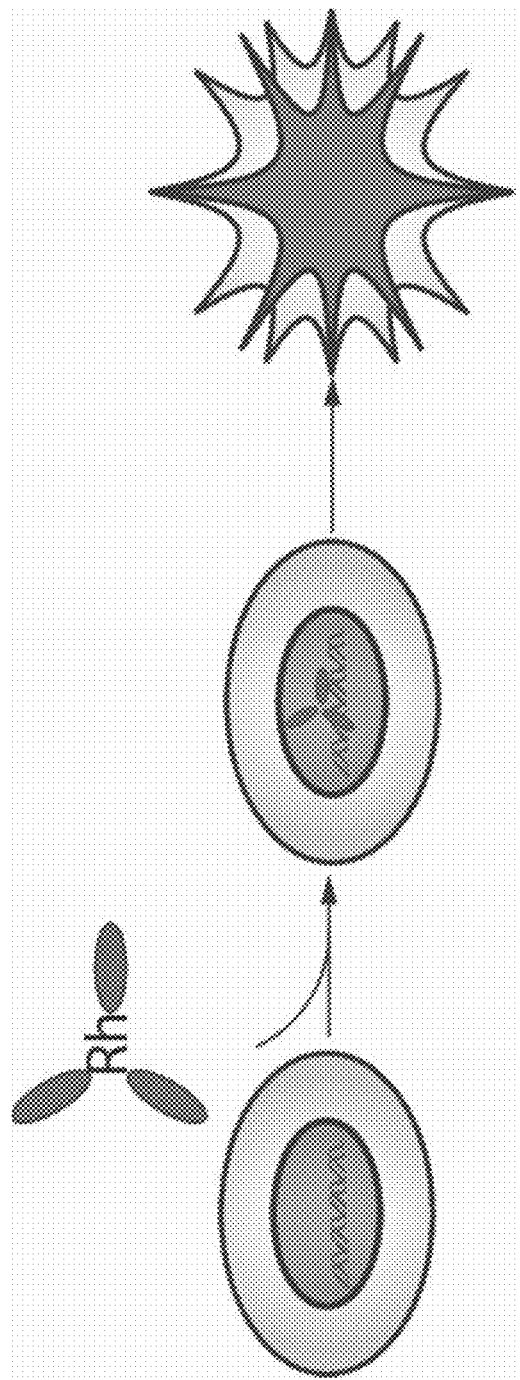
FIG. 41 is a schematic showing cell death in response to incorporation of a metalloinsertor complex, according to embodiments of the present invention.
Figure 42:
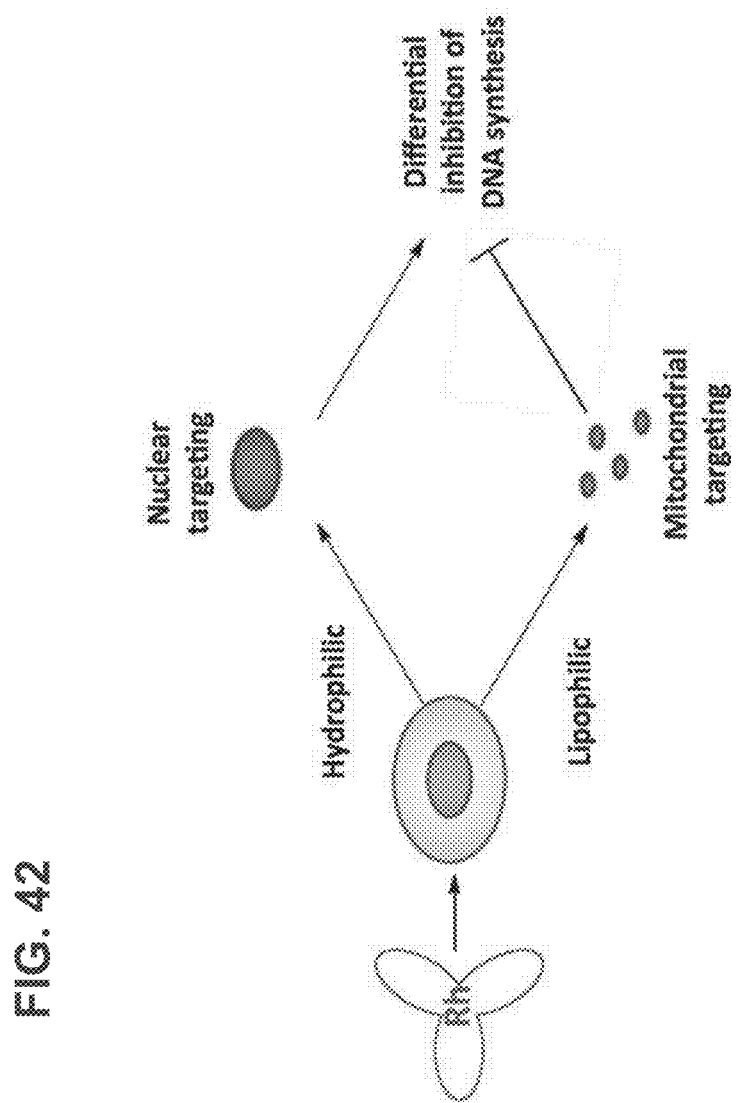
FIG. 42 is a schematic showing subcellular localization in response to the hydrophilic or lipophilic character of the ancillary ligand of a metalloinsertor complex, according to embodiments of the present invention.
Figure 44:
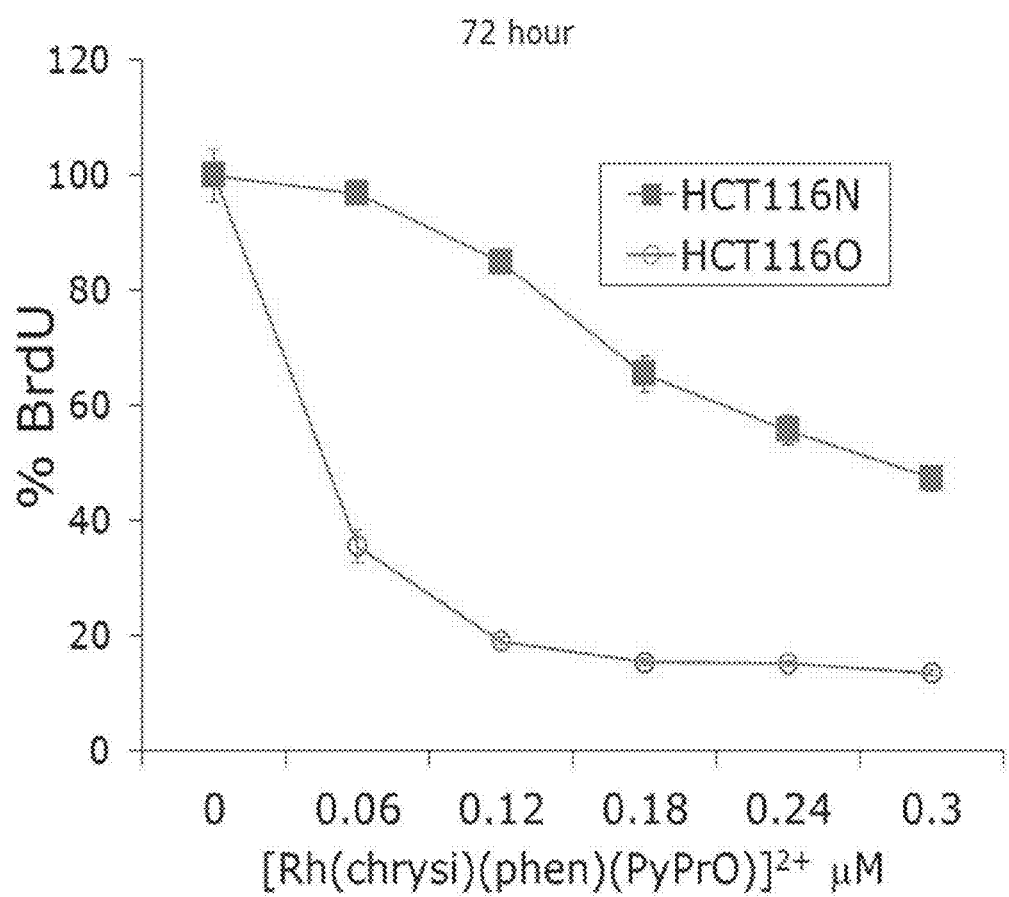
FIG. 44 is a graph of the amount (%) of BrdU incorporation as a function of [Rh(chrysi)(phen)(PyPrO)]$^{2+}$ concentration in the HCT116N (squares) and the HCT116O (circles) cell lines after a 72 hour incubation, according to embodiments of the present invention.
Figure 45:
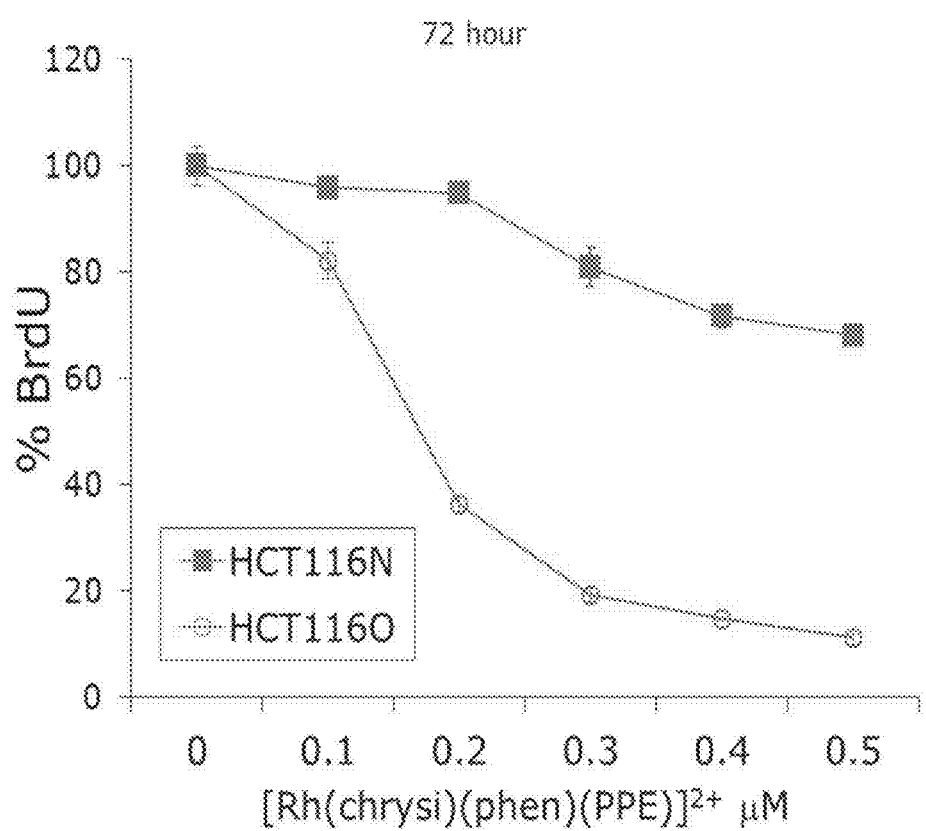
FIG. 45 is a graph of the amount (%) of BrdU incorporation as a function of [Rh(chrysi)(phen)(PPE)]$^{2+}$ concentration in the HCT116N (squares) and the HCT116O (circles) cell lines after a 72 hour incubation, according to embodiments of the present invention.

In some embodiments of present invention, a method of selectively inducing cytotoxicity in an MMR-deficient cell includes providing a metalloinsertor complex of Formula I to an MMR-deficient cell. FIGS. 40-42 are schematics showing the mechanism of action for cytotoxicity and subcellular localization of metalloinsertor complexes of Formula I according to the present invention.

The metalloinsertor complexes according to embodiments of the present invention, selectively decrease cell proliferation. As such, a method for selectively decreasing cell proliferation in MMR-deficient cells includes providing a metalloinsertor complex of Formula I to the MMR-deficient cells. This method of selectively decreasing cell proliferation may be in vitro or in vivo. For example, decreasing cell proliferation in vitro includes growing an MMR-deficient cell in the presence of a metalloinsertor complex of Formula I. Cell culture conditions suitable for the selected MMR-deficient cell line are disclosed in the art and below. For another example, decreasing cell proliferation in vivo includes providing or administering a metalloinsertor complex of Formula I to an animal or human.

In other embodiments of the present invention, metalloinsertor complexes of Formula I selectively induce cytotoxicity in MMR-deficient cells. A method for selectively inducing cytotoxicity includes providing a metalloinsertor complex of Formula I to MMR-deficient cells. This method of selectively inducing cytotoxicity may be in vitro or in vivo. For example, selectively inducing cytotoxicity in vitro includes growing an MMR-deficient cell in the presence of a metalloinsertor complex of Formula I. In another example, selectively inducing cytotoxicity in vivo includes providing or administering a metalloinsertor complex of Formula I to an animal or human.

In some embodiments of the present invention, a complex of Formula I may be administered orally or parenterally, for example by injection, inhalation, transdermally, and the like, and may be administered in vivo or ex vivo. For example, one can use compounds of the invention to purge bone marrow of tumor cells prior to reintroducing the marrow into a patient (e.g., after radiotherapy). The compounds can be administered systemically or locally, for example via indwelling catheter, controlled- or sustained-release implant, minipump, and the like. Alternatively, the compounds can be formulated as an aerosol, and administered to the lungs and trachea.

The compounds can be formulated in a liquid dosage form such as, for example, liquids, suspensions or the like, preferably in unit dosage forms suitable for single administration of precise dosages. Liquid dosages may be administered by injection or infusion, as nose drops or as an aerosol. Alternatively, the active compound can be prepared as a cream or an ointment composition and applied topically. As another alternative, delivery may occur by controlled release of these agents by encapsulation either in bulk or at a microscopic level using synthetic polymers, such as silicone, and natural polymers such as gelatin and cellulose. The release rate can be controlled by proper choice of the polymeric system used to control the diffusion rate (Langer, R. S, and Peppas, N. A., Biomaterials (1981) 2:201). Natural polymers, such as gelatin and cellulose slowly dissolve in a matter of minutes to hours while silicone remains intact for a period of months. The compositions will include a conventional pharmaceutical carrier or excipient, in addition to one or more of the active compound(s). In addition, the compositions may include other medicinal agents, pharmaceutical agents, carriers, adjuvants, etc.

The amount of compound administered will of course, be dependent on the subject being treated, the severity of the affliction, the manner of administration, the frequency of administration, and the judgment of the prescribing physician. Suitable concentrations to determine the "effective amount" can be determined by one of ordinary skill in the art, using only routine experimentation. The frequency of administration is desirably in the range of an hourly dose to a monthly dose, preferably from 8 times/day to once every other day, more preferably 1 to 3 times per day. Ointments containing one or more active compounds and optional pharmaceutical adjuvants in a carrier, such as, for example, water, saline, aqueous dextrose, glycerol, ethanol, and the like, can be prepared using a base such as, for example, petroleum jelly, lard, or lanolin.

Liquified pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. The preparation can additionally contain compounds that facilitate entry of the nucleic acid of interest into the inner ear cells such as Lipofectin, permeability-enhancing agents (e.g., detergents), or other transformation-enhancing agents. Actual methods of preparing such dosage forms are known, or will be apparent, to those skilled in this art; for example, see Remington's Pharmaceutical Sciences, Mack Publishing Co., Easton, Pa., 15th Ed., 1975. The composition or formulation to be administered will, in any event, contain a quantity of one or more of the active compound(s) in an amount effective to alleviate the symptoms of the subject being treated.

For aerosol administration, the active ingredient is preferably supplied in finely divided form along with a surfactant and a propellant. Typical percentages of active ingredients are 0.001 to 2% by weight, preferably 0.004 to 0.10%.

Surfactants must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, eleostearic and oleic acids with an aliphatic polyhydric alcohol or its cyclic anhydride such as, for example, ethylene glycol, glycerol, erythritol, arabitol, mannitol, sorbitol, and hexitol anhydrides derived from sorbitol (the sorbitan esters sold under the trademark "Spans") and the polyoxyethylene and polyoxypropylene derivatives of these esters. Mixed esters, such as mixed or natural glycerides, may be employed. The preferred surface-active agents are the oleates orbita, e.g., those sold under the trademarks "Arlacel C" (sorbitan sesquioleate), "Span 80" (sorbitan monoleate) and "Span 85" (sorbitan trioleate). The surfactant may constitute 0.1=20% by weight of the composition, preferably 0.25-5%.

The balance of the composition is ordinarily propellant. Liquefied propellants are typically gases at ambient conditions, and are condensed under pressure. Among suitable liquefied propellants are the lower alkanes containing up to five carbons, such as butane and propane; fluorinated or fluorochlorinated alkanes, such as are sold under the trademark "Freon". Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

The following Examples are presented for illustrative purposes only, and do not limit the scope or content of the present application.

EXAMPLES

The entire contents of Ernst et al., 2011, *Biochemistry*, 50, 10919-10928 are incorporated herein by reference. In the below examples, the following materials are used, unless otherwise indicated.

$RhCl_3$ was purchased from Pressure Chemical, Inc. (Pittsburgh, Pa.). $[Rh(NH_3)_5Cl]Cl_2$ was obtained from Strem Chemical, Inc. (Newburyport, Mass.). 2,2'-dipyridylamine (HDPA) and Sephadex ion exchange resin were obtained from Sigma-Aldrich (St. Louis, Mo.). Sep-Pak $C_{18}$ solid phase extraction cartridges were purchased from Waters Chemical Co. (Milford, Mass.). Media and supplements were purchased from Invitrogen (Carlsbad, Calif.). The 3-[4,5-dimethylthiazol-2-yl]-2,5-diphenyl tetrazolium bromide (MTT) labeling reagent and acidified lysis buffer (10% SDS in 10 mM HCl) were purchased in kit format from Roche Molecular Biochemicals (Mannheim, Germany). Z-VAD-FMK caspase inhibitor was purchased from Promega. All PARP inhibitors were purchased from Santa Cruz Biotechnology, Inc. All commercial materials were used as received.

Example 1

Synthesis of Tert-butyl 2-(di(pyridine-2-yl)amino)acetate (DPA)

Tert-butyl 2-(di(pyridine-2-yl)amino)acetate was prepared with modification to Kirin et al., 2007, *J. Inorg. Chem.*, 3686-3694, the entire contents of which are incorporated herein by reference. Potassium hydroxide (3.0 g, 53.6 mmol, 4.6 equiv) was added to a solution of 2,2'-dipyridylamine (2.0 g, 11.7 mmol) in 40 ml DMSO and stirred at room temperature for 16 hours (h). Potassium iodide (200 mg, 1.2 mmol, 0.1 equiv) and tert-butyl bromoacetate (4 ml, 2.3 equiv) were added to the mixture, and the reaction was stirred for 2 h at room temperature. The reaction mixture was extracted with diethyl ether (3×50 ml). The organic fractions were combined and dried over magnesium sulfate, and the solvent was removed by rotary evaporation. The crude product was isolated by flash chromatography ($SiO_2$, hexane/ethyl acetate=8:2) to give a yellow oil. DPA was obtained (Yield: 2.92 g (88%)), and confirmed by $^1$H NMR ($CDCl_3$, 300 MHz): δ 8.33 (ddd, J=5.0, 1.9, 0.9 Hz; 2H), 7.53 (m, 2H), 7.23 (m, 2H), 6.88 (ddd, J=7.2, 5.0, 0.9 Hz; 2H), 4.84 (s, 2H), 1.42 (s, 9H). ESI-MS (cation): 286 m/z (M+H$^+$) obsd, 286 m/z calcd.

Example 2

Synthesis of 2-(di(pyridine-2-yl)amino)ethanol

To a slurry of LAH (lithium aluminum hydride) (1.17 g, 30.8 mmol, 3.0 equiv) in THF (tetrahydrofuran) (45 ml) was added Tert-butyl 2-(di(pyridine-2-yl)amino)acetate (2.9 g, 10.2 mmol) at 0° C. under 1 atm argon (Ar). The reaction was slowly warmed to room temperature over 4 h. The reaction mixture was then diluted with diethyl ether and cooled to 0° C. The reaction was quenched via careful addition of water (4.0 ml) and then dried with magnesium sulfate. The solvent was removed in vacuo, and the crude product was purified by flash chromatography ($SiO_2$, hexane/ethyl acetate=1:1) to afford DPAE as a pale yellow oil. DPAE was obtained (Yield: 1.2 g (55%)), and confirmed by $^1$H NMR (DMSO-$d_6$, 300 MHz): δ 8.27 (m, 2H), 7.62 (m, 2H), 7.16 (d, J=8.4 Hz, 2H), 6.93 (m, 2H), 4.92 (t, J=5.4 Hz, 1H), 4.16 (t, J=6.5 Hz, 2H), 3.58 (q, J=6.5 Hz, 2H). ESI-MS (cation): 216.1 m/z (M+H$^+$) obsd, 215 m/z calcd.

Example 3

Synthesis of 1,1-di-2-pyridylethanol

DPE was prepared according to Basu et al., 1987, *Journal of the Chem. Soc, Chemical Comm.* 22, 1724-1725, the entire contents of which are incorporated herein by reference.

Example 4

Synthesis of N-alkyl-N-(pyridin-2-yl)pyridin-2-amine (MeDPA), EtDPA, PropylDPA, HexylDPA): To a slurry of sodium hydride (70 mg, 2.9 mmol) in THF (10 ml) was added HDPA (500 mg, 2.9 mmol) in 5 ml THF at 0° C. under 1 atm Ar. The reaction was purged with argon for 15 min, and the appropriate 1-bromomethane (3.8 mmol) was added dropwise and warmed to room temperature. The reaction was stirred an additional 18 h under argon at reflux temperature. The reaction mixture was extracted with dilute sodium bicarbonate, and the aqueous phase was extracted with $CH_2Cl_2$ (3×40 ml). The organic fractions were combined and dried over magnesium sulfate, and the solvent was removed in vacuo. MethylDPA was obtained (10 mmol scale, Yield: 0.44 g, 23%), and confirmed by $^1$H-NMR ($CDCl_3$): 8.35 (d of d, 2H); 7.54 (t, 2H); 7.17 (d, 2H); 6.86 (t, 2H), 3.62 (s, 3H). ESI-MS: 186 m/z [M+H]$^+$.

Example 5

Synthesis of N-ethyl-N-(pyridin-2-yl)pyridin-2-amine (EtDPA). EtDPA was synthesized as described in Example 4, except that 1-bromoethane was used instead of 1-bromomethane. EthylDPA was obtained (1 mmol scale, Yield: 65.5 mg, 32%), and confirmed by $^1$H-NMR ($CDCl_3$): δ 8.39-8.26 (m, 2H), 7.56-7.40 (m, 2H), 7.06 (dd, J=8.4, 0.4 Hz, 2H), 6.87-6.76 (m, 2H), 4.23 (q, J=7.0 Hz, 2H), 1.30-1.12 (m, 5H).

Example 6

Synthesis of N-propyl-N-(pyridin-2-yl)pyridin-2-amine (PrDPA). PrDPA was synthesized as described in Example 4, except that 1-bromopropane was used instead of 1-bromomethane. PropylDPA was obtained (10 mmol scale, Yield: 0.76 g, 36%), and confirmed by $^1$H NMR (300 MHz, $cdcl_3$) δ 8.39-8.20 (m, 2H), 7.59-7.40 (m, 2H), 7.05 (dd, J=8.4, 0.8 Hz, 2H), 6.81 (ddd, J=6.7, 5.4, 0.8 Hz, 2H), 4.16-4.01 (m, 2H), 1.78-1.59 (m, 2H), 0.91 (t, J=7.4 Hz, 3H).

Example 7

Synthesis of N-hexyl-N-(pyridin-2-yl)pyridin-2-amine (HexylDPA). HexylDPA was synthesized as described in Example 4, except that 1-bromohexane was used instead of 1-bromomethane. HexylDPA was obtained (10 mmol scale, Yield: 0.46 g, 18%), and confirmed by $^1$H NMR (300 MHz, $cdcl_3$) δ 8.35-8.25 (m, 2H), 7.55-7.41 (m, 2H), 7.05 (d, J=8.4 Hz, 2H), 6.81 (dd, J=7.1, 5.0 Hz, 2H), 4.23-4.03 (m, 2H), 1.63 (m, 2H), 1.25 (m, 6H), 0.83 (t, 3H).

Example 8

Synthesis of 2-(pyridin-2-yl)propan-2-ol (PyPrOH) and 1-phenyl-1-(pyridin-2-yl)ethanol (PPE)

The appropriate ketone Py(CO)(L) (8.3 mmol) was dissolved in dry diethyl ether (100 mL) in an oven-dried 250 mL schlenk flask. This was cooled to −78° C. and MeLi (12.9 mL of a 1.6M solution) was added slowly over 15 minutes. The resulting yellow solution was stirred at −78° C. for 1 hour, and was then warmed to ambient temperature. Next, saturated $NH_4Cl$ (aq) (30 mL) was added to quench the reaction, and the resulting solution was extracted with EtOAc (3×75 mL), dried over $Na_2SO_4$, and the solvent evaporated in vacuo. The crude product was purified via flash chromatography ($SiO_2$, 1:1 $EtOAc:CH_2Cl_2$ for L=Me, 1:3 $EtOAc:CH_2Cl_2$ for L=Ph) to yield a light yellow oil. PyPrOH was obtained (yield: 55%). PyPrOH: $^1$H NMR NMR ($CDCl_3$, 300 MHz): δ 8.52 (d of m, J=4.8 Hz, 1H); 7.71 (t of m, J=7.8 Hz, 1H); 7.38 (d of m, J=8.1 Hz, 1H); 7.21 (t of m, J=6.2 Hz, 1H); 5.08 (s, 1H); 1.54 (s, 6H). PPE was obtained (yield: 97%). $^1$H NMR (CDCl$_3$, 300 MHz): δ 8.52 (d of m, J=5.1 Hz, 1H); 7.65 (t of d, J=7.8 Hz, 1.8 Hz, 1H); 7.48 (m, 2H); 7.31 (m, 3H); 7.17-7.26 (m, 2H); 5.85 (s, 1H); 1.94 (s, 3H).

Example 9

Synthesis of [Rh(DPK)(NH$_3$)$_2$chrysi]$^{3+}$

A 100-mL round-bottomed flask was charged with [Rh(NH$_3$)$_4$chrysi]Cl$_3$ (15.0 mg, 27.7 μmol) and DPK (7.7 mg, 41.6 μmol), as described in Muerner et al., 1998, *Inorg. Chem.* 37, 3007-3012, the entire contents of which are incorporated herein by reference. Ethanol (30 mL) was added and the resulting red solution was stirred at 60° C. for 16 hours. The solvent was evaporated in vacuo and the resulting red solid purified via column chromatography (C$_{18}$-derivatized silica, eluting with 10% acetonitrile in 0.1% TFA$_{(aq)}$). The fractions containing product were identified by HPLC, combined, and lyophilized. The chloride salt can be obtained from a Sephadex QAE anion exchange column equilibrated with 0.1M MgCl$_2$. [Rh(NH$_3$)$_4$chrysi]Cl$_3$ was obtained (Yield: 9 mg, 35%). and confirmed by ESI-MS: calc. 575.1 (M−2H$^+$), obs. 574.8 (M−2H$^+$), 288.6 (M−H$^{2+}$).

As would be understood by those of ordinary skill in the art, the corresponding ruthenium complex, [Ru(DPK)(NH$_3$)$_2$chrysi]$^{2+}$, can be made by the same process by substituting the [Rh(NH$_3$)$_4$chrysi]Cl$_3$ with [Ru(NH$_3$)$_4$chrysi]Cl$_2$.

Example 10

Synthesis of [Rh(chrysi)(DPE)(NH$_3$)]$_2$Cl$_3$

A 250 mL round-bottomed flask was charged with [Rh(chrysi)(NH$_3$)$_4$]TFA$_3$ (25 mg, 0.059 mmol) and 1,1-di(pyridin-2-yl)ethanol (36.5 mg. 0.182 mmol) in ethanol (50 mL) to give a red solution. The reaction was heated to reflux (80° C.) and stirred for 5 days. The ethanol solution was evaporated to dryness and dissolved in 0.1% TFA$_{(aq)}$ (100 mL). The red solution was loaded onto a solid phase extraction (SPE) cartridge and rinsed with copious amount of 0.1% TFA$_{(aq)}$. The SPE cartridge was eluted with 10% acetonitrile in 0.1% TFA$_{(aq)}$ and fractions were collected. The fractions containing product were identified by HPLC, combined, and lyophilized. The chloride salt can be obtained from a Sephadex QAE anion exchange column equilibrated with 0.1M MgCl$_2$. [Rh(chrysi)(DPE)(NH$_3$)$_2$]Cl$_3$ was obtained (Yield: 18 mg, 43%), and confirmed by ESI-MS: calc. 591.49 (M−2H$^+$), obs. 591.1 (M−2H$^+$).

As would be understood by those of ordinary skill in the art, the corresponding ruthenium compound, [Ru(chrysi)(DPE)(NH$_3$)$_2$]Cl$_2$, can be made by the same process by substituting the [Rh(chrysi)(NH$_3$)$_4$]TFA$_3$ with [Ru(chrysi)(NH$_3$)$_4$]TFA$_2$.

Example 11

Synthesis of [Rh(MeDPA)$_2$chrysi]Cl$_3$

[Rh(NH$_3$)$_4$chrysi]TFA$_3$ (15 mg, 0.02 mmol) was reacted with MeDPA (22 mg, 0.12 mmol) in a 1:1 mixture of ethanol:water (40 mL). The dark red solution was heated under reflux (95° C.) for 16 hr. Ethanol was removed under vacuum, and the resulting reddish brown solution was filtered to remove any residue. The filtrate was loaded onto a SPE cartridge and eluted with 25% acetonitrile in 0.1% TFA$_{(aq)}$. The resulting reddish solid was further purified via column chromatography (C$_{18}$-derivatized silica, eluting with 12.5% acetonitrile in 0.1% TFA$_{(aq)}$). The fractions containing product were identified by HPLC, combined, and lyophilized to give a red solid. The chloride salt can be obtained from a Sephadex QAE anion exchange column equilibrated with 0.1M MgCl$_2$. [Rh(MeDPA)$_2$chrysi]Cl$_3$ was obtained (Yield: 7.5 mg, 35%), and confirmed by ESI-MS: calc. 727.2 (M−2H$^+$), obs. 727.1 (M−2H$^+$), 364.3 (M−H$^{2+}$). UV-Vis (H$_2$O, pH 7): 295 nm (55,000 M$^{-1}$ cm$^{-1}$), 320 nm (39,700 M$^{-1}$, cm$^{-1}$), 390 nm (14,000 M$^{-1}$, cm$^{-1}$).

As would be understood by those of ordinary skill in the art, the corresponding ruthenium compound, [Ru(MeDPA)$_2$chrysi]Cl$_2$, can be made by the same process by substituting the [Rh(NH$_3$)$_4$chrysi]TFA$_3$ with [Ru(NH$_3$)$_4$chrysi]TFA$_2$.

Example 12

Synthesis of [Rh(NH$_3$)phzi]Cl$_3$

[Rh(NH$_3$)$_6$][OTf]$_3$ (0.50 g, 0.77 mmol) and benzo[a]phenazine-5,6-dione (0.200 g, 0.77 mmol) were dissolved in a 1:5 mixture of water:acetonitrile (500 mL). A 1M solution of NaOH (1 mL) was added to the yellow solution and the reaction was allowed to stir at room temperature for 45 min, at which time a 1M solution of HCl (1 mL) was added to neutralize the reaction mixture. The acetonitrile was evaporated in vacuo and the resulting yellow solution was loaded onto a SPE cartridge, eluted with 25% acetonitrile in 0.1% TFA$_{(aq)}$, and lyophilized to give a yellow solid. The chloride salt can be obtained from a Sephadex QAE anion exchange column equilibrated with 0.1M MgCl$_2$. [Rh(NH$_3$)$_4$phzi]Cl$_3$ was obtained (Yield: 0.45 g, 76%), and confirmed by $^1$H NMR (300 MHz, d$_6$-DMSO): δ 3.79 (s, 6H), 4.48 (d, J=20.1 Hz, 6H), 7.92-8.21 (m, 4H), 8.34 (m, 2H), 8.62 (d, J=7.6 Hz, 1H), 8.96 (d, J=7.8 Hz, 1H), 13.88 (s, 1H), 13.98 (s, 1H). ESI-MS: calc. 524.07 (M−NH$_3$+TFA$^+$), obs. 523.8 (M−NH$_3$+TFA$^+$). UV-Vis (H$_2$O, pH 7): 250 nm (36,800 M$^{-1}$ cm$^{-1}$), 310 nm (20,800 M$^{-1}$, cm$^{-1}$), 340 nm (23,400 M$^{-1}$, cm$^{-1}$).

As would be understood by those of ordinary skill in the art, the corresponding ruthenium compound, [Ru(NH$_3$)$_4$phzi]Cl$_2$, can be made by the same process by substituting the [Rh(NH$_3$)$_6$][OTf]$_3$ with [Ru(NH$_3$)$_6$][OTf]$_2$.

Example 13

Synthesis of [Rh(HDPA)$_2$phzi]Cl$_3$

A solution of [Rh(NH$_3$)$_4$phzi]TFA$_3$ (53.2 mg, 69.2 μmol) in ethanol (25 mL) was added to a 100-mL schlenk flask and sparged with argon for 10 min. A solution of HDPA (0.346 mmol) in ethanol (25 mL) was then added and the resulting light yellow solution sparged with argon for an additional 10 min, then subsequently heated to 90° C. The solution was allowed to stir for 48 hours, after which the solvent was evaporated in vacuo and the resulting red solid purified via column chromatography (C$_{18}$-derivatized silica, eluting with 12.5% acetonitrile in 0.1% TFA$_{(aq)}$. The fractions containing product were identified by HPLC, combined, and lyophilized to give a red solid. The chloride salt can be obtained from a Sephadex QAE anion exchange column equilibrated with 0.1M MgCl$_2$. [Rh(HDPA)$_2$phzi]Cl$_3$ was obtained (Yield: 21.5 mg, 38%), and confirmed by $^1$H NMR (300 MHz, d$_6$-DMSO): δ 7.04 (m, 4H), 7.81 (m, 5H), 7.92 (m, 5H), 8.03 (m, 4H), 8.14 (m, 3H), 8.27 (m, 3H), 8.73 (s, 1H), 9.37 (s, 1H), 12.65 (s, 1H), 13.02 (s, 1H). ESI-MS: calc. 701.16 (M−2H$^+$), obs. 701.1 (M–2H⁺), 351.3 (M–H²⁺). UV-Vis (H₂O, pH 7): 318 nm (44,600 M⁻¹ cm⁻¹), 350 nm (33,200 M⁻¹, cm⁻¹), 400 nm (9,100 M⁻¹, cm⁻¹).

As would be understood by those of ordinary skill in the art, the corresponding ruthenium compounds, [Ru(HDPA)₂phzi]Cl₂ can be made by the same process by substituting the [Rh(NH₃)₄phzi]TFA₃ with [Ru(NH₃)₄phzi]TFA₂.

Example 14

Synthesis of [Rh(MeDPA)₂phzi]Cl₃

[Rh(MeDPA)₂phzi]Cl₃ was synthesized as described in Example 12, except that MeDPA was substituted for HDPA. [Rh(MeDPA)₂phzi]Cl₃ Yield: 18.7 mg, 32%. ¹H NMR (300 MHz, d₆-DMSO): δ 3.87 (s, 3H), 4.06 (s, 3H), 7.24 (m, 5H), 7.67 (m, 3H), 7.73 (m, 3H), 7.97 (m, 5H), 8.11 (m, 4H), 8.28 (m, 4H), 14.37 (s, 1H), 15.16 (s, 1H). ESI-MS: calc. 729.19 (M–2H⁺), obs. 729.2 (M–2H⁺), 544.1 (M–L–2H⁺), 365.4 (M–H²⁺). UV-Vis (H₂O, pH 7): 306 nm (45,000 M⁻¹ cm⁻¹), 340 nm (32,500 M⁻¹, cm⁻¹), 400 nm (10,700 M⁻¹, cm⁻¹).

Example 15

Synthesis of [Rh(chrysi)(phen)(NH₃)₂]Cl₃

Was prepared from [Rh(phen)(NH₃)₄]OTf₃ and 5,6-chrysenequinone following the methods described by Muerner et. al, 1998 (supra).

As would be understood by those of ordinary skill in the art, the corresponding ruthenium compound, [Ru(chrysi)(phen)(NH₃)₂]Cl₂, can be made by the same process by substituting the [Rh(phen)(NH₃)₄]OTf₃ with [Ru(phen)(NH₃)₄]OTf₂.

Example 16

Synthesis of [Rh(chrysi)(phen)(HDPA)]Cl₃

Rh(chrysi)(phen)(NH₃)₂]Cl₃ (25 mg, 0.02 mmol) was reacted with HDPA (0.022 mmol) in a 4:1 mixture of ethanol:water (10 mL). The bright red solution was refluxed overnight. The solvent was removed in vacuo and the product was filtered to remove any residue. The filtrate was concentrated on a SPE cartridge, eluted with 20% acetonitrile in TFA$_{(aq)}$, and lyophilized to give a red solid. Analytically pure material was obtained from reverse phase HPLC and lyophilized to yield a dark red solid. The chloride salt can be obtained from a Sephadex QAE anion exchange column equilibrated with 0.1M MgCl₂. [Rh(chrysi)(phen)(HDPA)]Cl₃ was obtained (Yield: 28%), and confirmed by ESI-MS: calc 708.14 [M–2H⁺], obs. 708.2 (M–2H⁺) UV-Vis (H₂O, pH 7): 303 nm (57000 M⁻¹ cm⁻¹), 391 nm (10,600 M⁻¹, cm⁻¹).

As would be understood by those of ordinary skill in the art, the corresponding ruthenium compound, [Ru(chrysi)(phen)(HDPA)]Cl₂, can be made by the same process by substituting the Rh(chrysi)(phen)(NH₃)₂]Cl₃ with Ru(chrysi)(phen)(NH₃)₂]Cl₂.

Example 17

Synthesis of [Rh(chrysi) (phen) (MeDPA)]Cl₃

[Rh(chrysi)(phen)(MeDPA)]Cl₃ was synthesized as described in Example 15, except that MeDPA was substituted for HDPA. [Rh(chrysi)(phen)(MeDPA)]Cl₃ was obtained (Yield: 32%), and confirmed by ¹H NMR (500 MHz, DMSO-d₆) 12.45 (s, 1H), 10.48 (s, 1H), 9.34-6.83 (m, 26H), 3.87 (s, 3H). ESI-MS: calc. 722.15 (M–2H⁺), obs. 722 (M–2H⁺), 362 (M–H²⁺).

As would be understood by those of ordinary skill in the art, the corresponding ruthenium compound [Ru(chrysi)(phen)(MeDPA)]Cl₂ can be made by the same process by substituting the Rh(chrysi)(phen)(NH₃)₂]Cl₃ with Ru(chrysi)(phen)(NH₃)₂]Cl₂.

Example 18

Synthesis of [Rh(chrysi)(phen)(EtDPA)]

[Rh(chrysi)(phen)(EtDPA)] was synthesized as described in Example 15, except that EtDPA was substituted for HDPA. [Rh(chrysi)(phen)(EtDPA)]Cl₃ was obtained, (Yield: 28%), and confirmed by ESI-MS: calc. 736.17 (M–2H⁺), obs. 736 (M–2H⁺), 369 (M–H²⁺).

As would be understood by those of ordinary skill in the art, the corresponding ruthenium compound [Ru(chrysi)(phen)(EtDPA)]Cl₂ can be made by the same process by substituting the Rh(chrysi)(phen)(NH₃)₂]Cl₃ with Ru(chrysi)(phen)(NH₃)₂]Cl₂.

Example 19

Synthesis of [Rh(chrysi)(phen)(PropylDPA)]C₃

[Rh(chrysi)(phen)(PropylDPA)]Cl₃ was synthesized as described in Example 15, except that PrDPA was substituted for HDPA. [Rh(chrysi)(phen)(PrDPA)]Cl₃ was obtained (Yield: 22%), and confirmed by ESI-MS: calc. 750.18 (M–2H⁺), obs. 750 (M–2H⁺), 376 (M–H²).

As would be understood by those of ordinary skill in the art, the corresponding ruthenium compound [Ru(chrysi)(phen)(PrDPA)]C₂ can be made by the same process by substituting the Rh(chrysi)(phen)(NH₃)₂]Cl₃ with Ru(chrysi)(phen)(NH₃)₂]Cl₂.

Example 20

Synthesis of [Rh(chrysi)(phen)(HexylDPA)]Cl₃

[Rh(chrysi)(phen)(HexylDPA)]Cl₃ was synthesized as described in Example 15, except that hexylDPA was substituted for HDPA. [Rh(chrysi)(phen)(HexylDPA)]Cl₃ was obtained (Yield: 18%), and confirmed by ESI-MS: calc. 792.23 (M–2H⁺), obs. 792 (M–2H⁺), 397 (M–H²⁺).

As would be understood by those of ordinary skill in the art, the corresponding ruthenium compound [Ru(chrysi)(phen)(HexylDPA)]Cl₂ can be made by the same process by substituting the Rh(chrysi)(phen)(NH₃)₂]Cl₃ with Ru(chrysi)(phen)(NH₃)₂]Cl₂.

Example 21

Synthesis of [Rh(chrysi)(phen)(DPE)]Cl₃

A 125 mL round-bottomed flask was charged with [Rh(chrysi)(phen)(NH₃)₂]TFA₃ (62.0 mg, 0.068 mmol) and DPE (25.6 mg, 0.128 mmol) in ethanol (50 mL) to give a red solution. The reaction was heated to reflux (80° C.) and stirred for 48 hours. The ethanol solution was evaporated to dryness and dissolved in 0.1% TFA$_{(aq)}$ (trifluoroacetic acid) (50 mL). The red solution was loaded onto a SPE cartridge and rinsed with copious amount of 0.1% TFA$_{(aq)}$. The SPE cartridge was eluted with 10% acetonitrile in 0.1% TFA$_{(aq)}$ and fractions were collected. The fractions containing product were identified by HPLC, combined, and lyophilized. The chloride salt can be obtained from a Sephadex QAE anion exchange column equilibrated with 0.1M $MgCl_2$. [Rh(chrysi)(phen)(DPE)]$Cl_3$ was obtained (Yield: 17 mg, 29.6%), and confirmed by ESI-MS: calc. 737.15 (M−2H$^+$), obs. 737 (M−2H$^+$), 369 (M−H$^{2+}$). UV-Vis ($H_2O$, pH 7): 272 nm (59800 M$^{-1}$ cm$^{-1}$), 303 nm (18,400 M$^{-1}$, cm$^{-1}$), 440 nm (5,400 M$^{-1}$, cm$^{-1}$).

As would be understood by those of ordinary skill in the art, the corresponding ruthenium compound, [Ru(chrysi)(phen)(DPE)]$Cl_2$, can be made by the same process by substituting the [Rh(chrysi)(phen)($NH_3$)$_2$]$TFA_3$ with [Ru(chrysi)(phen)($NH_3$)$_2$]$TFA_2$.

Example 22

Synthesis of [Rh(DPAE)chrysi]$^{3+}$

[Rh($NH_3$)$_4$chrysi]$C_3$ (20 mg, 0.038 mmol) and DPAE (17.8 mg, 0.082 mmol, excess) were dissolved in a 1:1 mixture of ethanol and water (100 ml) and heated under reflux for 28 h. The solvent was removed in vacuo, and the crude product was purified by HPLC (95:5:0.001 water:acetonitrile:TFA), using a C18 reverse-phase column (Varian, Inc). The purified product was dried under vacuum and redissolved in a minimal volume of water. The TFA counterion was exchanged for a chloride with a Sephadex QAE-125 ion-exchange resin primed with 1M $MgCl_2$. [Rh(chrysi)(phen)(DPE)]$Cl_3$ was obtained (Yield: 4.5 mg (13.5%)), and confirmed by $^1$H NMR (300 MHz, DMSO-d6) δ 13.03 (s, 1H), 9.27 (d, J=8.1 Hz, 1H), 9.02-8.75 (m, 5H), 8.60-8.49 (m, 2H), 8.45-7.60 (m, 31H), 7.52 (d, J=5.8 Hz, 1H), 7.48-7.31 (m, 3H), 7.31-7.09 (m, 4H), 5.34 (s, 2H), 4.97 (s, 3H), 4.67 (s, 2H), 4.48 (s, 3H), 4.32 (s, 1H), 4.11 (s, 1H), 3.82 (s, 2H), 3.61 (s, 5H). UV-vis ($H_2O$ pH 8): 297 nm (47,000 M$^{-1}$ cm$^{-1}$), 391 nm (9,300 M$^{-1}$ cm$^{-1}$). ESI-MS (cation): 787.1 m/z (M−2H$^+$), 394.2 m/z (M−H$^{2+}$) obsd, 787 m/z (M−2H$^+$) calcd.

As would be understood by those of ordinary skill in the art, the corresponding ruthenium complex, [Ru(DPAE)$_2$chrysi]$^2$, can be made by the same process by substituting the [Rh($NH_3$)$_4$chrysi]$Cl_3$ with [Ru($NH_3$)$_4$chrysi]$Cl_2$.

Example 23

Synthesis of [Rh(PrDPAh)$_2$chrysi]$^{3+}$

[Rh(PrDPA)$_2$chrysi]$^{3+}$ was synthesized from [Rh($NH_3$)$_4$chrysi]$Cl_3$ (20 mg. 0.038 mmol) and PropylDPA (17 mg, 0.08 mmol) as described for [Rh(DPAE)$_2$chrysi]$^{3+}$. The resulting product was purified by HPLC 95:5:0.001 $H_2O$:acetonitrile:TFA) and passed through a Sephadex QAE-125 ion-exchanged resin primed with 1M $MgCl_2$ to give the chloride salt. [Rh(PrDPA)$_2$chrysi]$^{3+}$ was obtained (Yield: 3 mg (15%).), and confirmed by $^1$H NMR (300 MHz, DMSO-d6) δ 10.10 (s, 2H), 8.11 (s, 2H), 8.00 (d, J=9.1 Hz, 4H), 7.76 (s, 3H), 7.62 (d, J=8.5 Hz, 13H), 7.36 (d, J=6.6 Hz, 9H), 7.24 (s, 4H), 6.83 (d, J=7.9 Hz, 9H), 1.72 (s, 7H), 1.49 (s, 2H), 1.10 (s, 7H), 0.97-0.84 (m, 6H), 0.62 (t, J=7.2 Hz, 9H), 0.31 (s, 1H), 0.00 (t, J=7.3 Hz, 9H). UV-vis: ($H_2O$ pH 8): 295 nm (51,000 M$^{-1}$ cm$^{-1}$), 388 nm (13,000 M$^{-1}$ cm$^{-1}$). ESI-MS (cation): 783.1 m/z (M−2H$^+$), 392.4 m/z (M−H$^{2+}$) obsd, 783 m/z calcd.

As would be understood by those of ordinary skill in the art, the corresponding ruthenium complex, [Ru(PrDPA)$_2$chrysi]$^{2+}$, can be made by the same process by substituting the [Rh($NH_3$)$_4$chrysi]$Cl_3$ with [Ru($NH_3$)$_4$chrysi]$Cl_2$.

Example 24

Synthesis of [Rh(chrysi)(phen)(PPE)]$^{2+}$ and [Rh(chrysi)(phen)(PyPrO)]$^{2+}$

[Rh(chrysi)(phen)($NH_3$)$_2$]$TFA_3$ (at 62.3 mg, 0.092 mmol) and (PPE or PyPrO) (at 0.138 mmol) were dissolved in 1:12 $H_2O$:EtOH (90 mL). The resulting red solution was heated to 98° C. and refluxed for 18 hours. The resulting solution was dried in vacuo, redissolved in $H_2O$ (10 mL), filtered, and purified via flash chromatography ($C_{18}$—$SiO_2$, 17:3 0.1% TFA (aq): MeCN). PyPrO: ESI-MS (cation): m/z calc 674.1 (M−1H$^+$), 337.6 (M$^{2+}$), obs. 674.0, 337.7. UV-Vis ($H_2O$, pH 7): 270 nm (122,400 M$^{-1}$ cm$^{-1}$), 300 nm (41,600 M$^{-1}$ cm$^{-1}$), 430 nm (12,300 M$^{-1}$ cm$^{-1}$). PPE: ESI-MS (cation): m/z calc 736.2 (M−1H$^+$), 368.6 (M$^{2+}$), obs. 736.0, 368.8. UV-Vis ($H_2O$, pH 7): 270 nm (165,800 M$^{-1}$ cm$^{-1}$), 300 nm (56,300 M$^{-1}$ cm$^{-1}$), 430 nm (16,100 M$^{-1}$ cm$^{-1}$). (Mixture of two isomers were obtained.)

As would be understood by those of ordinary skill in the art, the corresponding ruthenium complex, [Ru(chrysi)(phen)(PPE)]$^{2+}$ and [Ru(chrysi)(phen)(PyPrO)]$^{2+}$, can be made by the same process by substituting the [Rh(chrysi)(phen)($NH_3$)$_2$]$TFA_3$ with [Ru(chrysi)(phen)($NH_3$)$_2$]$TFA_2$.

Example 25

Synthesis of Ruthenium (Ru) Complexes

As would be understood by those having ordinary skill in the art, the synthesis scheme shown below can be easily adapted to make Ru analogs of any of the Rh complexes as disclosed herein by substitution of the appropriate ligands. The synthesis scheme shown is adapted from Brunner et al., 2006, *Biochemistry*, 45, 12295 and Copeland et al., 2002, *Biochemistry*, 41, 12785, the entire contents of both of which are incorporated herein by reference.

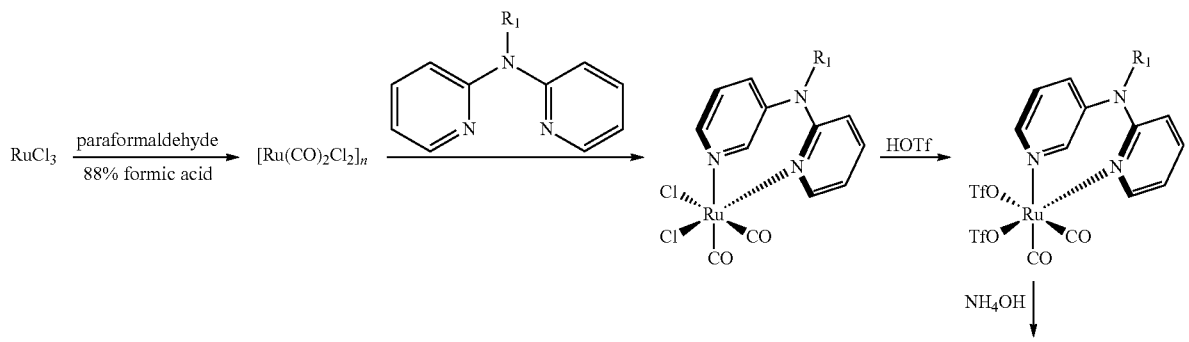

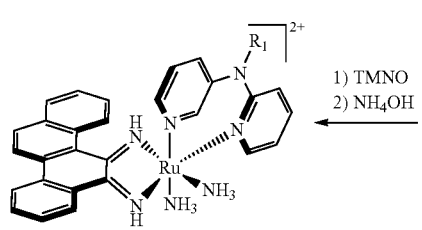 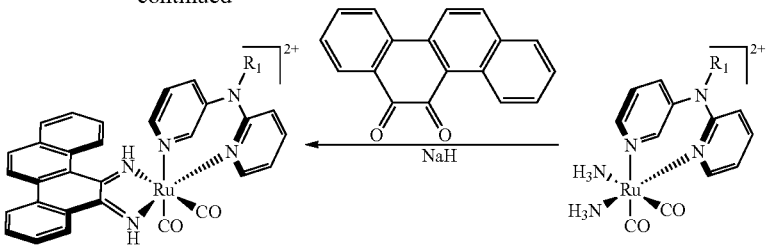

Example 26

PEGylation

Methods for PEGylation for drug delivery are known in the art. For example, Greenwald et al., 2003, *Adv. Drug Del. Rev.*, 55, 217; Molineux, 2003, *Pharmacotherapy*, (8 Pt 2), 3S-8S; Roberts et al., 2002, *Adv. Drug Deliv. Rev.*, 54, 459; Greenwald, 2001, *J. Controlled Release* 74, 159, and Veronese et al., 1995, *Adv. Drug Deliv. Rev.* 76, 157, the entire contents of all of which are incorporated herein by reference.

Methodology for Metalloinsertor Complex Assays

The metalloinsertor complexes as synthesized and described were assayed in cellulo using the isogenic colorectal carcinoma cell lines HCT116N and HCT116O. The methods used are as follows.

Example 27

Cell Culture

HCT116N and HCT116O cells were grown in RPMI medium 1640 supplemented with: 10% FBS; 2 mM L-glutamine; 0.1 mM nonessential amino acids; 1 mM sodium pyruvate; 100 units/mL penicillin; 100 µg/mL streptomycin; and 400 µg/mL geneticin (G418). Cells were grown in tissue culture flasks and dishes (Corning Costar, Acton, Mass.) at 37° C. under 5% $CO_2$ and humidified atmosphere.

Example 28

Cellular Proliferation ELISA

The ability of each of the complexes of FIGS. 1A through 1N, 1P and 1Q to selectively inhibit cell growth was assayed using a BrdU (5-bromo-2'-deoxyrudine) incorporation assay in the colorectal carcinoma cell lines HCT116N and HCT116O. BrdU is a synthetic thymidine analog that is incorporated into newly synthesized DNA during the S-phase of the cell cycle in growing cells. The HCT16N and HCT116O cell lines differ only in the presence of an active copy of the human MLH1 gene, which is essential for mismatch repair (MMR). HCT116N contains the active MLH1 gene, and is MMR proficient, while HCT116O lacks an active MLH1 gene and is MMR-deficient.

Figure 16:
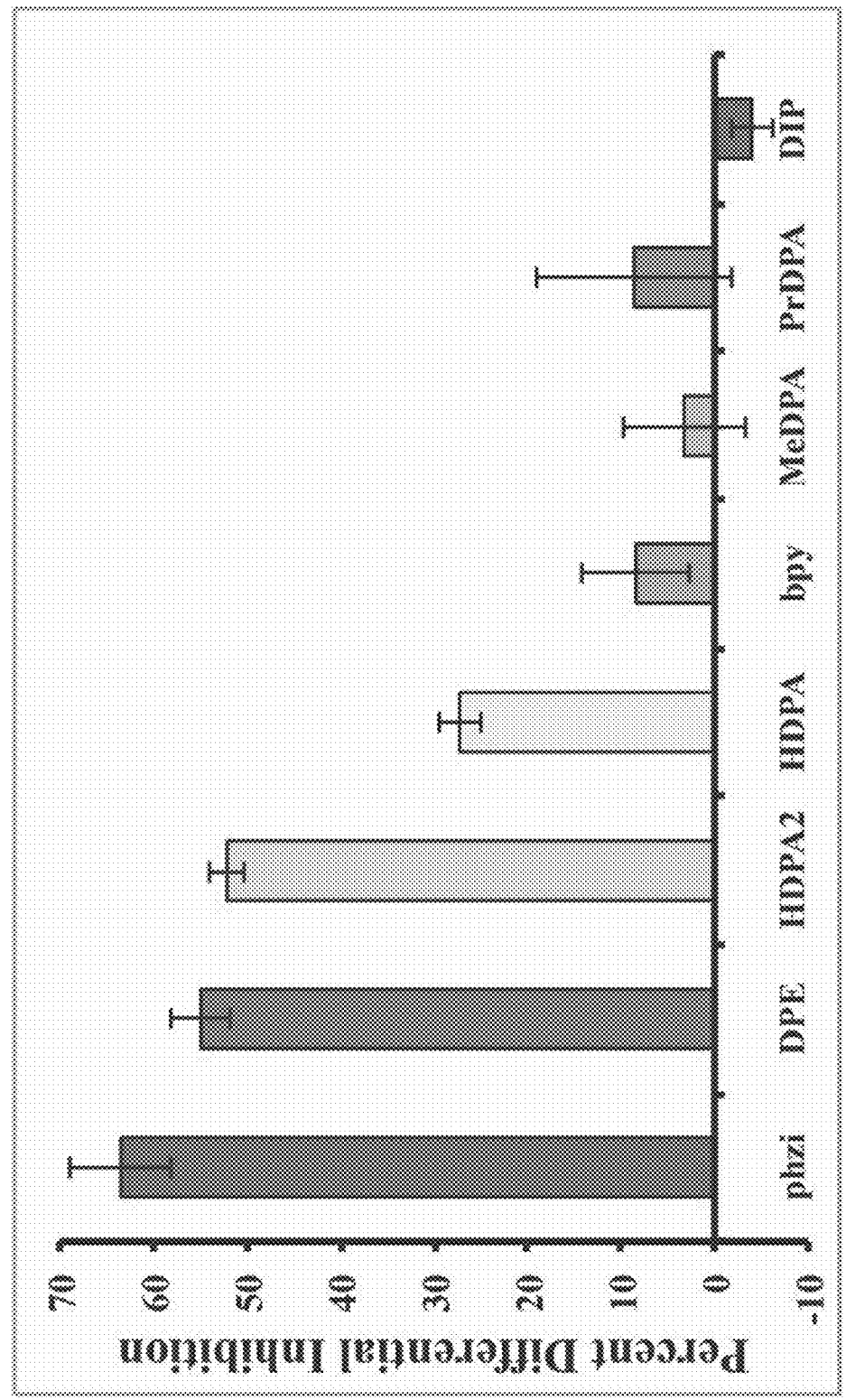
FIG. 16 is a graph showing the percent of differential inhibition of cellular proliferation between the HCT116N and the HCT116O cells when incubated with 10 μM of the rhodium complexes as indicated, for 24 hours, followed by BrdU incorporation and quantification, according to embodiments of the present invention.

The results of the BrdU assays for each of these complexes in both the HCT116N and HCT116O cell lines are shown in FIGS. 2-15B, and FIGS. 44-45. FIG. 16 is a graph showing the percent of selective inhibition of cell growth using metalloinsertor complexes of the present invention as indicated. HCT116N and HCT116O cells were plated in 96-well plates at 2,000 cells/well and allowed 24 hours to adhere. The cells were then incubated with rhodium for the durations specified. For incubation less than 72 hours, the Rh-containing media was replaced with fresh media, and the cells were grown for the remainder of the 72 hour period. Cells were labeled with BrdU 24 hours before analysis. The BrdU incorporation was quantified by antibody assay as described in Reitmar et al., 1997, *Cancer Res*, 57, 3765-3771 and Gratzner 1982, *Science*, 218, 474-475, the entire contents of both of which are incorporated herein by reference. Cellular proliferation was expressed as the ratio of the amount of BrdU incorporated by the treated cells to that of the untreated cells.

Example 29

MTT Cytotoxicity Assay

Cytotoxicity assays were performed as described in Mosmann, 1983, *J. Immunol. Methods*, 65, 55-63, the entire contents of which is incorporated herein by reference. HCT116N and HCT116O cells were plated in 96-well plates at 50,000 cells/well and incubated with rhodium for the durations specified. After incubation with the indicated rhodium complexes, cells were labeled with MTT for 4 hours at 37° C. under 5% $CO_2$ and humidified atmosphere. The resulting formazan crystals were dissolved with solubilizing reagent purchased from Roche according to the manufacturer's instructions. The dissolved formazan was quantified as the absorbance at 570 nm minus the background absorbance at 690 nm. Percent viability was determined as the ratio of the amount of formazan in the treated cells to that of the untreated cells.

Figure 17A:
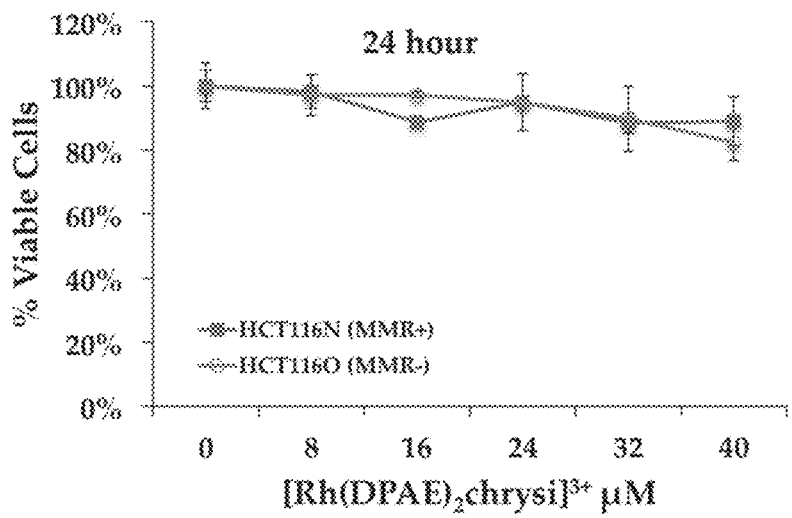
FIG. 17A is a graph of the amount (%) of viable cells as a function of [Rh(DPAE)$_2$chrysi]$^{3+}$ concentration in the HCT116N (squares) and the HCT116O (circles) cell lines after a 24 hour incubation, according to embodiments of the present invention.
Figure 17B:
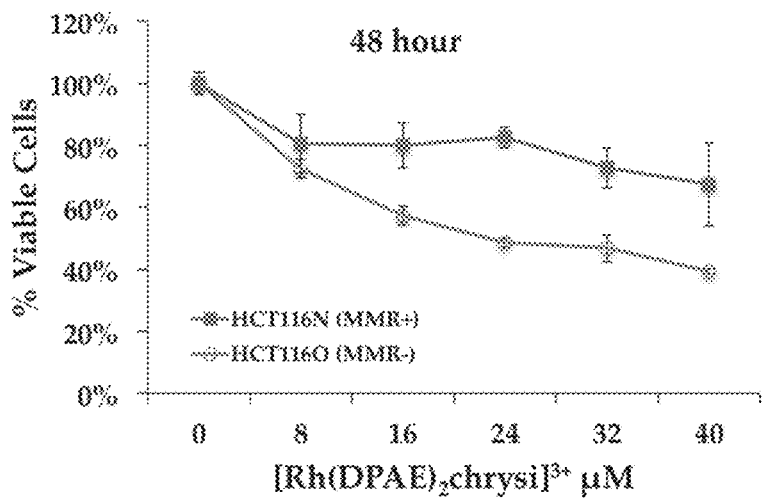
FIG. 17B is a graph of the amount (%) of viable cells as a function of [Rh(DPAE)$_2$chrysi]$^{3+}$ concentration in the HCT116N (squares) and the HCT116O (circles) cell lines after a 48 hour incubation, according to embodiments of the present invention.
Figure 17C:
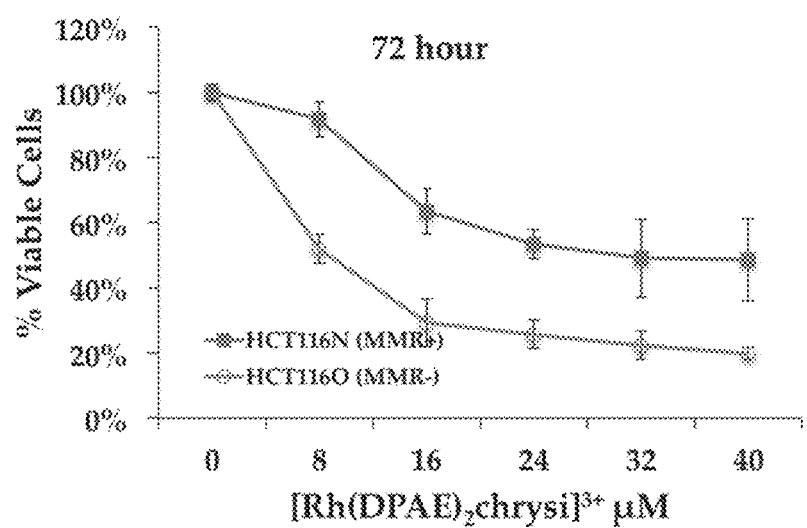
FIG. 17C is a graph of the amount (%) of viable cells as a function of [Rh(DPAE)$_2$chrysi]$^{3+}$ concentration in the HCT116N (squares) and the HCT116O (circles) cell lines after a 72 hour incubation, according to embodiments of the present invention.
Figure 18A:
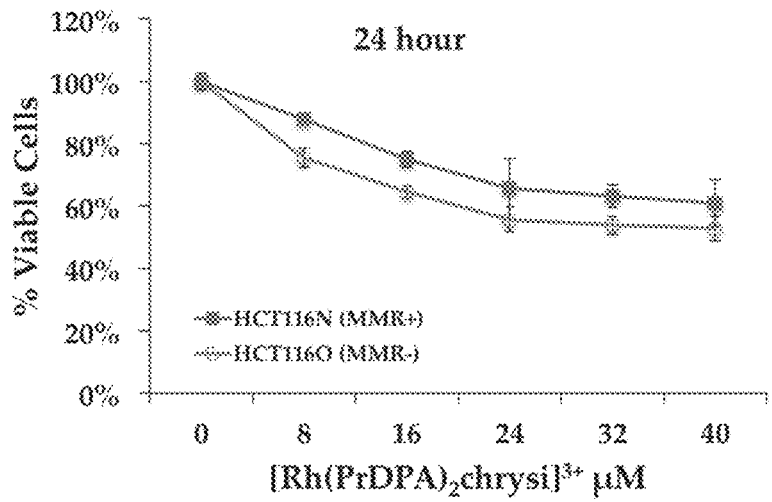
FIG. 18A is a graph of the amount (%) of viable cells as a function of [Rh(PrDPA)$_2$chrysi]$^{3+}$ concentration in the HCT116N (squares) and the HCT116O (circles) cells after a 24 hour incubation, according to embodiments of the present invention.
Figure 18B:
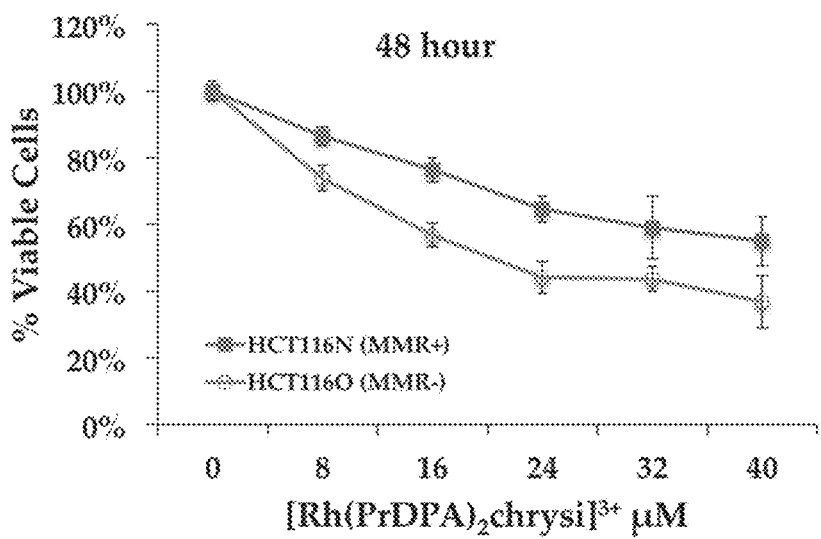
FIG. 18B is a graph of the amount (%) of viable cells as a function of [Rh(PrDPA)$_2$chrysi]$^{3+}$ concentration in the HCT116N (squares) and the HCT116O (circles) cell lines after a 48 hour incubation, according to embodiments of the present invention.

The results from cytotoxicity assays using $[Rh(DPAE)_2chrysi]^{3+}$ in the HCT116N and HCT116O cells are shown in FIGS. 17A-17C. As shown, the DPAE complex exhibits cell selective activity as early as 6 hours. That is, the DPAE complex imparts increased cytotoxicity to the MMR-deficient HCT116O cells. FIGS. 18A-18C show the results from cytotoxicity assays using $[Rh(PrDPA)_2chrysi]^{3+}$ in HCT116N and HCT116O cells. As shown, the PrDPA complex imparts non-selective inhibitory effects after 72 hours.

Figure 19A:
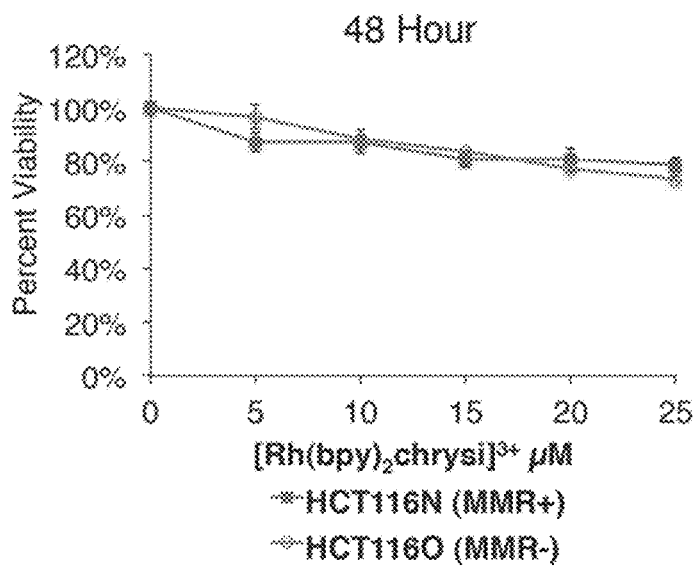
FIG. 19A is a graph of the amount (%) of viable cells as a function of [Rh(bpy)$_2$chrysi]$^{3+}$ concentration in the HCT116N (squares) and the HCT116O (circles) cell lines after a 48 hour incubation, according to embodiments of the present invention.
Figure 19B:
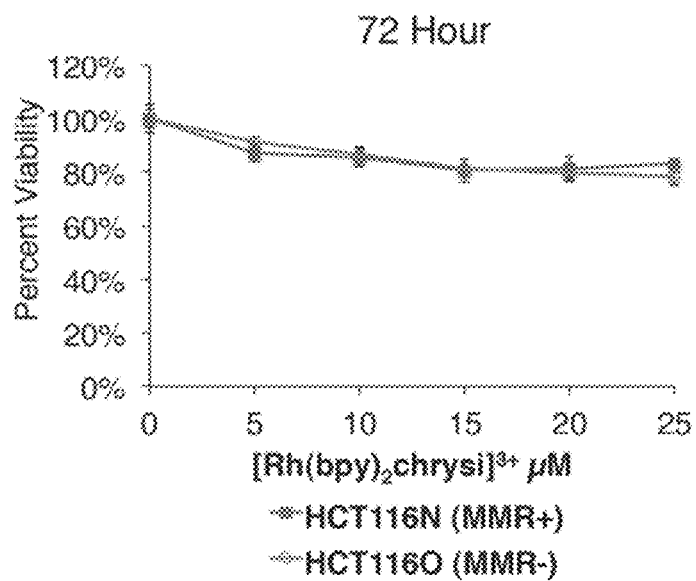
FIG. 19B is a graph of the amount (%) of viable cells as a function of [Rh(bpy)$_2$chrysi]$^{3+}$ concentration in the HCT116N (squares) and the HCT116O (circles) cell lines after a 72 hour incubation, according to embodiments of the present invention.
Figure 20A:
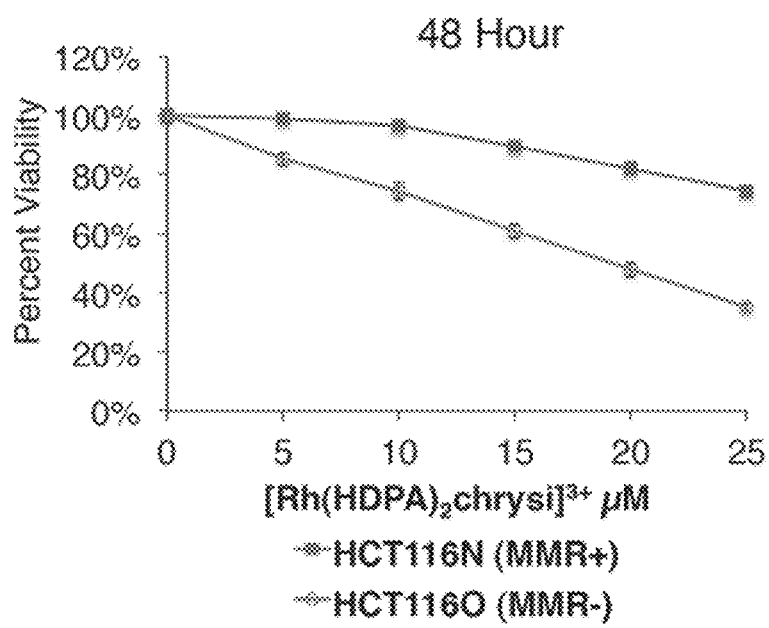
FIG. 20A is a graph of the amount (%) of viable cells as a function of [Rh(HDPA)$_2$chrysi]$^{3+}$ concentration in the HCT116N (squares) and the HCT116O (circles) cell lines after a 48 hour incubation, according to embodiments of the present invention.
Figure 20B:
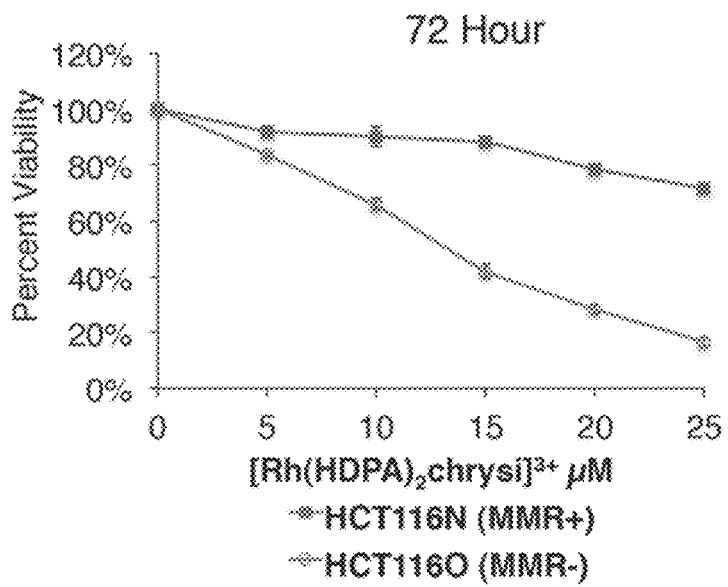
FIG. 20B is a graph of the amount (%) of viable cells as a function of [Rh(HDPA)$_2$chrysi]$^{3+}$ concentration in the HCT116N (squares) and the HCT116O (circles) cell lines after a 72 hour incubation, according to embodiments of the present invention.
Figure 21A:
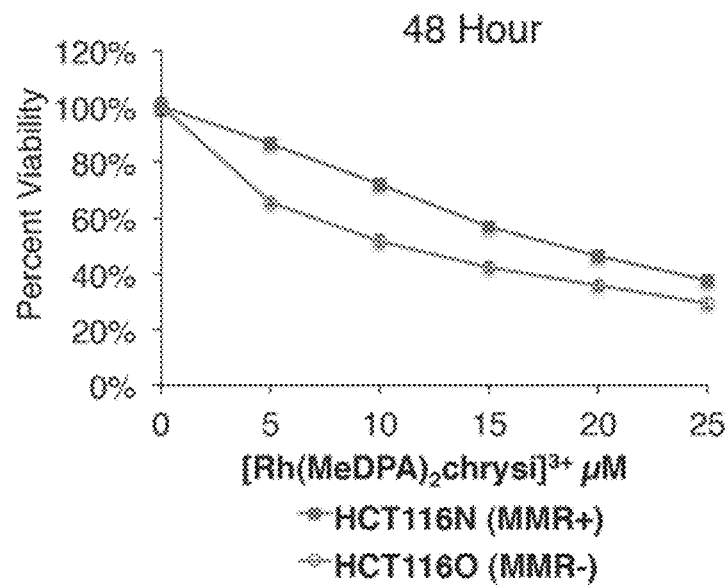
FIG. 21A is a graph of the amount (%) of viable cells as a function of [Rh(MeDPA)$_2$chrysi]$^{3+}$ concentration in the HCT116N (squares) and the HCT116O (circles) cell lines after a 48 hour incubation, according to embodiments of the present invention.
Figure 21B:
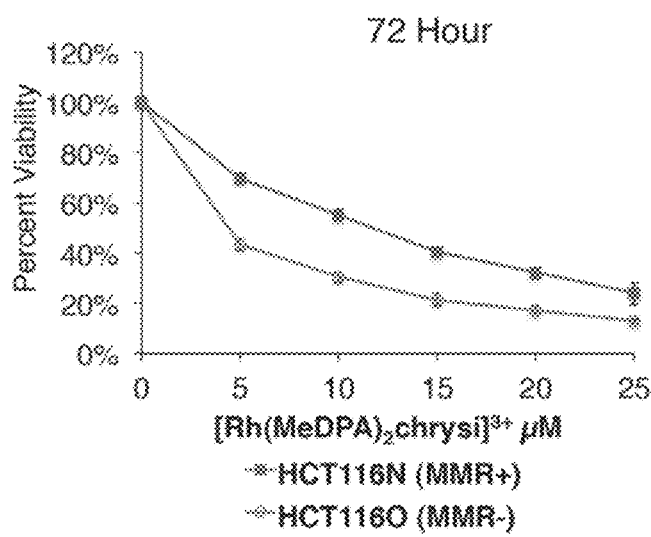
FIG. 21B is a graph of the amount (%) of viable cells as a function of [Rh(MeDPA)$_2$chrysi]$^{3+}$ concentration in the HCT116N (squares) and the HCT116O (circles) cell lines after a 72 hour incubation, according to embodiments of the present invention.
Figure 22:
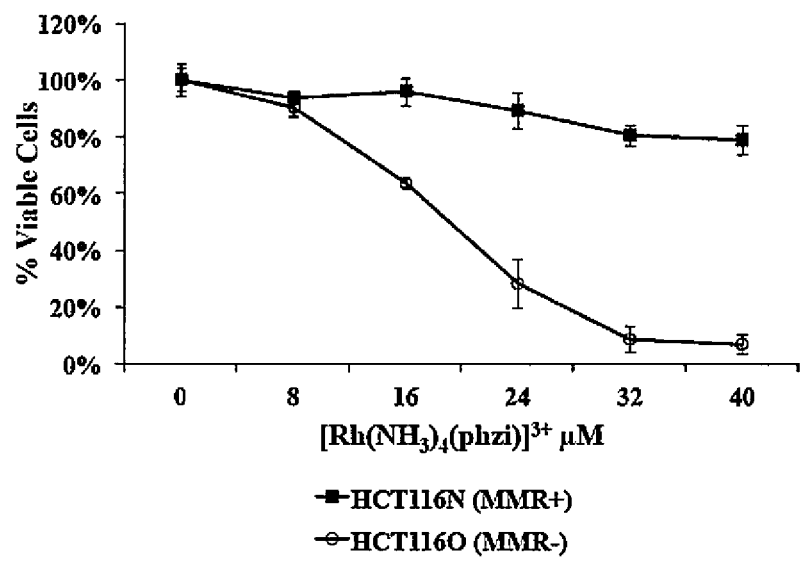
FIG. 22 is a graph of the amount (%) of viable cells as a function of [Rh(NH$_3$)$_4$phzi]$^{3+}$ concentration in the HCT116N (squares) and the HCT116O (circles) cell lines after a 72 hour incubation, according to embodiments of the present invention.
Figure 23:
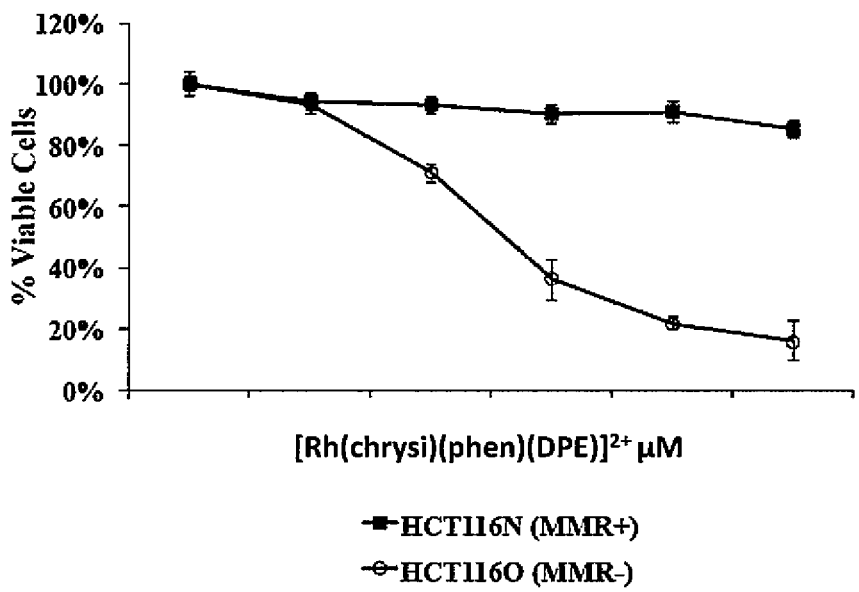
FIG. 23 is a graph of the amount (%) of viable cells as a function of [Rh(DPE)(phen)(chrysi)]$^{2+}$, concentration in the HCT116N (squares) and the HCT116O (circles) cell lines after a 72 hour incubation, according to embodiments of the present invention.
Figure 24:
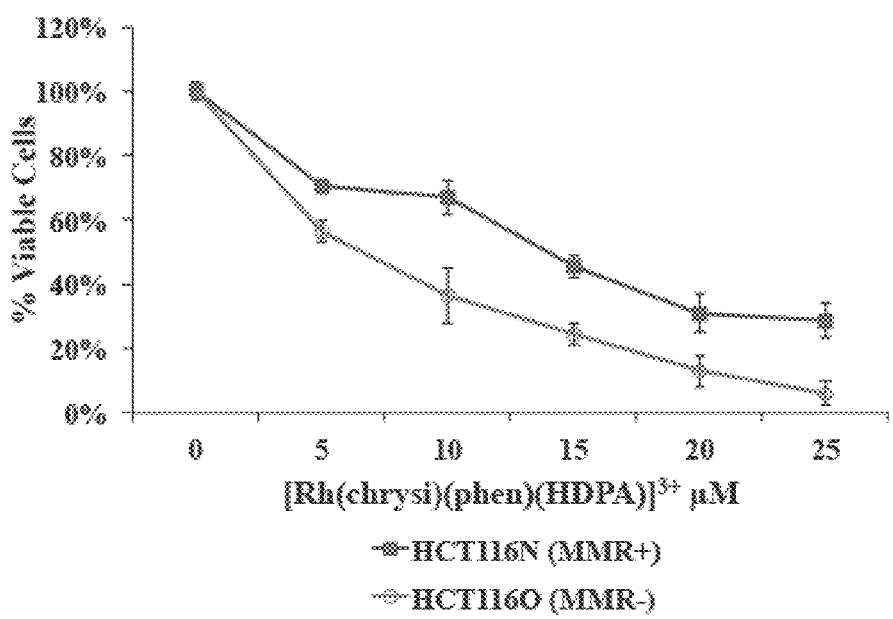
FIG. 24 is a graph of the amount (%) of viable cells as a function of [Rh(chrysi)(phen)(HDPA)]$^{3+}$ concentration in the HCT116N (squares) and the HCT116O (circles) cell lines after a 72 hour incubation, according to embodiments of the present invention.
Figure 25:
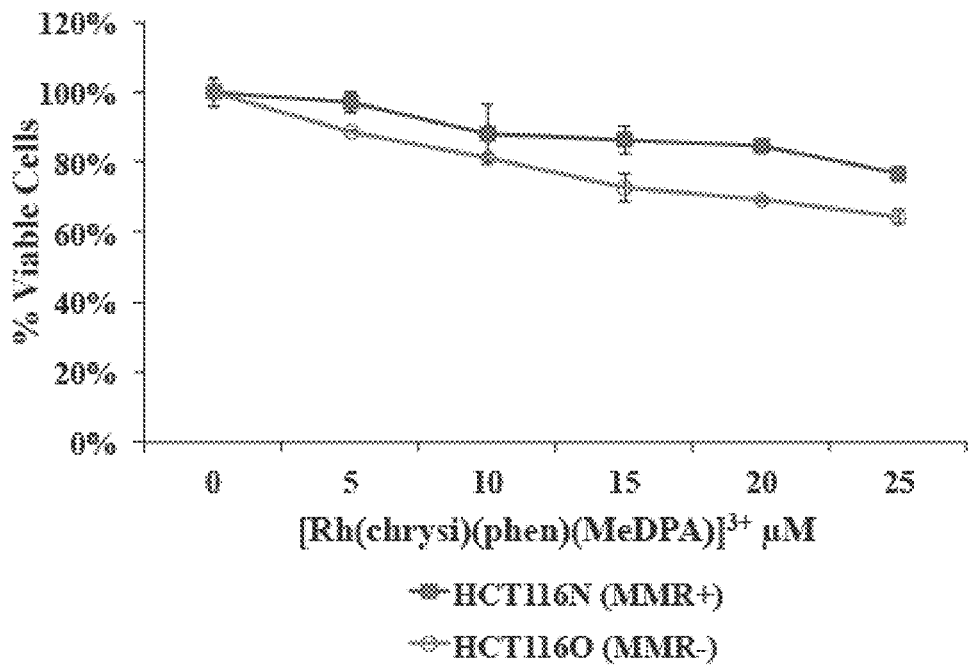
FIG. 25 is a graph of the amount (%) of viable cells as a function of [Rh(chrysi)(phen)(MeDPA)]$^{3+}$ concentration in the HCT116N (squares) and the HCT116O (circles) cell lines after a 72 hour incubation, according to embodiments of the present invention.
Figure 26:
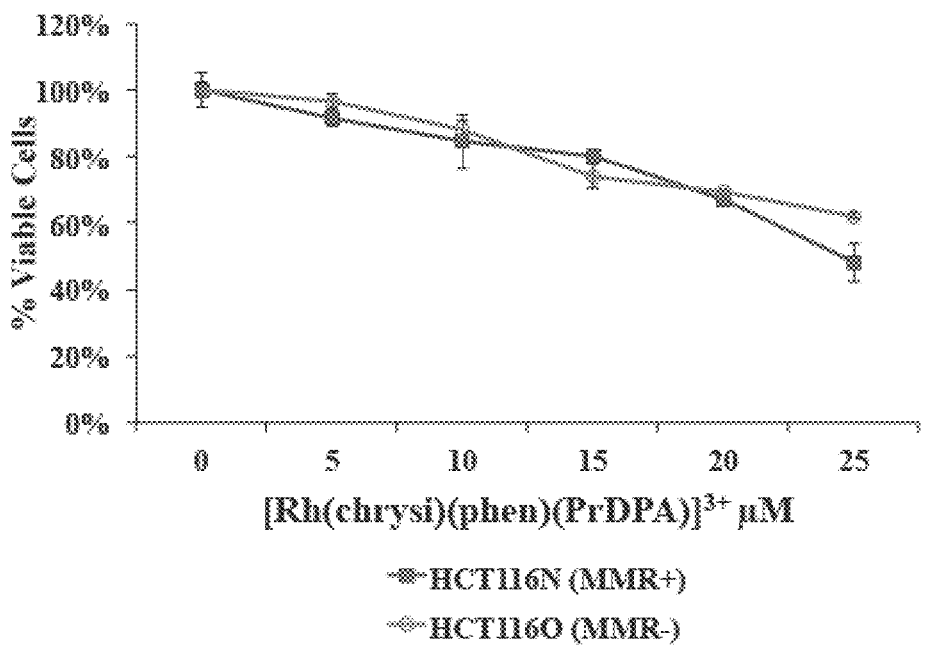
FIG. 26 is a graph of the amount (%) of viable cells as a function of [Rh(chrysi)(phen)(PrDPA)]$^{3+}$ concentration in the HCT116N (squares) and the HCT116O (circles) cell lines after a 72 hour incubation, according to embodiments of the present invention.
Figure 27:
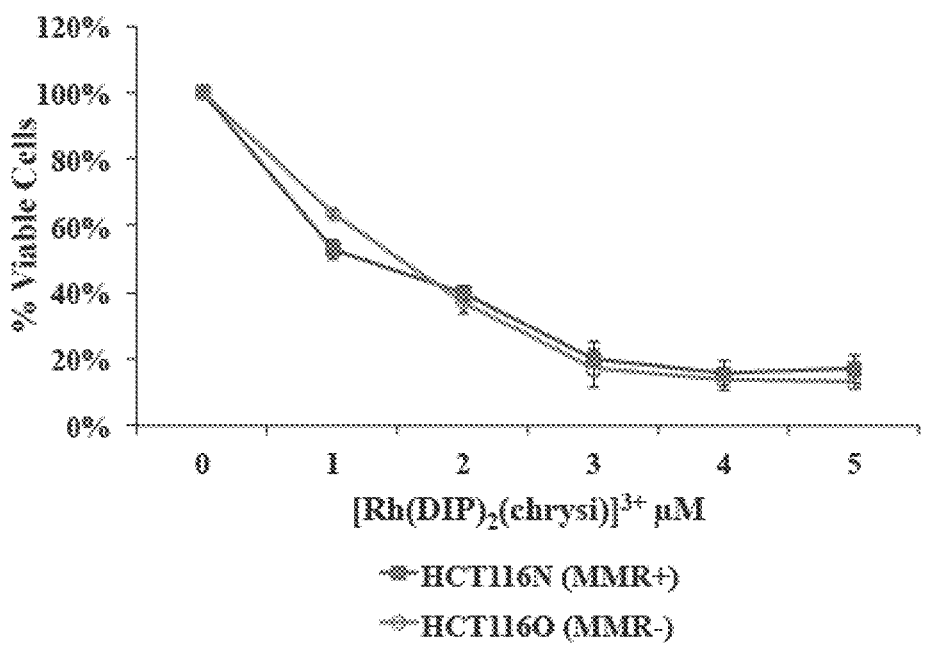
FIG. 27 is a graph of the amount (%) of viable cells as a function of [Rh(DIP)$_2$(chrysi)]$^{3+}$ concentration in the HCT116N (squares) and the HCT116O (circles) cell lines after a 72 hour incubation, according to embodiments of the present invention.

FIGS. 19A and 19B show the cytotoxicity results using the known non-toxic $[Rh(bpy)_2chrysi]^{3+}$ complex in the HCT116N and HCT116O cells. FIGS. 20A and 21B show cytotoxicity results using $[Rh(HDPA)_2chrysi]^{3+}$, and FIGS. 21A and 21B show the cytotoxicity results using $[Rh(MeDPA)_2chrysi]^{3+}$. As shown, both $[Rh(HDPA)_2chrysi]^{3+}$ $[Rh(MeDPA)_2chrysi]^{3+}$ complexes enhance toxicity in the MMR-deficient HCT116O cells at 48 hours. At 48 hours $[Rh(HDPA)_2chrysi]^{3+}$ and $[Rh(MeDPA)_2chrysi]^{3+}$ clearly display an enhanced toxicity in the MMR-deficient HCT116O cell line versus the HCT116N cell line (FIGS. 20A, 20B, 21A, and 21B). For example, 72 hours after treatment with 20 µM $[Rh(HDPA)_2chrysi]^{3+}$, the number of viable HCT116N cells is 80±5.2% of untreated controls, whereas the number of viable HCT116O cells is 37±4.4% of untreated controls. $[Rh(MeDPA)_2chrysi]^{3+}$ also shows differential toxicity against the HCT116O cell line comparable to that of $[Rh(HDPA)_2chrysi]^{3+}$.

FIGS. 22-27 show the results from cytotoxicity assays using $[Rh(NH_3)_4phzi]^{3+}$, $[Rh(chrysi)(phen)(DPE)]^{2+}$, $[Rh(chrysi)(phen)(HDPA)]^{3+}$ $[Rh(chrysi)(phen)(MeDPA)]^{3+}$, $[Rh(chrysi)(phen)(PrDPA)]^{3+}$, and $[Rh(DIP)_2(chrysi)]^{3+}$ in HCT116N and HCT116O cells, respectively. As shown, [Rh (NH3)$_4$phzi]$^{3+}$ and [Rh(chrysi)(phen)(DPE)]$^{2+}$ exhibit selective cytotoxicities towards the MMR-deficient HCT116O cells.

Figure 46:
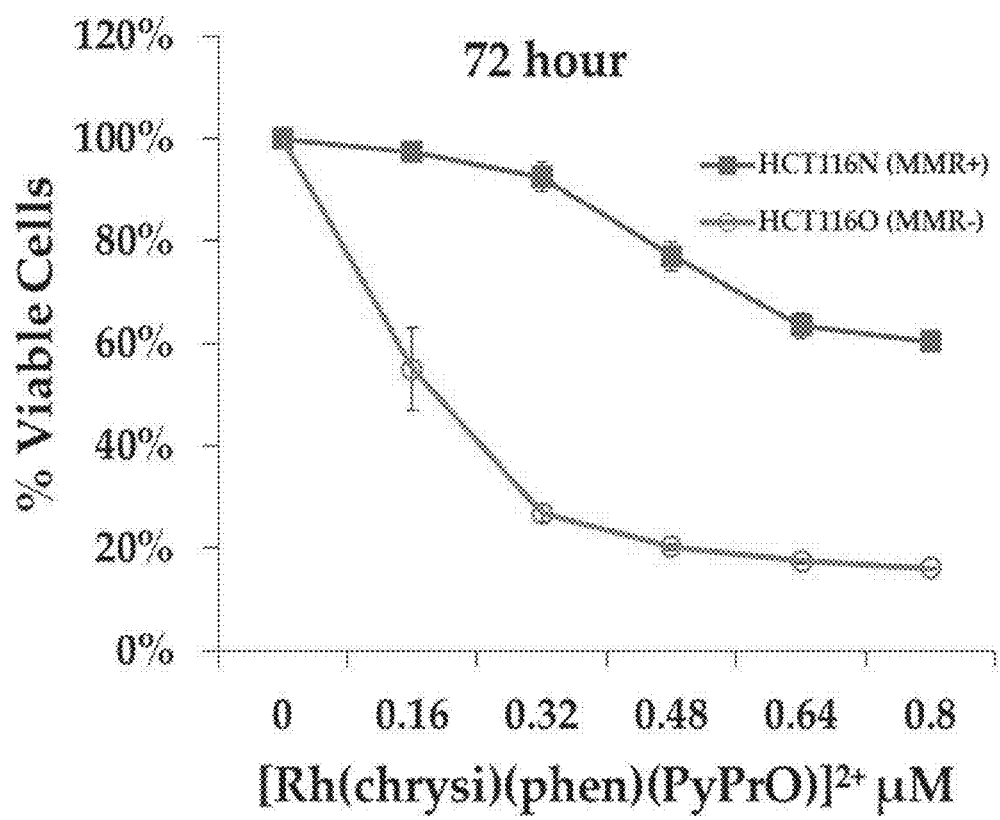
FIG. 46 is a graph of the amount (%) of viable cells as a function of [Rh(chrysi)(phen)(PyPrO)]$^{2+}$ concentration in the HCT116N (squares) and the HCT116O (circles) cell lines after a 72 hour incubation, according to embodiments of the present invention.
Figure 47:
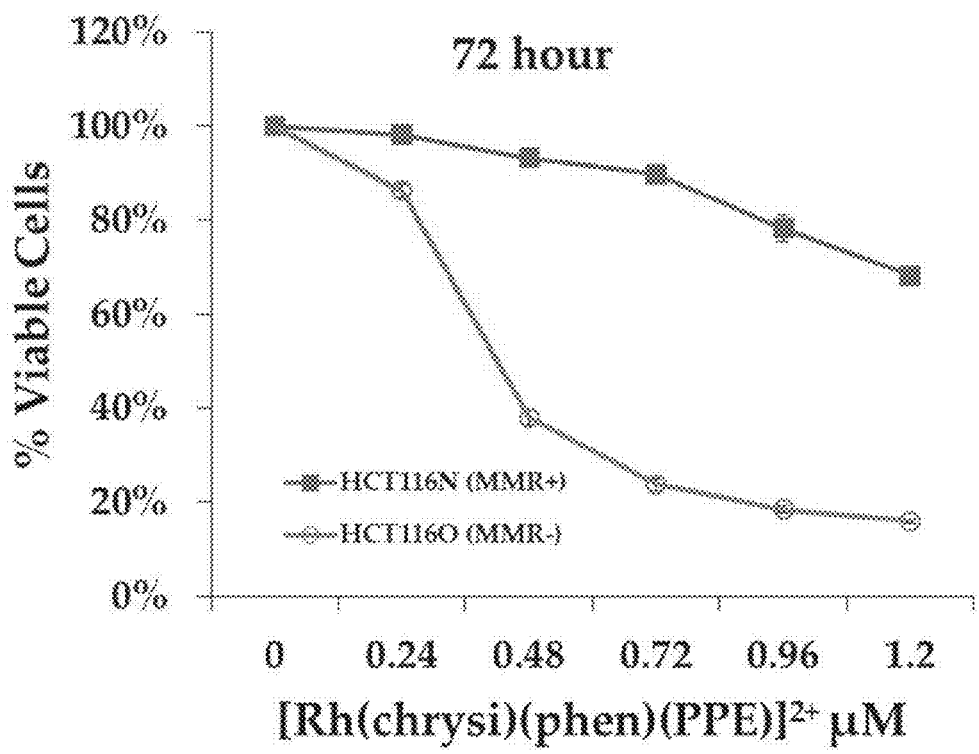
FIG. 47 is a graph of the amount (%) of viable cells as a function of [Rh(chrysi)(phen)(PPE)]$^{2+}$ concentration in the HCT116N (squares) and the HCT116O (circles) cell lines after a 72 hour incubation, according to embodiments of the present invention.

FIGS. 46-47 show the results of cytotoxicity assays using [Rh(chrysi)(phen)(PyPrO)]$^{2+}$ and [Rh(chrysi)(phen)(PPE)]$^{2+}$ in HCT116N and HCT116O cells, respectively. As shown, [Rh(chrysi)(phen)(PyPrO)]$^{2+}$ and [Rh(chrysi)(phen)(PPE)]$^{2+}$ exhibit selective cytotoxicities towards the MMR-deficient HCT116O cells.

Example 30

Binding Competition Titrations

Figure 30A:
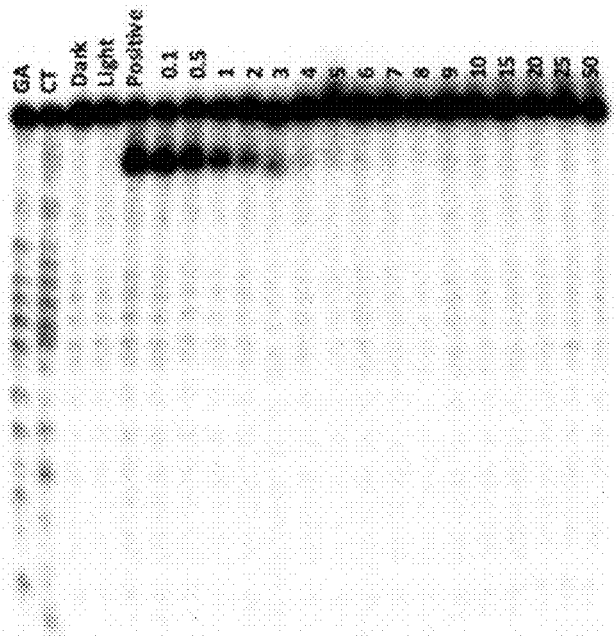
FIG. 30A is an autoradiogram of a 20% denaturing polyacrylamide gel of $^{32}$P-labeled hairpin DNA in the presence and absence of rac-[Rh(DPAE)$_2$(chrysi)]$^{3+}$.
Figure 30B:
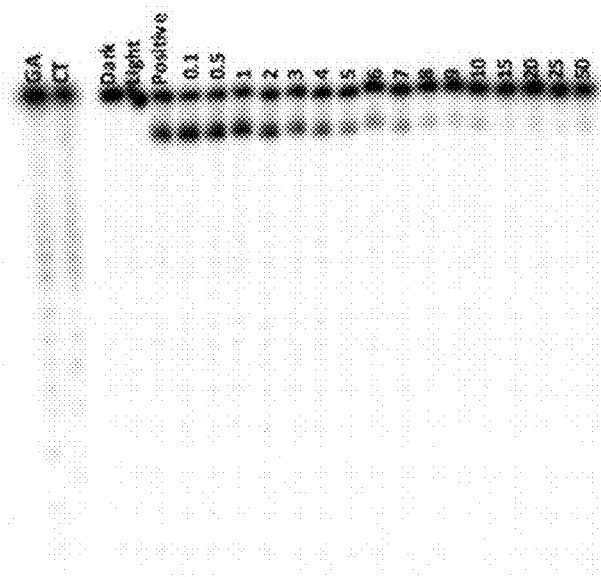
FIG. 30B is an autoradiogram of a 20% denaturing polyacrylamide gel of $^{32}$P-labeled hairpin DNA in the presence and absence of rac-[Rh(PrDPA)$_2$(chrysi)]$^{3+}$.
Figure 30C:
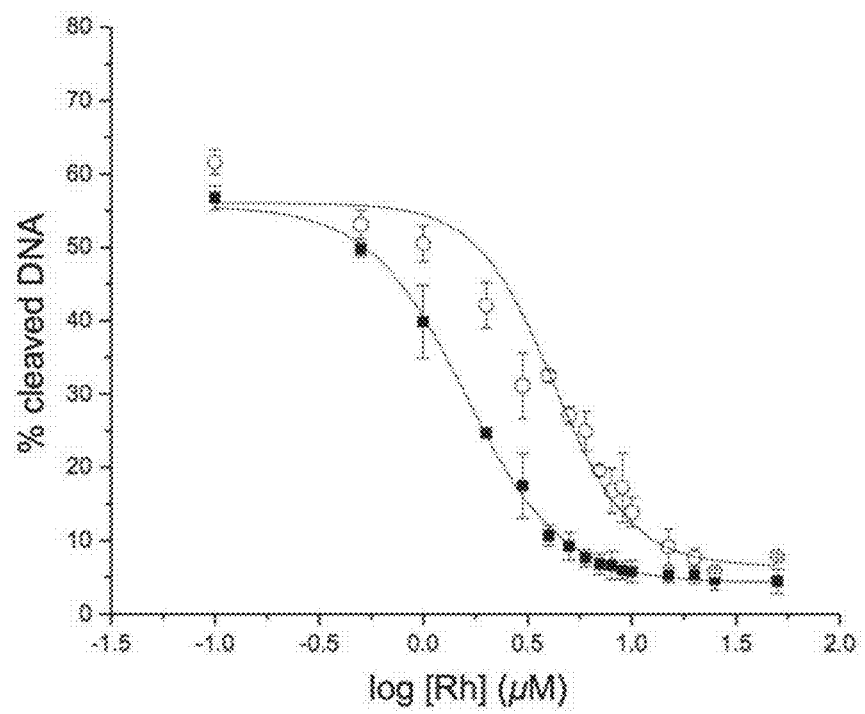
FIG. 30C is a sigmoidal curve fits graph of binding affinity competition titrations calculated from the autoradiograms of FIG. 30A for [Rh(DPAE)$_2$(chrysi)]$^{3+}$ (squares) and of FIG. 30B for [Rh(PrDPA)$_2$(chrysi)]$^{3+}$ (circles), according to embodiments of the present invention.

For FIGS. 30A-30C, a 29-mer DNA hairpin containing a CC mismatch (underlined) (*5'-GGCAGGCATG-GCTTTTTGCCATCCCTGCC-3') was labeled with $^{32}$P at the 5'-end as described in Zeglis et al., 2007, Nat. Protoc. 2, 357-371, the entire contents of which are incorporated herein by reference. A 1:1 mixture of labeled and unlabeled DNA was prepared in buffer (100 mM NaCl, 20 mM NaP$_i$, pH 7.1) to a final concentration of 2 µM. The hairpin was annealed by heating to 90° C. for 10 min and slowly cooled to room temperature. To prepare samples for gel electrophoresis, 4 µM [Rh(bpy)$_2$chrysi]C$_3$ (5 µL) and varying concentrations of rac-Rh(DPAE)$_2$chrysi$^{3+}$ or rac-Rh(PrDPA)$_2$chrysi$^3$ (5 µL) were added to 2 µM annealed DNA hairpin (10 µL). A light control (10 µL DNA, 10 µL H$_2$O), a dark control (10 µL DNA, 5 µL Rh(bpy)$_2$chrysi$^{3+}$, 5 µL rac-Rh(DPAE)$_2$chrysi$^{3+}$ or rac-Rh(PrDPA)$_2$chrysi$^3$, no irradiation), and a positive control (10 µL DNA, 5 µL Rh(bpy)$_2$chrysi$^{3+}$, 5 µL H$_2$O) were also prepared. Samples were vortexed and, except for the dark control, irradiated on an Oriel (Darmstadt, Germany) 1000-W Hg/Xe solar simulator (340-440 nm) for 15 min. Samples were then incubated at 37° C. for 20 min, dried, then electrophoresed through a 20% denaturing polyacrylamide gel. The gel was exposed on a phosphor screen, phosphorimaged, and the amounts of DNA cleavage were quantified using ImageQuant.

To determine the K$_B$ values of rac-Rh(DPAE)$_2$chrysi$^{3+}$ and rac-Rh(PrDPA)$_2$chrysi$^3$, competition gels were run in triplicate for each complex, and the percent DNA cleavage at each concentration was averaged and plotted as a function of log [Rh](FIG. 30C). The data were fit to a sigmoidal curve using OriginPro 8.1. K$_B$ values were determined by calculating the concentration of rhodium at the inflection points of the curve and solving simultaneous equilibria involving DNA, Rh(bpy)$_2$chrysi$^{3+}$ and rac-Rh(DPAE)$_2$chrysi$^{3+}$ or rac-Rh(PrDPA)$_2$chrysi$^3$ in Mathematica 8.0. The dissociation constant K, is defined as 1/K$_B$.

For the autoradiograms of rac-Rh(DPAE)$_2$chrysi$^{3+}$ (FIG. 30A) and rac-Rh(PrDPA)$_2$chrysi$^{3+}$ (FIG. 30B) a light control (Light, without rhodium), dark control (Dark, without irradiation), and positive control (Positive, only Rh(bpy)$_2$chrysi$^{3+}$) are included. Concentrations of competitors Rh(DPAE)$_2$chrysi$^{3+}$ and Rh(PrDPA)$_2$chrysi$^{3+}$ range from 0.1-50 µM, with 1 µM Rh(bpy)$_2$chrysi$^{3+}$.

Example 31

ICP-MS Assay for Cellular Rhodium Levels

To assay the subcellular localization of the rhodium complexes, an inductively coupled plasma mass spectrometry (ICP-MS) assay was used to quantify the uptake of the complexes in both whole cell extracts and nuclear and mitochondrial fractions.

Figure 33A:
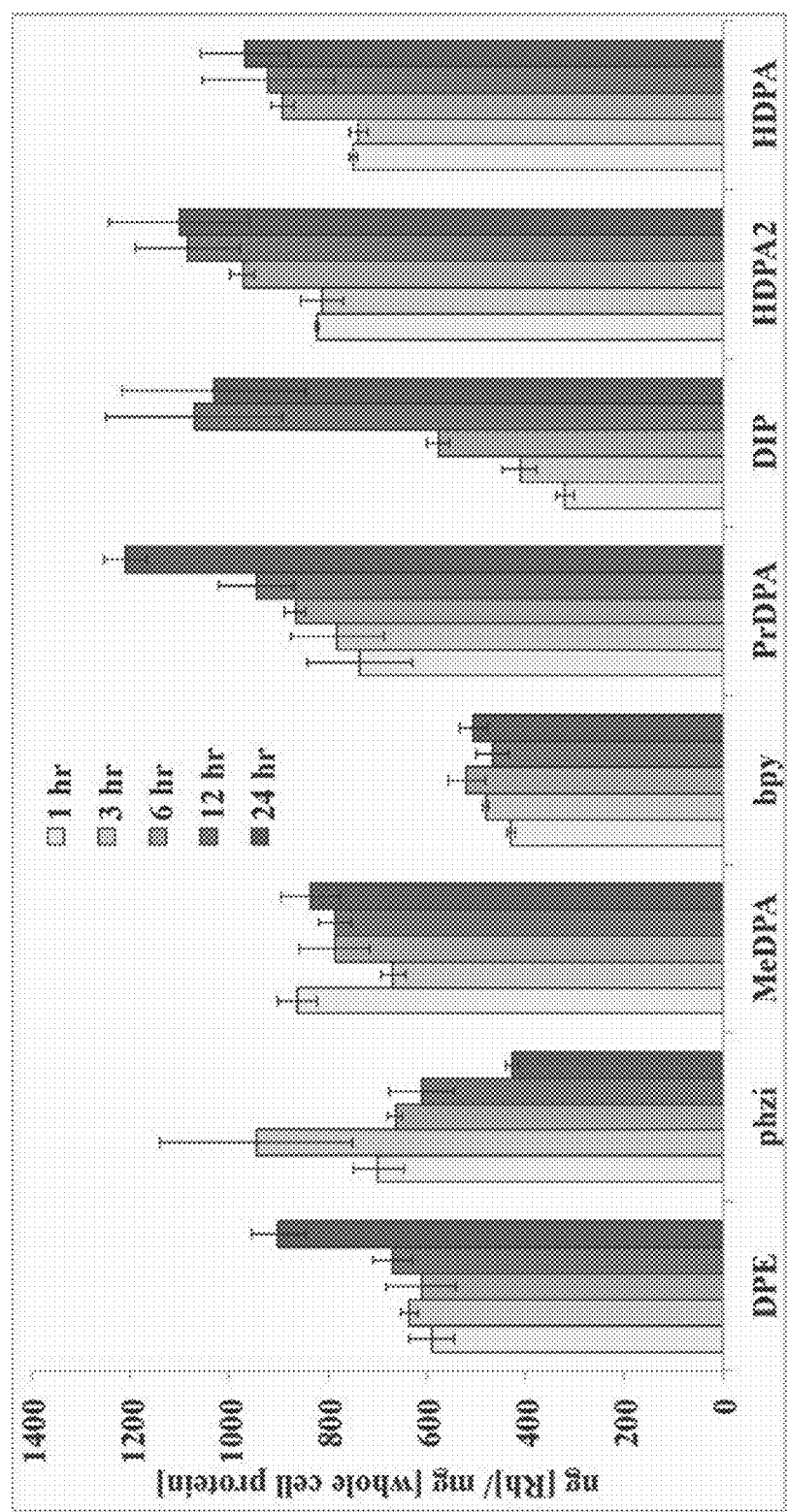
FIG. 33A is a graph of the results from an ICP-MS assay for quantifying the whole-cell rhodium accumulation in HCT116O cells treated with 10 μm of each of the indicated rhodium complexes, or 2 μm of [Rh(DIP)$_2$(chrysi)]$^{3+}$ complex for 1, 3, 6, 12, or 24 hours (left to right), according to embodiments of the present invention.

Each cell line was treated with 10 µM of each rhodium complex as indicated in FIG. 33A (except [Rh(DIP)$_2$(chrysi]$^{3+}$ which was administered at 2 µM) for 1, 3, 6, 12, 24, or 48 hours. After rhodium incubation, the cells were harvested from adherent culture by trypsinization, washed with cold PBS, and counted by hemacytometer. The samples were pelleted and resuspended in 1% HNO$_3$ (v/v), homogenized by three freeze/thaw cycles in liquid nitrogen, and analyzed for rhodium content on an HP-4500 ICP-MS unit. Rhodium counts were normalized to the number of cells counted in each sample before lysate preparation. Standard errors for three independent experiments are shown.

Figure 31A:
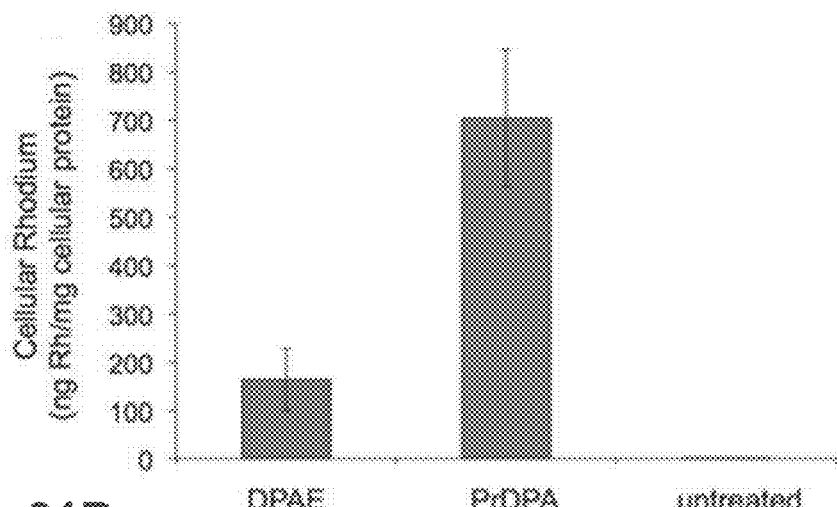
FIG. 31A is a graph of the results from an ICP-MS (inductively coupled plasma mass spectrometry) assay quantifying the uptake of [Rh(DPAE)$_2$(chrysi)]$^{3+}$ ("DPAE") and [Rh(PrDPA)$_2$(chrysi)]$^{3+}$ ("PrDPA") in whole cell extracts of HCT116O cells, according to embodiments of the present invention.

Whole-Cell Rhodium Accumulation. With reference to FIG. 31A, HCT116O cells were plated in 6-well plates at 1.0×10$^6$ cells/well (3 ml media), and allowed 24 h to adhere. The cells were then incubated with 10 µM rac-Rh(DPAE)$_2$chrysi$^+$ or rac-Rh(PrDPA)$_2$chrysi$^3$ for an additional 24 h. Cells were lysed with 1% SDS and sonicated. Samples were aliquoted (0.75 ml) and diluted with 2% HNO$_3$ (0.75 ml), and cellular rhodium content was quantified on an HP-4500 ICP-MS unit. The remainder of the cell lysates were analyzed for protein content via bicinchoninic acid (BCA) assay. Rhodium counts were normalized to protein content, and standard errors were calculated from three replicates.

Figure 31B:
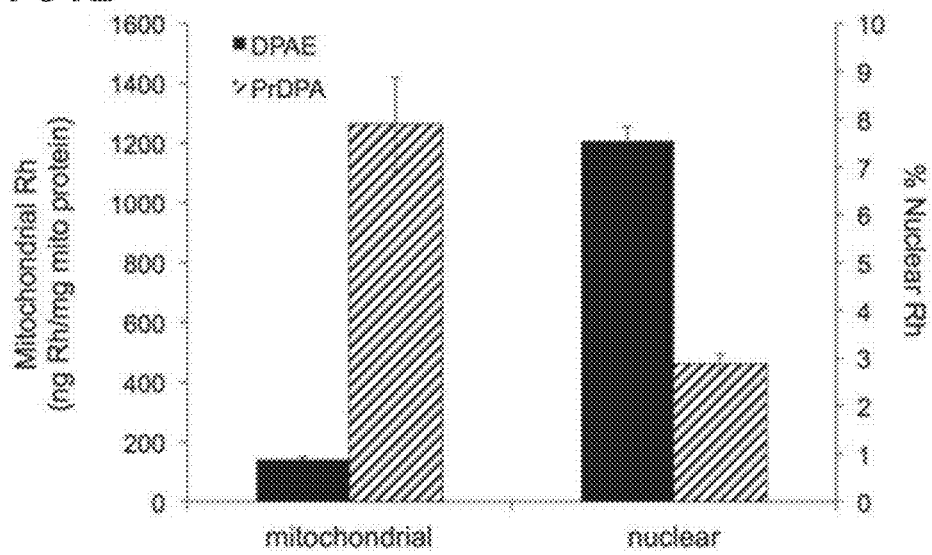
FIG. 31B is a graph of the results from an ICP-MS assay quantifying the uptake of [Rh(DPAE)$_2$(chrysi)]$^{3+}$ ("DPAE") (solid black) and [Rh(PrDPA)$_2$(chrysi)]$^{3+}$ ("PrDPA") (hashed lines) in nuclear and mitochondrial fractions of HCT116O cells, according to embodiments of the present invention.

Mitochondrial Rhodium Accumulation. With reference to FIG. 31B, HCT116O cells were plated in 75 cm$^2$ culture flasks at 2.0×10$^7$ cells/plate and incubated at 37° C., 5% CO$_2$ for 24 h. Rhodium was added to 10 uM and cells were grown for an additional 24 h. The cells were then harvested by trypsinization and centrifuged for 5 min at 1,200 rpm. The supernatants were decanted, and the cell pellets were resuspended in 1 ml cold PBS (pH 7.2). The cells were centrifuged again for 5 min at 1,200 rpm. The supernatants were discarded, and the resultant pellets were resuspended in 0.5 ml mitochondrial extraction buffer (200 mM mannitol, 68 mM sucrose, 50 mM Pipes, 50 mM KCl, 5 mM EGTA, 2 mM MgCl$_2$; 1 mM DTT and protease inhibitors were added right before use). The samples were incubated on ice for 20 min, and the suspensions were homogenized via passage through a needle and syringe (35×). The homogenized cells were then centrifuged for 5 min at 750 rpm. The supernatants were collected and spun again at 14,000 g for 10 min. The supernatants were decanted, and the resulting mitochondrial pellet was suspended in 0.8 ml H$_2$O via probe sonication. All samples were diluted 1× with 2% HNO$_3$. 20 uL aliquots were used in a BCA assay to determine protein content, which was carried out according to standard protocol. Rh counts from ICP MS were converted to ppb and normalized to protein content (ng Rh/mg protein). The purity of mitochondrial fractions was ascertained by Western blot.

Nuclear Rhodium Accumulation. With reference to FIG. 31B, HCT116O cells were plated in 75 cm$^2$ culture flasks at 1.5×10$^7$ cells/plate and incubated at 37° C., 5% CO$_2$, for 24 h. Rhodium was then added to 10 uM and cells were grown for an additional 24 h. The cells were trypsinized according to standard protocol, and the cell pellets were washed with 3 mL 1×PBS (pH 7.2) and spun at 1200 rpm for 5 minutes. The supernatant was discarded, and the pellets were resuspended in 1 mL 1×PBS and divided into 2×0.5 mL aliquots (nuclear and whole cell). The samples were spun at 450 g for 5 minutes at 4° C. The supernatants were decanted and the whole cell pellets were dissolved in 1 mL Milli-Q water. The nuclear pellets were dissolved in 1 mL hypotonic buffer (20 mM Tris-HCl, pH 7.4; 10 mM NaCl, 3 mM MgCl$_2$) and incubated on ice for 15 min. After 15 min, 50 uL of NP-40 detergent were added and the samples were vortexed for 10 s. Samples were then spun at 3000 g for 10 min at 4° C. The supernatants were discarded, and the nuclear pellets were dissolved in 1 mL Milli-Q water via sonication. All samples were diluted 1× with 2% HNO$_3$. 20 uL aliquots were used in a BCA assay to determine protein content, which was carried out according to standard protocol. Rh counts from ICP MS were converted to ppb and normalized to protein content (ng Rh/mg protein).

As shown in FIGS. 31A and 31B the mitochondrial rhodium content in cells incubated with [Rh(PrDPA)$_2$(chrysi)]$_{3+}$ is greater than that of cells incubated with [Rh (DPAE)$_2$(chrysi)]$^{3+}$. This difference in localization correlates with the lipophilic characteristics of [Rh(PrDPA)$_2$(chrysi)]$^3$ which facilitate uptake in response to mitochondrial membrane potential. A greater percentage of cellular [Rh(DPAE)$_2$(chrysi)]$^{3+}$ is nuclear. Accordingly, the MMR-selective effects to override any nonspecific consequences of mitochondrial accumulation.

Figure 32:
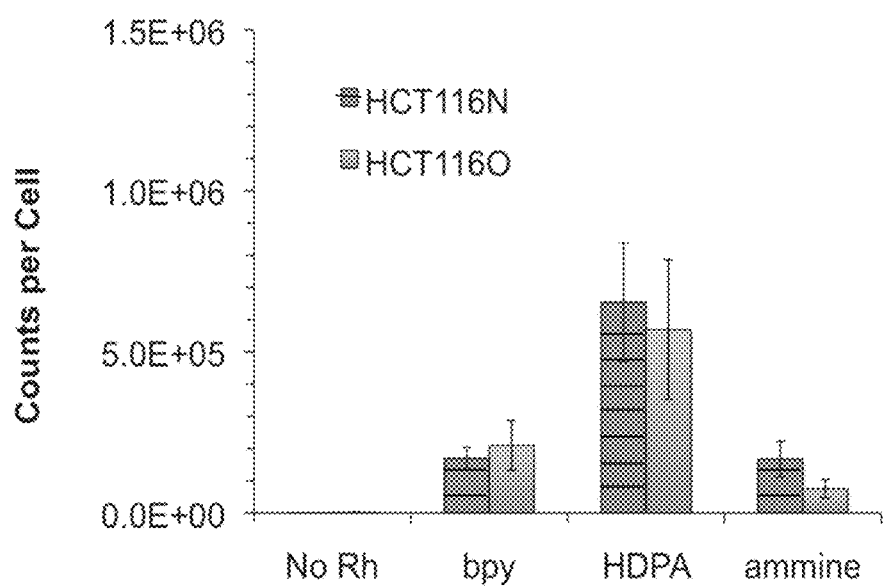
FIG. 32 is a graph of the results from an ICP-MS assay for rhodium accumulation in whole cell lysates of HCT116N (solid with lines) and HCT116O (solid) cells treated with No Rh, or 10 μm of [Rh(bpy)$_2$chrysi]$^{3+}$, [Rh(HDPA)$_2$chrysi]$^{3+}$, or [Rh(NH$_3$)$_4$chrysi]$^{3+}$ (amine) for 48 hours, according to embodiments of the present invention.
Figure 33B:
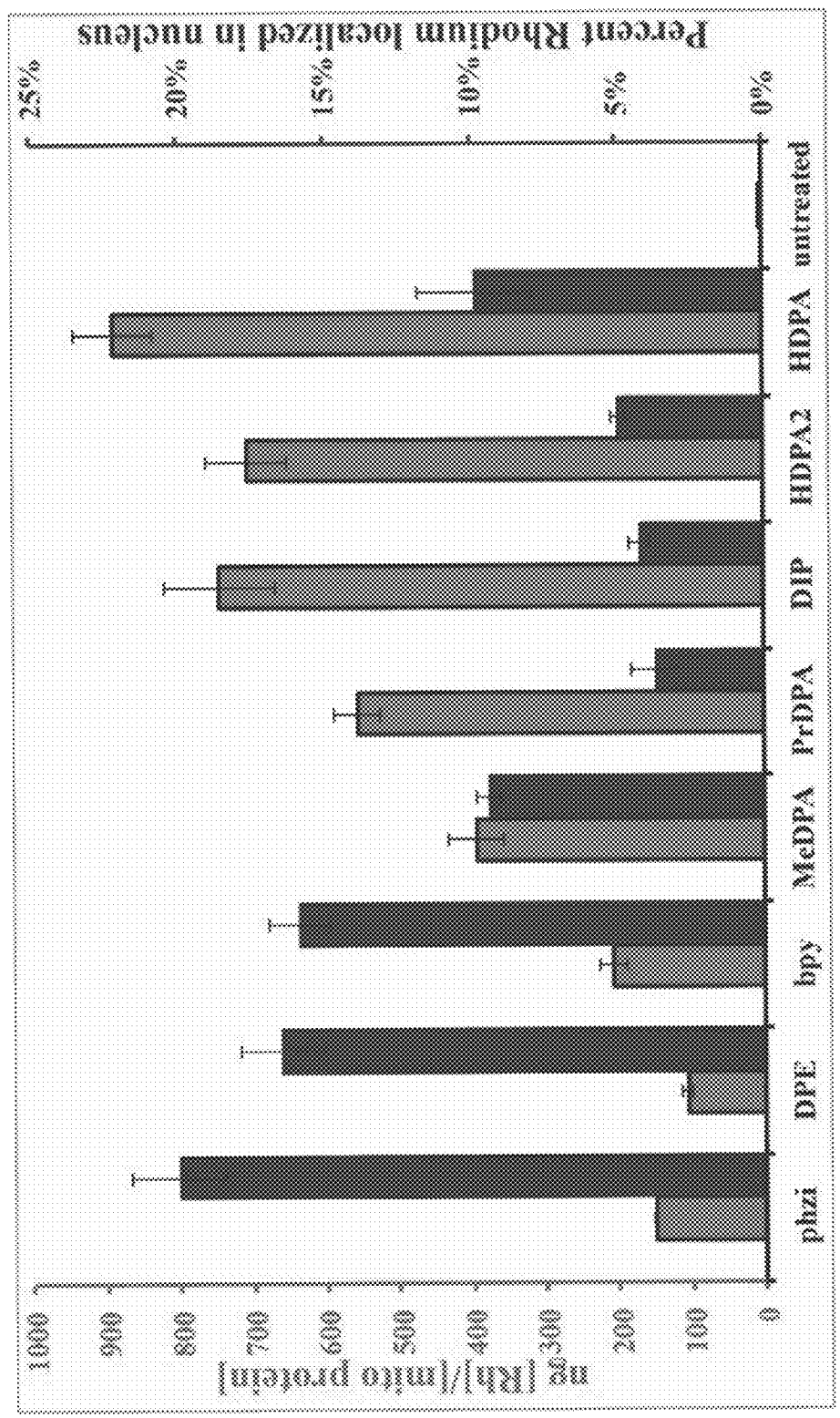
FIG. 33B is a graph of the results from an ICP-MS assay for quantifying the rhodium accumulation in the nucleus (right y-axis, right bars) and mitochondria (left y-axis, left bars) of HCT116O cells treated with 10 μm of each of the indicated rhodium complexes, or 2 μm of [Rh(DIP)$_2$(chrysi)]$^{3+}$ complex for 24 hours, according to embodiments of the present invention.
Figure 34A:
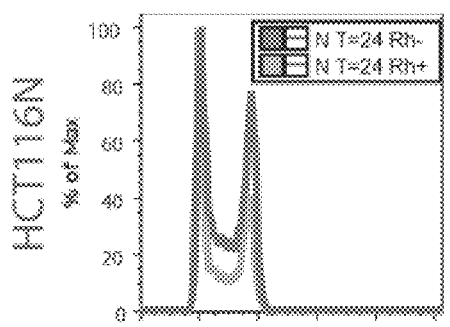
FIG. 34A is a graph comparing the cell cycle distributions of untreated HCT116N cells (dark gray) and HCT116N cells after treatment with 20 μm [Rh(HDPA)$_2$chrysi]$^{3+}$ (light gray) for a 24 hour incubation, followed by fixation and staining with propidium iodide (PI) and flow cytometry analysis, according to embodiments of the present invention.
Figure 34B:
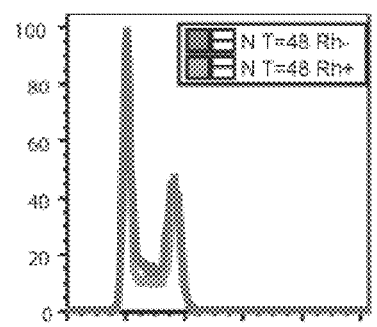
FIG. 34B is a graph comparing the cell cycle distributions of untreated HCT116N cells (dark gray) and HCT116N cells after treatment with 20 μm [Rh(HDPA)$_2$chrysi]$^{3+}$ (light gray) for a 48 hour incubation, followed by fixation and staining with propidium iodide (PI) and flow cytometry analysis, according to embodiments of the present invention.
Figure 34C:
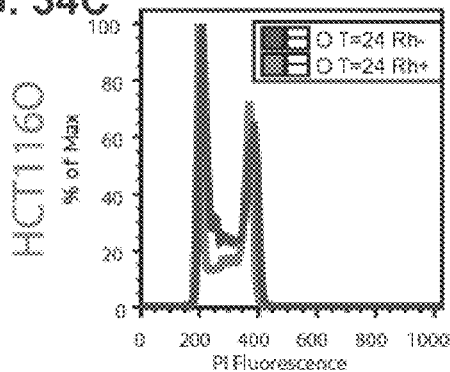
FIG. 34C is a graph comparing the cell cycle distributions of untreated HCT116O cells (dark gray) and HCT116O cells after treatment with 20 μm [Rh(HDPA)$_2$chrysi]$^{3+}$ (light gray) for a 24 hour incubation, followed by fixation and staining with propidium iodide (PI) and flow cytometry analysis, according to embodiments of the present invention.
Figure 34D:
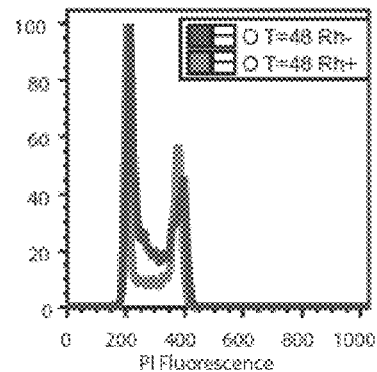
FIG. 34D is a graph comparing the cell cycle distributions of untreated HCT116O cells (dark gray) and HCT116O cells after treatment with 20 μm [Rh(HDPA)$_2$chrysi]$^{3+}$ (light gray) for a 48 hour incubation, followed by fixation and staining with propidium iodide (PI) and flow cytometry analysis, according to embodiments of the present invention.
Figure 35A:
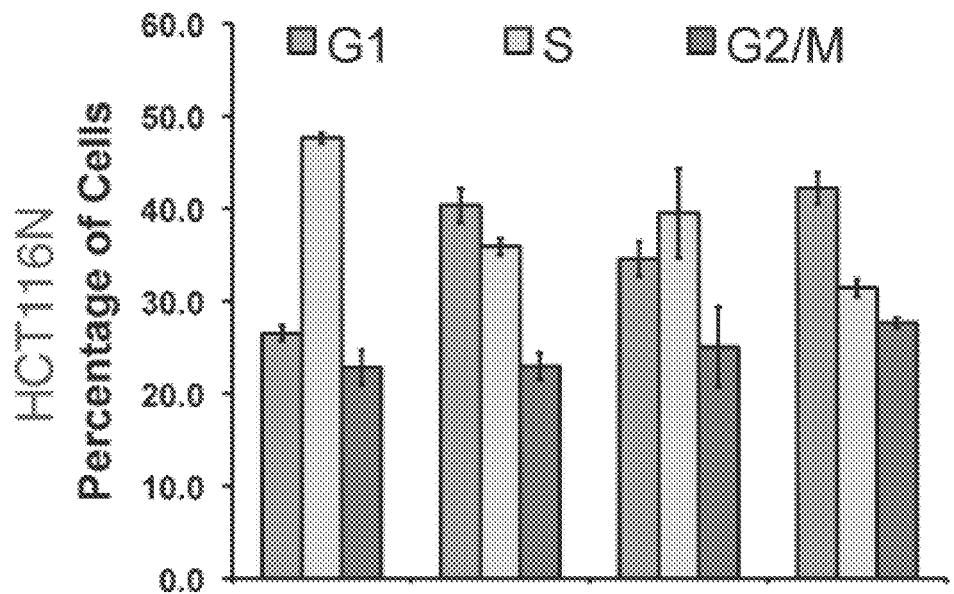
FIG. 35A is a graph of the cell cycle phase distribution (G (far left), S (middle), and G2/M (far right)) in the untreated HCT116N cells (−) and the [Rh(HDPA)$_2$chrysi]$^{3+}$ treated HCT116N cells (+) from FIGS. 34A and 34B, according to embodiments of the present invention.
Figure 35B:
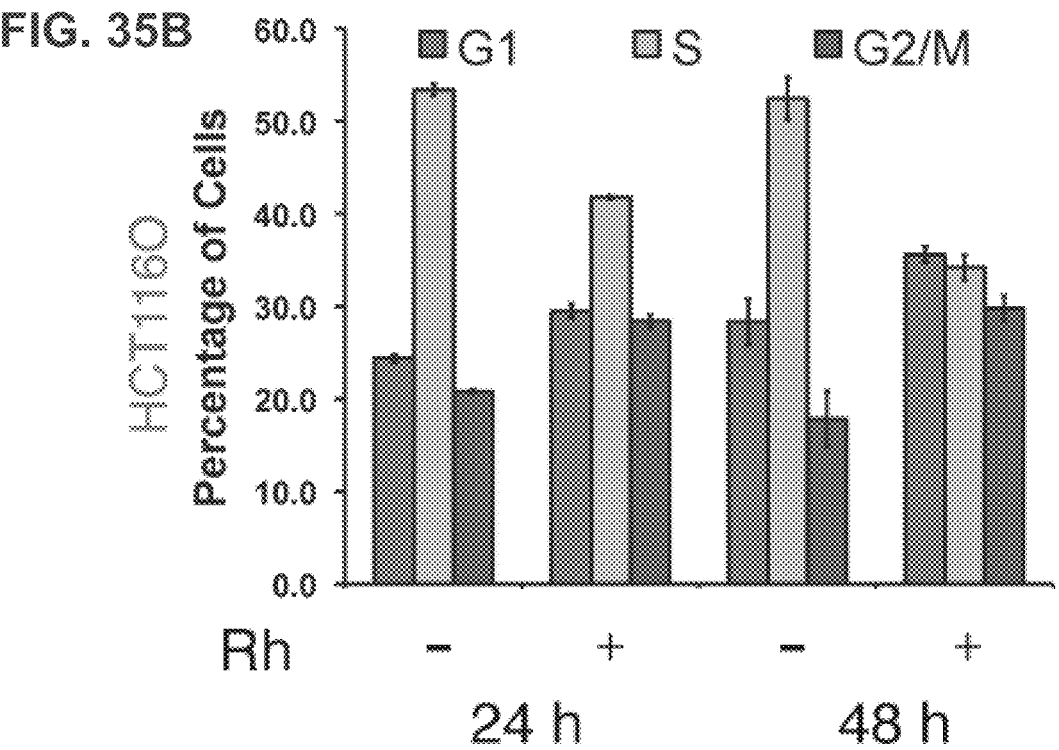
FIG. 35B is a graph of the cell cycle phase distribution (G (far left), S (middle), and G2/M (far right)) in the untreated HCT116O cells (−) and the [Rh(HDPA)$_2$chrysi]$^{3+}$ treated HCT116O cells (+) from FIGS. 34C and 34D, according to embodiments of the present invention.
Figure 36A:
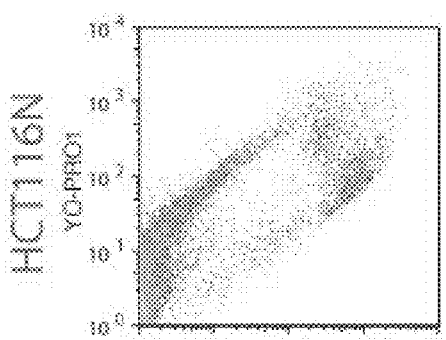
FIG. 36A is a distribution plotting the fluorescence from a population of cells stained with YO-PRO-1 and PI in HCT116N cells, according to embodiments of the present invention.
Figure 36B:
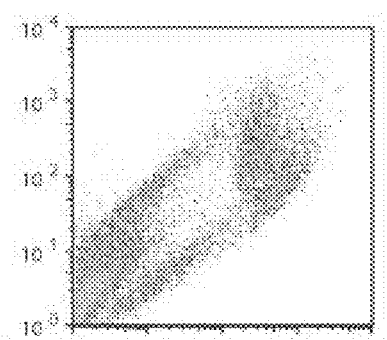
FIG. 36B is a distribution plotting the fluorescence from a population of cells stained with YO-PRO-1 and PI in HCT116N cells after treatment with 20 μM [Rh(HDPA)$_2$chrysi]$^{3+}$ for a 72 hour incubation, according to embodiments of the present invention.
Figure 36C:
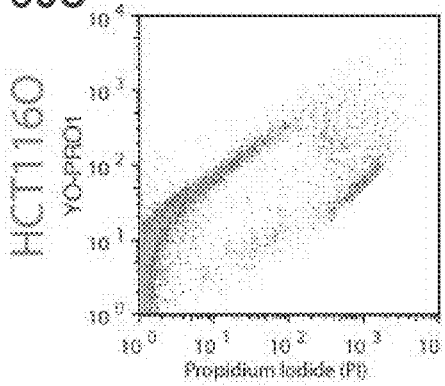
FIG. 36C is a distribution plotting the fluorescence from a population of cells stained with YO-PRO-1 and PI in HCT116O cells, according to embodiments of the present invention.
Figure 36D:
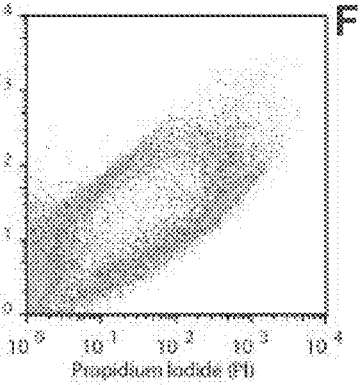
FIG. 36D is a distribution plotting the fluorescence from a population of cells stained with YO-PRO-1 and PI in HCT116O cells after treatment with 20 μM [Rh(HDPA)$_2$chrysi]$^{3+}$ for a 72 hour incubation, according to embodiments of the present invention.

As shown in FIG. 32, cells incubated with [Rh(HDPA)$_2$chrysi]$^{3+}$ exhibit an increase in cellular uptake compared to cells incubated with [Rh(bpy)$_2$chrysi]$^3$ or [Rh(NH$_3$)$_4$chrysi]$^3$. FIGS. 33A and 33B show the amount of cellular uptake and localization for the indicated rhodium complexes.

Example 32

Cell Cycle Distribution Flow Cytometry Assay

Cells were harvested from adherent culture by trypsinization and washed with cold PBS. The resultant pellet was resuspended in PBS (chilled to 4° C.), and ice-cold ethanol was added dropwise to a final concentration of 70% (v/v), with continuous gentle agitation. Cells were fixed at 4° C. for 30 minutes and stored for up to one week. Prior to analysis, the fixed cells in 70% ethanol were diluted 1:3 in cold PBS and centrifuged at 1,400×g for 5 minutes. The resultant pellet was washed twice and resuspended in ice-cold PBS. Ribonuclease was added to a final concentration of 30 µg/mL and the cells were incubated overnight at 4° C. The next day propidium iodide was added to a final concentration of 20 µg/mL and cells were analyzed by flow cytometry. Data analysis was performed using the FloJo software package (v 8.7.1).

Example 33

Cell Death Mode Flow Cytometry Assay

To characterize the cell death occurring in response to rhodium treatment, a dye exclusion flow cytometry assay was used as described in Idziorek et al., 1995 *J. Immunol. Methods*, 185, 249-258, the entire contents of which is incorporated herein by reference. The assay differentiates between live cells, dead cells, and cells undergoing apoptosis or necrosis through concurrent staining with propidium iodide (a dead cell permeable dye) and YO-PRO-1 (an apoptotic cell permeable dye). By plotting the fluorescence of the YO-PRO-1 channel against the PI channel, a pattern emerges. Healthy cells are seen in the lower lefthand corner of the plot in FIGS. 36A-36D. Apoptotic cells exhibit higher YO-PRO-1 fluorescence, but still exclude propidium iodide, placing them in the upper lefthand quadrant of the pattern. Dead cells admit both dyes and are therefore seen in the upper righthand quadrant of the image. Upon flow cytometry analysis, cells can be classified as live, apoptotic, necrotic, or dead by defining regions in the fluorescence plane corresponding to each category.

Figure 37A:
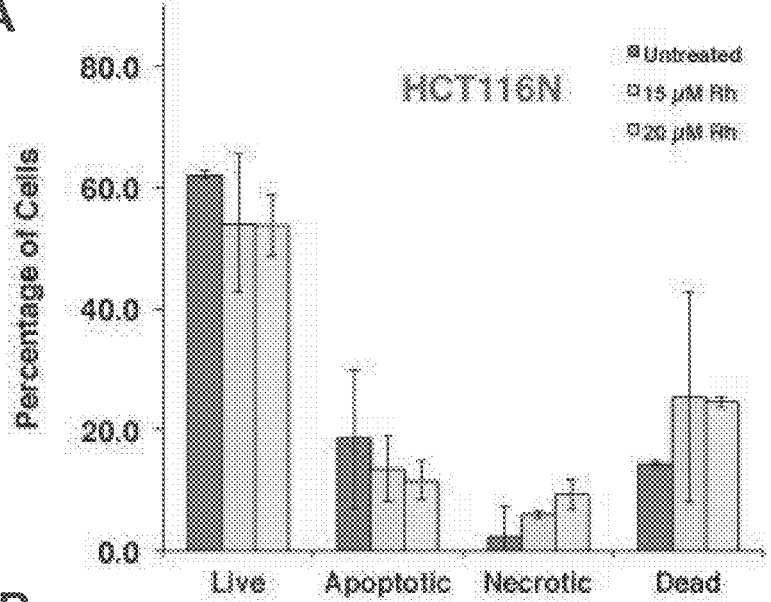
FIG. 37A is a graph of the number of cells that are Live, Apoptotic, Necrotic, and Dead determined from the raw fluorescence data of the HCT116N cells of FIGS. 36A and 36B, according to embodiments of the present invention.
Figure 37B:
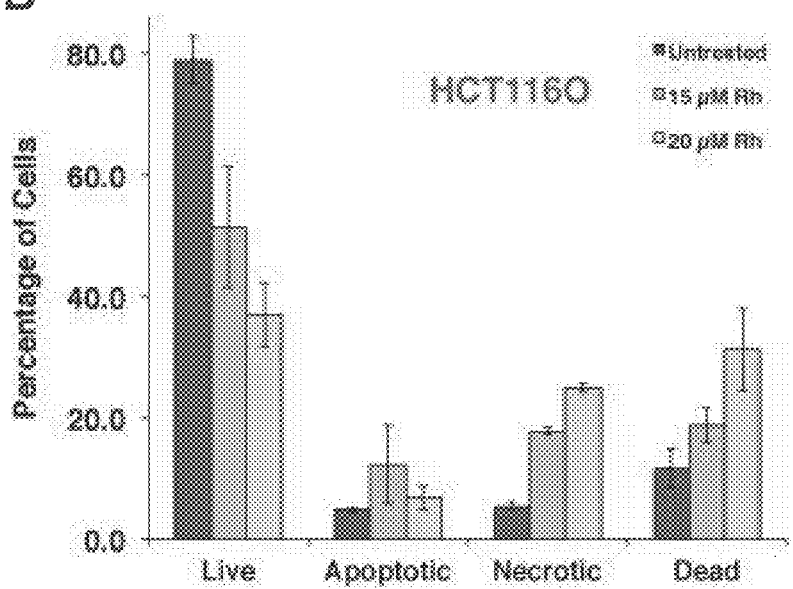
FIG. 37B is a graph of the number of cells that are Live, Apoptotic, Necrotic, and Dead determined from the raw fluorescence data of the HCT116O cells of FIGS. 36C and 36D, according to embodiments of the present invention.

The HCT116N and HCT116O cell lines were incubated with 0-25 µM of [Rh(HDPA)$_2$chrysi]$^{3+}$ for 24-72 hours. After harvesting the cells and staining with both PI and YO-PRO-1, the cells were analyzed by flow cytometry to obtain raw fluorescence data. Representative data for 20 µM rhodium treatment for 72 hours are shown. YO-PRO-1 fluorescence is shown on the y-axis, and PI fluorescence is shown on the x-axis. The raw data were analyzed by gating the fluorescence events into one of four categories, depending on the fluorescence levels of the two dyes. FIGS. 37A-37B also show histograms of live, apoptotic, necrotic, and dead cells for the HCT116N and HCT116O cell lines based on the flow cytometry. Treatment with the indicated rhodium complex was either 15 or 20 M [Rh(HDPA)$_2$chrysi]$^{3+}$ for 72 hours. As before, rhodium treatment alone induces necrosis preferentially in the MMR-deficient HCT116O cell line; there is no significant change in the percentage of cells in the apoptotic region in either cell line. The effect is significantly more pronounced in the MMR-deficient HCT116O cell line, which drops from 79±3.8% to 37±5.3% after treatment with 20 µM [Rh(HDPA)$_2$chrysi]$^{3+}$, versus the MMR-proficient HCT116N cell line, which shows a minimal decrease in live cells from 62±0.6% to 54±5.1% after treatment with 20 µM [Rh(HDPA)$_2$chrysi]$^{3+}$.

After 24, 48, or 72 hour incubation with the selected rhodium complex, cells were harvested from adherent culture by trypsinization and washed with cold PBS, and centrifuged at 2,000 rpm for 5 minutes. The resultant pellets were resuspended in PBS to a concentration of 10$^6$ cells/mL and stained with propidium iodide to a final concentration of 1 µg/mL and with YO-PRO-1 (an apoptotic cell permeable dye) to a final concentration of 200 nM for 30 minutes prior to analysis by flow cytometry.

Example 34

Caspase Inhibition

In order to elucidate the mechanism of action for the cytotoxicity caused by a metalloinsertor complex of Formula I, the MTT cytotoxicity assay was repeated in the absence and presence of the pan-caspase inhibitor Z-VAD-FMK. This inhibitor works by irreversibly binding to the active site of caspases which participate in the apoptotic pathway. Z-VAD-FMK was added to a final concentration of 20 µM. The HCT116N and HCT116O cell lines were treated with 0-30 µM of the [Rh(HDPA)$_2$chrysi]$^{3+}$ complex for 24-72 hours. In addition, each treatment was also combined with the inhibitor at a final concentration of 20 µM. The rhodium complex exhibited selective toxicity in the repair-deficient HCT116O cell line, with cell viability dropping to 9.7±4.4% after treatment with 30 µM metal complex for 72 hours, versus 63±5.7% viability in the repair-proficient HCT116N cell line. Addition of the caspase inhibitor at 20 M offered no protection from rhodium to the HCT16N cell line (63±5.7% without inhibitor, 52±9.8% with inhibitor) or to the HCT116O cell line (9.7±4.4% without inhibitor, 9.8±7.8% with inhibitor). At a final concentration of 40 µM, the caspase inhibitor provided some protection from rhodium to the HCT116O cell line (16±10% without inhibitor, 28±3.7% with inhibitor), but this difference was small in relation to the differential between the HCT116N and HCT116O cell lines and roughly within error.

FIGS. 34A-34D, FIGS. 35A-35B, FIGS. 36A-36D, and FIGS. 37A-37B show results from flow cytometry assays of [Rh(HDPA)$_2$chrysi]3$^+$ HCT116N and HCT116O cells. As shown, selective cytotoxicity (cell death) is preceded by disruption of the cell cycle, and that cell death proceeds through a necrotic rather than apoptotic pathway. The caspase inhibition assay using shown in FIGS. 38A-38C shows that the selective cell death is caspase-independent—i.e. not apoptotic.

Example 35

PARP Inhibition

In order to determine the mechanism of action for cytotoxicity caused by a metalloinsertor complex of Formula I, the MTT cytotoxicity assay was repeated in conjunction with a panel of poly-ADP ribose polymerase (PARP) inhibitors: DPQ, 3-AB, 4-AN, and ABT-888, as described in Costantino et al., 2001, *J. Med. Chem.*, 44, 3786-3794; Purnell et al., 1980, *Biochem. J.* 185, 775-777; Banasik et al., 1992, *J. Biol. Chem.* 267, 1569-1575; and Donawho et al., 2007, *Clin. Cancer Res.*, 13, 2728-2737, the entire contents of all of which are incorporated herein by reference. The HCT116N and HCT116O cell lines were treated with 0 or 20 μM of the [Rh(HDPA)$_2$chrysi]$^{3+}$ complex for 72 hours, with or without one of the four inhibitors. The inhibitor 3,4-Dihydro-5[4-(1-piperindinyl)butoxy]-1(2H)-isoquinoline (DPQ) was added to a final concentration of 0, 25, or 50 μM; the inhibitor 3-aminobenzamide (3-AB) was added to a final concentration of 0, 2, or 3 mM; the inhibitor 4-amino-1,8-napthalimide (4-AN) was added to a final concentration of 0, 10, or 20 μM; and the inhibitor 2-((R)-2-Methylpyrrolidin-2-yl)-1H-benzimidazole-4-carboxamide (ABT-888) was added to a final concentration of 0, 5, or 10 μM. In each case, treatment with the inhibitor completely abolished the selective MMR-dependent effects of the rhodium compound, as determined by the difference between the percentage of viable cells in the HCT116N cell line and the percentage of viable cells in the HCT116O cell line. For example, in the case of the compound DPQ, this difference was 43±2.7% without inhibitor and 0.6±3.0% with inhibitor. Similar results are seen with each of the other three compounds as well; taken together, these data, as shown in FIGS. 39A-39D, indicate that PARP participates in the MMR-dependent response to [Rh(HDPA)$_2$chrysi]$^{3+}$.

As disclosed throughout and evidenced by the selective cytotoxicity data of FIGS. 17A-27 and FIGS. 46-47, metalloinsertor complexes of the present invention provide a means for selectively targeting MMR-deficient cells.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A composition comprising a complex represented by Formula I:

M$^{m+}$(L$_1$)(L$_2$)(L$_3$)(L$_4$)(L$_5$)      Formula I wherein M is rhodium or ruthenium;

m is 2 or 3;

L$_1$ is benzo[a]phenazine-5,6-diimine or chrysene-5,6-diimine;

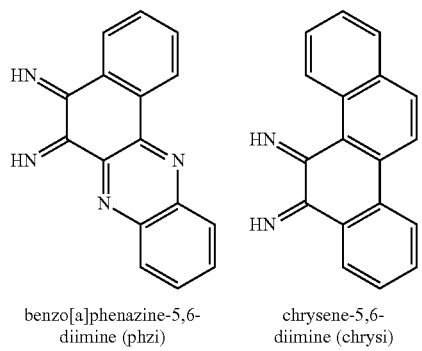

benzo[a]phenazine-5,6-diimine (phzi)      chrysene-5,6-diimine (chrysi)

wherein:

L$_2$ and L$_3$ are adjacent each other, and either L$_2$ and L$_3$ are both NH$_3$, or L$_2$ and L$_3$ combine to form a first single ligand with two coordination sites to M, L$_4$ and L$_5$ are adjacent each other, and either L$_4$ and L$_5$ are both NH$_3$, or L$_4$ and L$_5$ combine to form a second single ligand with two coordination sites to M, and each of the first and second single ligands is independently selected from the group consisting of:

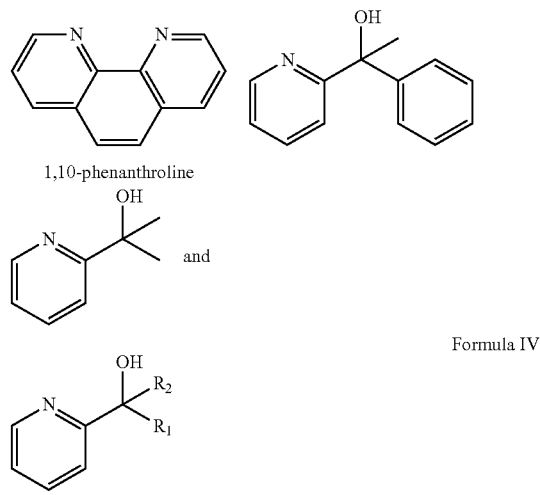

1,10-phenanthroline

Formula IV wherein, in Formula IV, R$_1$ and R$_2$ are each independently selected from the group consisting of:
  alkyl groups terminating in one selected from the group consisting of CH$_3$, OH, SH, NH$_2$, COOH, N$_3$, and alkynyl-linked peptide moieties, and
  PEGylated groups terminating in one selected from the group consisting of CH$_3$, OH, SH, NH$_2$, COOH, N$_3$, and alkynyl-linked peptide moieties,
  wherein when L$_2$ and L$_3$ are both NH$_3$, neither of L$_4$ or L$_5$ is NH$_3$ and the second single ligand is not phen, and when L$_4$ and L$_5$ are both NH$_3$, neither of L$_2$ or L$_3$ is NH$_3$ and the first single ligand is not phen, and
  wherein the first single ligand and the second single ligand are different.

2. The composition of claim 1, wherein the first single ligand and/or the second single ligand is a ligand selected from the group consisting of phen, PPE and PyPrOH.

3. The composition of claim 1, wherein M is rhodium.

4. The composition of claim 1, wherein L$_2$ and L$_3$ are both NH$_3$.

5. The composition of claim 4, wherein the second single ligand is PPE or PyPrOH.

6. The composition of claim 1, wherein the complex represented by Formula I comprises a complex selected from the group consisting of M$^{m+}$(L$_1$)(phen)(PPE) and M$^{m+}$(L$_1$)(phen)(PyPrO).

7. The composition of claim 1, wherein the complex represented by Formula I comprises a complex selected from the group consisting of M$^{m+}$(chrysi)(phen)(PPE) and M$^{m+}$(chrysi)(phen)(PyPrO).

8. The composition of claim 1, wherein the complex represented by Formula I comprises a complex selected from the group consisting of Rh$^{3+}$(chrysi)(phen)(PPE) and Rh$^{3+}$(chrysi)(phen)(PyPrO).

9. A method of selectively inducing cytotoxicity in mismatch repair (MMR)-deficient cells, comprising:
  providing the composition of claim 1 to the MMR-deficient cells.

10. The method of claim 9, wherein providing the composition of claim 1 comprises providing the composition in vitro.

11. The method of claim 9, wherein providing the composition of claim 1 comprises providing the composition in vivo.

12. A method of selectively decreasing cell proliferation, comprising:
  providing the composition of claim 1 to MMR-deficient cells.

13. A pharmaceutical composition, comprising:
an effective amount of the composition of claim 1; and
a pharmaceutically acceptable carrier.

14. A composition comprising a complex represented by Formula I:

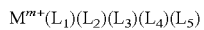   Formula I wherein M is rhodium or ruthenium;
in is 2 or 3;
$L_1$ is benzo[a]phenazine-5,6-diimine or chrysene-5,6-diimine;

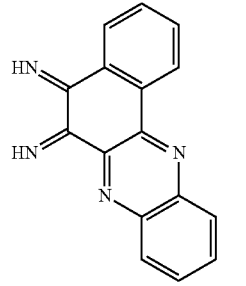 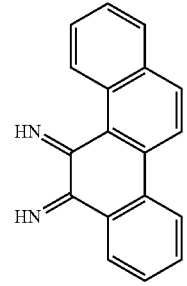

benzo[a]phenazine-5,6-diimine (phzi)   chrysene-5,6-diimine (chrysi)

wherein:
$L_2$ and $L_3$ combine to form a first single ligand with two coordination sites to M,
$L_4$ and $L_5$ combine to form a second single ligand with two coordination sites to M, and
each of the first and second single ligands is independently selected from the group consisting of:

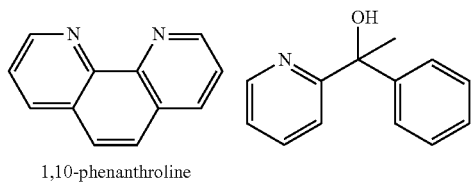

1,10-phenanthroline

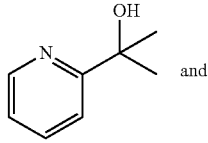   and

Formula IV

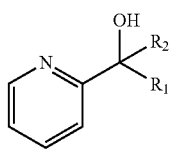

wherein, in Formula IV, $R_1$ and $R_2$ are each independently selected from the group consisting of:
alkyl groups terminating in one selected from the group consisting of $CH_3$, OH, SH, $NH_2$, COOH, $N_3$, and alkynyl-linked peptide moieties, and
PEGylated groups terminating in one selected from the group consisting of $CH_3$, OH, SH, $NH_2$, COOH, $N_3$, and alkynyl-linked peptide moieties, and
wherein the first single ligand and the second single ligand are different.

* * * * *